(12) United States Patent
Hyde et al.

(10) Patent No.: US 8,535,261 B2
(45) Date of Patent: Sep. 17, 2013

(54) ADMINISTERING A THERAPEUTIC AGENT WITH MORE THAN ONE TAGGANT

(75) Inventors: Roderick A. Hyde, Redmond, WA (US); Muriel Y. Ishikawa, Livermore, CA (US); Jordin T. Kare, Seattle, WA (US); Eric C. Leuthardt, St. Louis, MO (US); Dennis J. Rivet, Portsmouth, VA (US); Lowell L. Wood, Jr., Bellevue, WA (US); Victoria Y. H. Wood, Livermore, CA (US)

(73) Assignee: The Invention Science Fund I, LLC, Bellevue, WA (US)

( * ) Notice: Subject to any disclaimer, the term of this patent is extended or adjusted under 35 U.S.C. 154(b) by 1257 days.

(21) Appl. No.: 12/291,509

(22) Filed: Nov. 10, 2008

(65) Prior Publication Data

US 2010/0121186 A1    May 13, 2010

(51) Int. Cl.
  *A61M 31/00*    (2006.01)
(52) U.S. Cl.
  USPC ............................. 604/65; 604/66
(58) Field of Classification Search
  USPC ................................... 604/65, 66
  See application file for complete search history.

(56) References Cited

U.S. PATENT DOCUMENTS

| | | | |
|---|---|---|---|
| 6,068,981 A | 5/2000 | Rittenburg et al. |
| 6,663,846 B1 | 12/2003 | McCombs et al. |
| 6,671,563 B1 | 12/2003 | Engelson et al. |
| 7,052,854 B2 | 5/2006 | Melker et al. |
| 2002/0106685 A1 | 8/2002 | Henning et al. |
| 2003/0194374 A1 | 10/2003 | Heasley et al. |
| 2004/0030262 A1 | 2/2004 | Fisher et al. |
| 2004/0133095 A1 | 7/2004 | Dunki-Jacobs et al. |
| 2004/0147592 A1 | 7/2004 | Quay |
| 2006/0062734 A1 | 3/2006 | Melker et al. |
| 2007/0012784 A1 | 1/2007 | Mercolino |
| 2007/0172424 A1 | 7/2007 | Roser |
| 2007/0224128 A1 | 9/2007 | Dennis et al. |
| 2010/0119455 A1 | 5/2010 | Hyde et al. |
| 2010/0119456 A1 | 5/2010 | Hyde et al. |
| 2010/0121176 A1 | 5/2010 | Hyde et al. |
| 2010/0121177 A1 | 5/2010 | Hyde et al. |
| 2010/0121185 A1 | 5/2010 | Hyde et al. |
| 2010/0121187 A1 | 5/2010 | Hyde et al. |
| 2010/0121581 A1 | 5/2010 | Hyde et al. |

FOREIGN PATENT DOCUMENTS

WO    WO 2006/129301 A2    12/2006

OTHER PUBLICATIONS

Azar et al.; "Probes for Optical Imaging and SPECT/PET"; Section 16.3.2, Translational Multimodality Optical Imaging; 2008; printed from web Oct. 23, 2011(as provided by examiner); 3 pages; located at: http://books.google.com/books?id=AFW8xHNS6pgC&pg=PA336&lpg=PA336&dq=do+any+dyes+or+fluorophores+contain+radi#v=onepage&q=do%20any%20dyes%20or%20fluorophores%20contain%20radi&f=false; Excerpt from Google Books.

(Continued)

*Primary Examiner* — Bhisma Mehta
(74) *Attorney, Agent, or Firm* — Suiter Swantz pc llo

(57) ABSTRACT

A system for administering a therapeutic agent to a subject; for administering a first pharmaceutically-acceptable taggant to the subject at least substantially concurrent with the therapeutic agent, the first pharmaceutically-acceptable taggant having a pharmacokinetic profile; and for administering a second pharmaceutically-acceptable taggant to the subject with the first pharmaceutically-acceptable taggant, the second pharmaceutically-acceptable taggant having a pharmacokinetic profile different from the pharmacokinetic profile of the first pharmaceutically-acceptable taggant.

43 Claims, 35 Drawing Sheets

(56) References Cited

OTHER PUBLICATIONS

Definition from Collins English Dictionary; "Fluorophore"; Collins English Dictionary; 2000; retrieved from the internet and printed by examiner on Oct. 22, 2011; 2 pages (as provided by examiner); located at: http://www.credoreference.com/entry/hcengdict/fluorophore; HarperCollins Publishers; UK.

Definition from Mosby's Dictionary of Medicine, Nursing, & Health Professions; "Pharmacokinetics"; Mosby's Dictionary of Medicine, Nursing & Health Professions; 2009; retrieved from the internet and printed by examiner on Oct. 22, 2011; 2 pages (as provided by examiner); located at: http://www.credoreference.com/entry/6686418 ; Elsevier, Inc.

ACNP, Main Page; bearing a date of 2008, printed Jun. 29, 2012; pp. 1-2; American College of Neuropsychopharmacology; located at: www.acnp.org.

American Society of Health-System Pharmacists (ASHP), Main Page; printed Jun. 29, 2012; pp. 1-2; American Society of Health-System Pharmacists; located at: http://www.ashp.org/.

Bloomberg BNA; "*Ariad Pharmaceuticals Inc. v. Eli Lilly & Co.*"; Intellectual Property Law Resource Center; bearing a date of 2012, decided on Mar. 22, 2010; pp. 1-28; The Bureau of National Affairs, Inc.; located at: http://iplaw.bna.com/iprc/display/batch_print_display.adp?searchid=17884112.

Boros et al.; "Metabolic Biomarker and Kinase Drug Target Discovery in Cancer Using Stable Isotope-Based Dynamic Metabolic Profiling (SIDMAP)"; Current Cancer Drug Targets; bearing a date of 2003; pp. 447-455; vol. 3, No. 6; Bentham Science Publishers Ltd.

Drugs.com; "Acetaminophen Pharmacokinetics"; printed Jun. 28, 2012; pp. 1-2; located at: www.drugs.com/monograph/acetaminophen.html.

Drugs.com; "Procrit, Pharmacokinetics"; printed Jun. 28, 2012; p. 1; located at: http://www.drugs.com/pro/procrit.html.

Drugs.com; "Tylenol® Sore Throat"; printed Jun. 28, 2012; pp. 1-8; located at: www.drugs.com/otc/1049606/tylenol-sore-throat.html.

Federal Register; bearing a date of Wednesday, Feb. 9, 2011; p. 7166; vol. 76, No. 27.

Flury et al.; "Brilliant Blue FCF as a Dye Tracer for Solute Transport Studies—A Toxicological Overview"; Journal of Environmental Quality; bearing a date of Sep.-Oct. 1994; pp. 1108-1112; vol. 23, No. 5; ASA,CSSA, SSSA; Madison, WI (best available copy by examiner).

Greenblatt et al.; "Pharmacokinetics and Pharmacodynamics"; Psychopharmacology: The Fourth Generation of Progress; bearing a date of 2000, printed Jun. 26, 2012; pp. 1-8.

"Half-Life"; Merriam-Webster Dictionary; bearing a date of 2012, printed Jun. 22, 2012; pp. 1-2; Merriam-Webster, Incorporated; located at: http://www.merriam-webster.com/dictionary/half%20life.

Helmenstine, Ph.D., Anne Marie; "What Materials Glow Under a Black or Ultraviolet Light?"; About.com Guide; printed on Jun. 29, 2012; pp. 1-2; About.com, Inc.; located at: http://chemistry.about.com/cs/howthingswork/f/blblacklight.htm.

IGA et al.; "Pharmacokinetic Study of Biliary Excretion. II. Comparison of Excretion Behavior in Triphenylmethane Dyes [1,2]"; Chem. Pharm. Bull.; bearing a date of 1971, received Jun. 6, 1970; pp. 273-281; vol. 19, No. 2.

Jani et al.; "Biliary Excretion of Polystyrene Microspheres with Covalently Linked FITC Fluorescence After Oral and Parenteral Administration to Male Wistar Rats"; Journal of Drug Targeting; bearing a date of 1996, accepted Mar. 19, 1996; pp. 87-93; vol. 34; OPA (Overseas Publishers Association); Venezuela.

Jenkins, Ph.D., Amanda J.; "Chapter 3, Toxicokinetics and Factors Affecting Pharmacokinetic Parameters"; Pharmacokinetics and Pharmacodynamics of Abused Drugs; bearing a date of 2008; pp. 21-24; Taylor & Francis Group, LLC.

Knovel; "01373. Brilliant Blue FCF"; Merck Index; bearing a date of 2006, 2012; pp. 1-2; Merck Sharp & Dohme Corp.; Whitehouse Station, NJ; located at: http://www.knovel.com/web/portal/browse/display?_EXT_KNOVEL_DISPLAY_bookid=1381&Vertical ID=0.

"Lesson 1, Introduction to Pharmacokinetics and Pharmacodynamics"; American Society of Health-System Pharmacists (ASHP); printed Jun. 14, 2012; pp. 1-18; located at: www.ashp.org/DocLibrary/Bookstore/P2418-Chapter1.aspx.

Mayo Clinic Staff; "Urine Color"; MayoClinic.com; bearing a date of Sep. 30, 2011; pp. 1-3; Mayo Foundation for Medical Education and Research (MFMER); located at: http://www.mayoclinic.com/health/urine-color/DS01026/METHOD=print&DSECTION=all (best available copy by examiner).

RxMed; "Pharmaceutical Information—Vitamin B2"; printed on Jun. 21, 2012; pp. 1-2; located at: http://www.rxmed.com/b.main/b2.pharmaceutical/b2.1.monographs/CPS-%20Monographs/CPS-%20(General%20Monographs-%20V)/VITAMIN%20B2.html.

"Scope-Original Mint, Material Safety Data Sheet"; printed Jun. 26, 2012 ; pp. 1-4; Proctor & Gamble; located at: http://www.pgproductsafety.com/productsafety/msds/health_care/oral_care/Scope_Original_Mint.pdf.

Sigma-Aldrich; "Nicholson Metabolic Pathway Charts"; bearing a date of 2002, printed Jun. 29, 2012; pp. 1-2; Sigma-Aldrich Co. LLC; St. Louis, MO; located at: http://www.sigmaaldrich.com/life-science/metabolomics/learning-center/metabolic-pathways.printerview.html (best available copy by examiner).

Singh, BN; "Effects of Food on Clinical Pharmacokinetics"; Clin Pharmacokinet.; bearing a date of Sep. 1999; pp. 213-255 (Abstract only, pp. 1-2); vol. 3.

Toutain et al.; "Species Differences in Pharmacokinetcs and Pharmacodynamics"; Handb Exp Pharmacol.; bearing a date of 2010; pp. 19-48 (Abstract only, pp. 1-2); vol. 199.

Vanderhoff, M.D. et al.; "Proton Pump Inhibitors: An Update"; American Family Physician; bearing a date of Jul. 15, 2002; pp. 273-280; vol. 66, No. 2; American Academy of Family Physicians.

Yetley, Elizabeth A.; "Multivitamin and Multimineral Dietary Supplements: Definitions, Characterization, Bioavailability, and Drug Interactions [1-3]"; The American Journal of Clinical Nutrition; bearing a date of 2007, printed Jun. 14, 2012; pp. 269S-276S; vol. 85; American Society for Nutrition.

Aschenbrenner et al.; "Drug Therapy in Nursing"; 2009; 5 pages (1306 pages; pages in part 40, 45, 48 and 141); Lippincott Williams & Wilkins.

Evans, Gary; "A Handbook of Bioanalysis and Drug Metabolism"; Mar. 29, 2004; 408 pages (p. 9); CRC Press.

Ghosh et al.; "Theory and Practice of Contemporary Pharmaceutics"; Dec. 12, 2010; 564 pages (p. 78); CRC Press.

Glover et al.; "Brompton's Mixture in Alleviating Pain of Terminal Neoplastic Disease: Preliminary Results"; Southern Medical Journal; Mar. 1980; pp. 278-282; vol. 73, No. 3.

Ishihara et al.; "Fluid Volume Monitoring with Glucose Dilution"; Jan. 1, 2007; 160 pages (p. 47); Springer.

Jones et al.; "Concentration-time profiles of ethanol in arterial and venous blood and end-expired breath during and after intravenous infusion"; Journal of Forensic Science; Nov. 1997, printed on Mar. 11, 2013; pp. 1088-94 (1 page); vol. 42, No. 6; PubMed, NCBI (Abstract only).

Jufer et al.; "Elimination of Cocaine and Metabolites in Plasma, Saliva, and Urine Following Repeated Oral Administration to Human Volunteers"; Journal of Analytical Toxicology; Oct. 2000; pp. 467-477; vol. 24.

Julien, Robert M.; "A Primer of Drug Action"; Sep. 17, 2004; 690 pages (p. 169); MacMillan.

"Leukemia-Acute Myeloid (Myelogenous): Can acute myeloid leukemia be prevented?"; Last Revised: Jan. 18, 2013; Printed on: Mar. 11, 2013; pp. 1-3; American Cancer Society, Inc.; Located at: http://www.cancer.org/cancer/leukemia-acutemyeloidaml/detailedguide/leukemia-acute-myeloid-myelogenous-prevention.

"Mental Illness"; Mayo Clinic; Sep. 15, 2012; pp. 1-13; Mayo Foundation for Medical Education and Research (MFMER); Located at: http://www.mayoclinic.com/health/mental-illness/DS01104.

"Schizophrenia"; Mayo Clinic; Jan. 30, 2010; pp. 1-8; Mayo Foundation for Medical Education and Research (MFMER); Located at: http://www.mayoclinic.com/health/schizophrenia/DS00196.

"Drugs and Human Performance Fact Sheets—Morphine (and Heroin)"; Printed on Mar. 11, 2013; pp. 1-7; Located at: http://www.nhtsa.gov.people/injury/research/job185drugs/morphine.htm.

Torchilin, Vladimir P.; "Recent Advances with Liposomes as Pharmaceutical Carriers"; Nature Reviews Drug Discovery; Feb. 2005; pp. 145-160; vol. 4.

"Trichloromethane—Substance Summary"; PubChem; Printed on Mar. 11, 2013; pp. 1-8; Located at: http://pubchem.ncbi.nlm.nih.gov/summary/summary.cgi?sid=14717799.

Werry et al.; "Practitioner's Guide to Psychoactive Drugs for Children and Adolescents"; 1999; 502 pages (p. 253); Springer.

ADMINISTERING A THERAPEUTIC AGENT WITH MORE THAN ONE TAGGANT

BACKGROUND

When a therapeutic agent is administered to a subject, it is oftentimes important that an appropriate dosing schedule be maintained. Thus, the compliance of the patient in following the dosing regimen and the administration time of a therapeutic agent may be of interest to patients and health care providers alike.

SUMMARY

In one aspect, a method includes, but is not limited to, detecting a concentration of at least one of a first pharmaceutically-acceptable taggant administered to a subject at least substantially concurrent with a therapeutic agent or a metabolic byproduct of the first pharmaceutically-acceptable taggant, the first pharmaceutically-acceptable taggant having an operably detectable pharmacokinetic profile; and detecting a concentration of at least one of a second pharmaceutically-acceptable taggant administered to the subject with the first pharmaceutically-acceptable taggant while the first pharmaceutically-acceptable taggant is still operably detectable or a metabolic byproduct of the second pharmaceutically-acceptable taggant, the second pharmaceutically-acceptable taggant having an operably detectable pharmacokinetic profile different from the pharmacokinetic profile of the first pharmaceutically-acceptable taggant.

In another aspect, a method includes but is not limited to detecting a level of at least one of a first pharmaceutically-acceptable taggant administered to a subject at least substantially concurrent with a therapeutic agent or a metabolic byproduct of the first pharmaceutically-acceptable taggant, the first pharmaceutically-acceptable taggant having an operably detectable pharmacokinetic profile, the level of the at least one of the first pharmaceutically-acceptable taggant or the metabolic byproduct of the first pharmaceutically-acceptable taggant detected relative to a level of at least one of a second pharmaceutically-acceptable taggant administered to the subject while the first pharmaceutically-acceptable taggant is still operably detectable or a metabolic byproduct of the second pharmaceutically-acceptable taggant, the second pharmaceutically-acceptable taggant having an operably detectable pharmacokinetic profile different from the pharmacokinetic profile of the first pharmaceutically-acceptable taggant; comparing the detected relative levels of the at least one of the first pharmaceutically-acceptable taggant or the metabolic byproduct of the first pharmaceutically-acceptable taggant and the at least one of the second pharmaceutically-acceptable taggant or the metabolic byproduct of the second pharmaceutically-acceptable taggant to the relative pharmacokinetic profiles of the first pharmaceutically-acceptable taggant and the second pharmaceutically-acceptable taggant; and approximating a time period lapsed between administering the therapeutic agent to the subject and detecting the level of the at least one of the first pharmaceutically-acceptable taggant or the metabolic byproduct of the first pharmaceutically-acceptable taggant relative to the level of the at least one of the second pharmaceutically-acceptable taggant or the metabolic byproduct of the second pharmaceutically-acceptable taggant.

In one or more various aspects, related systems include but are not limited to circuitry and/or programming for effecting the herein-referenced method aspects; the circuitry and/or programming can be virtually any combination of hardware, software, and/or firmware configured to effect the herein-referenced method aspects depending upon the design choices of the system designer.

In one aspect, a system includes but is not limited to a means for administering a therapeutic agent to a subject; a means for administering a first pharmaceutically-acceptable taggant to the subject at least substantially concurrent with the therapeutic agent, the first pharmaceutically-acceptable taggant having a pharmacokinetic profile; and a means for administering a second pharmaceutically-acceptable taggant to the subject with the first pharmaceutically-acceptable taggant, the second pharmaceutically-acceptable taggant having a pharmacokinetic profile different from the pharmacokinetic profile of the first pharmaceutically-acceptable taggant.

In another aspect, a system includes but is not limited to a means for detecting a concentration of at least one of a first pharmaceutically-acceptable taggant administered to a subject at least substantially concurrent with a therapeutic agent or a metabolic byproduct of the first pharmaceutically-acceptable taggant, the first pharmaceutically-acceptable taggant having a pharmacokinetic profile; a means for detecting a concentration of at least one of a second pharmaceutically-acceptable taggant administered to the subject with the first pharmaceutically-acceptable taggant or a metabolic byproduct of the second pharmaceutically-acceptable taggant, the second pharmaceutically-acceptable taggant having a pharmacokinetic profile different from the pharmacokinetic profile of the first pharmaceutically-acceptable taggant; a means for referencing the concentration of the at least one of the first pharmaceutically-acceptable taggant or the metabolic byproduct of the first pharmaceutically-acceptable taggant to the pharmacokinetic profile of the first pharmaceutically-acceptable taggant; a means for referencing the concentration of the at least one of the second pharmaceutically-acceptable taggant or the metabolic byproduct of the second pharmaceutically-acceptable taggant to the pharmacokinetic profile of the second pharmaceutically-acceptable taggant; and a means for approximating a time period lapsed between administering the therapeutic agent to the subject and detecting the concentration of the at least one of the second pharmaceutically-acceptable taggant or the metabolic byproduct of the second pharmaceutically-acceptable taggant.

In a further aspect, a system includes but is not limited to a means for detecting a level of at least one of a first pharmaceutically-acceptable taggant administered to a subject at least substantially concurrent with a therapeutic agent or a metabolic byproduct of the first pharmaceutically-acceptable taggant, the first pharmaceutically-acceptable taggant having a pharmacokinetic profile, the level of the at least one of the first pharmaceutically-acceptable taggant or the metabolic byproduct of the first pharmaceutically-acceptable taggant detected relative to a level of at least one of a second pharmaceutically-acceptable taggant administered to the subject with the first pharmaceutically-acceptable taggant or a metabolic byproduct of the second pharmaceutically-acceptable taggant, the second pharmaceutically-acceptable taggant having a pharmacokinetic profile different from the pharmacokinetic profile of the first pharmaceutically-acceptable taggant; a means for comparing the relative levels of the at least one of the first pharmaceutically-acceptable taggant or the metabolic byproduct of the first pharmaceutically-acceptable taggant and the at least one of the second pharmaceutically-acceptable taggant or the metabolic byproduct of the second pharmaceutically-acceptable taggant to the relative pharmacokinetic profiles of the first pharmaceutically-acceptable taggant and the second pharmaceutically-acceptable taggant; and a means for approximating a time period lapsed between administering the therapeutic agent to the subject and detecting the level of the at least one of the first pharmaceutically-acceptable taggant or the metabolic byproduct of the first pharmaceutically-acceptable taggant relative to the level of the at least one of the second pharmaceutically-acceptable taggant or the metabolic byproduct of the second pharmaceutically-acceptable taggant.

A device includes a means for detecting a concentration of at least one of a first pharmaceutically-acceptable taggant administered to a subject at least substantially concurrent with a therapeutic agent or a metabolic byproduct of the first pharmaceutically-acceptable taggant, the first pharmaceutically-acceptable taggant having a pharmacokinetic profile; a means for detecting a concentration of at least one of a second pharmaceutically-acceptable taggant administered to the subject with the first pharmaceutically-acceptable taggant or a metabolic byproduct of the second pharmaceutically-acceptable taggant, the second pharmaceutically-acceptable taggant having a pharmacokinetic profile different from the pharmacokinetic profile of the first pharmaceutically-acceptable taggant; a means for referencing the concentration of the at least one of the first pharmaceutically-acceptable taggant or the metabolic byproduct of the first pharmaceutically-acceptable taggant to the pharmacokinetic profile of the first pharmaceutically-acceptable taggant; a means for referencing the concentration of the at least one of the second pharmaceutically-acceptable taggant or the metabolic byproduct of the second pharmaceutically-acceptable taggant to the pharmacokinetic profile of the second pharmaceutically-acceptable taggant; a means for approximating a time period lapsed between administering the therapeutic agent to the subject and detecting the concentration of the at least one of the second pharmaceutically-acceptable taggant or the metabolic byproduct of the second pharmaceutically-acceptable taggant; and a means for communicating information to a user indicative of the time period lapsed between administering the therapeutic agent to the subject and detecting the concentration of the at least one of the second pharmaceutically-acceptable taggant or the metabolic byproduct of the second pharmaceutically-acceptable taggant.

A device includes a means for detecting a level of at least one of a first pharmaceutically-acceptable taggant administered to a subject at least substantially concurrent with a therapeutic agent or a metabolic byproduct of the first pharmaceutically-acceptable taggant, the first pharmaceutically-acceptable taggant having a pharmacokinetic profile, the level of the at least one of the first pharmaceutically-acceptable taggant or the metabolic byproduct of the first pharmaceutically-acceptable taggant detected relative to a level of at least one of a second pharmaceutically-acceptable taggant administered to the subject with the first pharmaceutically-acceptable taggant or a metabolic byproduct of the second pharmaceutically-acceptable taggant, the second pharmaceutically-acceptable taggant having a pharmacokinetic profile different from the pharmacokinetic profile of the first pharmaceutically-acceptable taggant; a means for comparing the relative levels of the at least one of the first pharmaceutically-acceptable taggant or the metabolic byproduct of the first pharmaceutically-acceptable taggant and the at least one of the second pharmaceutically-acceptable taggant or the metabolic byproduct of the second pharmaceutically-acceptable taggant to the relative pharmacokinetic profiles of the first pharmaceutically-acceptable taggant and the second pharmaceutically-acceptable taggant; a means for approximating a time period lapsed between administering the therapeutic agent to the subject and detecting the level of the at least one of the first pharmaceutically-acceptable taggant or the metabolic byproduct of the first pharmaceutically-acceptable taggant relative to the level of the at least one of the second pharmaceutically-acceptable taggant or the metabolic byproduct of the second pharmaceutically-acceptable taggant; and a means for communicating information to a user indicative of the time period lapsed between administering the therapeutic agent to the subject and detecting the level of the at least one of the first pharmaceutically-acceptable taggant or the metabolic byproduct of the first pharmaceutically-acceptable taggant relative to the level of the at least one of the second pharmaceutically-acceptable taggant or the metabolic byproduct of the second pharmaceutically-acceptable taggant.

A pharmaceutical composition includes at least one therapeutic agent; a first pharmaceutically-acceptable taggant; and a second pharmaceutically-acceptable taggant, wherein the first pharmaceutically-acceptable taggant and the second pharmaceutically-acceptable taggant have different pharmacokinetic profiles, and wherein the therapeutic agent is present in a therapeutically-effective amount.

The foregoing is a summary and thus may contain simplifications, generalizations, inclusions, and/or omissions of detail; consequently, those skilled in the art will appreciate that the summary is illustrative only and is NOT intended to be in any way limiting. Other aspects, features, and advantages of the devices and/or processes and/or other subject matter described herein will become apparent in the teachings set forth herein. In addition to the foregoing, various other device, method and/or system and/or program product aspects are set forth and described in the teachings such as text (e.g., claims and/or detailed description) and/or drawings of the present disclosure.

DETAILED DESCRIPTION

Figure 1:
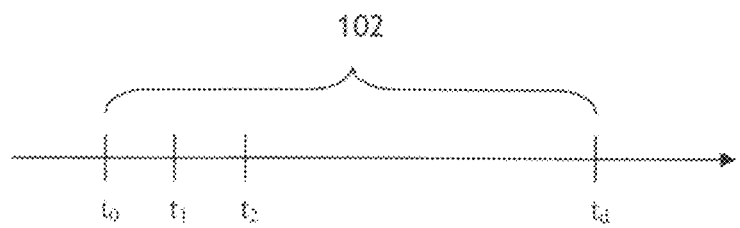
FIG. 1 is a timeline illustrating the administration of a therapeutic agent, a first taggant, and a second taggant; and the detection of the first taggant and the second taggant.

In the following detailed description, reference is made to the accompanying drawings, which form a part hereof. In the drawings, similar symbols typically identify similar components, unless context dictates otherwise. The illustrative embodiments described in the detailed description, drawings, and claims are not meant to be limiting. Other embodiments may be utilized, and other changes may be made, without departing from the spirit or scope of the subject matter presented here.

Referring now to FIG. 1, a period of time spanning from $t_0$ to $t_d$ is depicted. At time $t_0$, a therapeutic agent is administered to a subject. The therapeutic agent may be utilized for modulating, curing, diagnosing, mitigating, preventing, or treating one or more of a disease or a condition. The therapeutic agent may be utilized for enhancing one or more of a physical well-being or a mental well-being. The therapeutic agent may be administered to the subject via one or more of a duodenal route of administration, enterally, epicutaneously, epidurally, gastrically, an inhalational route of administration, intraarterially, an intracardiac route of administration, intradermatly, intramuscularly, intranasatly, intraocularly, intraosseous infusion, intraperitoneally, intrathecally, an intrauterine route of administration, intravaginally, intravenously, intravesicatty, intravitreally, nasally, nasogastric intubation, orally (e.g., via pill), rectally (e.g., via suppository), subcutaneously, sublingually, transdermally, or transmucosally. For example, the therapeutic agent may be administered to the subject orally, via nasal inhalation, or via an injection.

At least substantially concurrent with administering the therapeutic agent, a first pharmaceutically-acceptable taggant having a pharmacokinetic profile is administered to the subject at time $t_1$. A taggant may be defined as a marker/tracer and may include the taggant itself or a metabolite thereof. A taggant should not interact with the therapeutic agent, and should maintain no more than an acceptable toxicity level to the subject. In one embodiment, the first pharmaceutically-acceptable taggant (also referred to herein as first taggant) is considered to have been substantially concurrently administered with the therapeutic agent if the first pharmaceutically-acceptable taggant is administered concurrent with the therapeutic agent (i.e., $t_0$ is equal to $t_1$). In other embodiments, the first taggant is considered to be substantially concurrently administered with the therapeutic agent if the first pharmaceutically-acceptable taggant is administered subsequent to the therapeutic agent, but at a time when at least approximately 75% of the therapeutic agent still remains in the subject (i.e., the subject has cleared or metabolized no more than approximately 25% of the therapeutic agent). For example, if it takes approximately one hour for the subject to clear the first 25% of the therapeutic agent, then if the first pharmaceutically-acceptable taggant is administered within approximately the first hour after administering the therapeutic agent, the first pharmaceutically-acceptable taggant is considered to have been substantially concurrently administered. Further, the first pharmaceutically-acceptable taggant may be co-administered concurrently with the therapeutic agent. For example, the first pharmaceutically-acceptable taggant may be co-administered with the therapeutic agent in a single dose. Other substantially concurrent administration regimens of the first pharmaceutically-acceptable taggant include administering the first taggant when the subject has cleared or metabolized no more than 1%, 5%, 10%, 15%, or 20% of the therapeutic agent.

At time $t_2$, a second pharmaceutically-acceptable taggant (also referred to herein as second taggant) having a pharmacokinetic profile different from the pharmacokinetic profile of the first pharmaceutically-acceptable taggant is administered to the subject. The second pharmaceutically-acceptable taggant may be administered to the subject concurrent with the first pharmaceutically-acceptable taggant (i.e., where $t_1$ is equal to $t_2$). For example, the second pharmaceutically-acceptable taggant may be co-administered with the first pharmaceutically-acceptable taggant in the same dose. In another example, the second taggant may be co-administered with the first taggant, which itself may be co-administered with the therapeutic agent (i.e., $t_0$, $t_1$, and $t_2$ are equal). Alternatively, the second pharmaceutically-acceptable taggant may be administered to the subject subsequent to the first pharmaceutically-acceptable taggant. For example, the second pharmaceutically-acceptable taggant may be administered to the subject five minutes after administering the first pharmaceutically-acceptable taggant.

The actual times when the therapeutic agent, the first pharmaceutically-acceptable taggant, and the second pharmaceutically-acceptable taggant are administered to the subject (i.e., $t_0$, $t_1$, and $t_2$) may not be known, recorded, or otherwise readily available. In such cases, an estimated time instance at which the therapeutic agent was administered to the subject may be provided as described herein. For example, a health practitioner may determine adherence of a patient (subject) to a therapy model based on the estimated time of dosage of the therapeutic agent, when the actual time is not available. The present disclosure is directed to systems, methods, and devices for providing an estimated time at which the therapeutic agent was administered to the subject. For example, concentrations of the first and second taggant, or concentrations of metabolic byproducts of the first and second taggant in the subject may be detected at a known time instance $t_d$ (e.g., at the office of the health practitioner, where the detection time may be recorded). Based upon the concentrations detected, the pharmacokinetic profiles of the two taggants may be referenced in order to approximate a time period lapsed 102. The time period lapsed 102 may comprise an estimated duration between administering the therapeutic agent and conducting the detection of the second taggant. Therefore, the time when the therapeutic agent was administered may be estimated based on the time when the detection is conducted (i.e., known time instance $t_d$) minus the time period lapsed 102.

Figure 2:
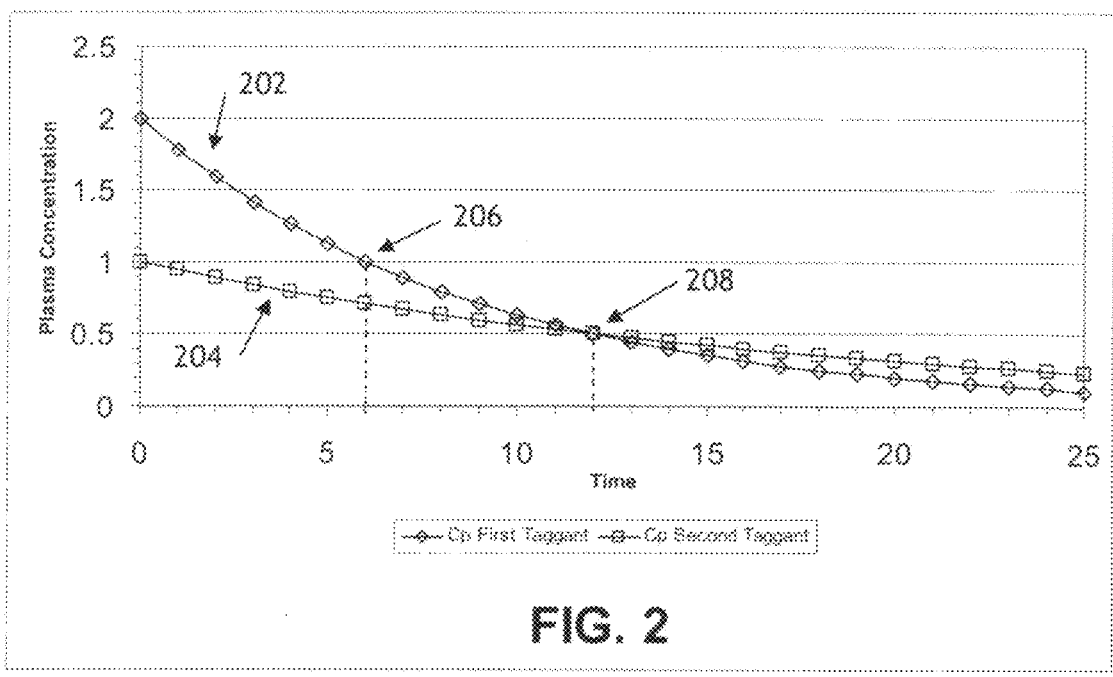
FIG. 2 is a graph illustrating the pharmacokinetic profiles for a first taggant and a second taggant.

The pharmacokinetic profile of a pharmaceutically-acceptable taggant may provide an indication of what a subject's body does to the taggant after the taggant is administered. Pharmacokinetics may be defined as the process or processes by which a therapeutic agent/pharmaceutically-acceptable taggant is absorbed, distributed, metabolized, or eliminated by the subject's body. A pharmacokinetic profile may be defined as the characteristic or characteristics of absorption, distribution, metabolization, or elimination for any particular therapeutic agent/pharmaceutically-acceptable taggant. In the present disclosure, the pharmacokinetic profile of the first pharmaceutically-acceptable taggant is different from the pharmacokinetic profile of the second pharmaceutically-acceptable taggant. One example of a pharmacokinetic profile of a taggant may be the plasma concentration over time with respect to the taggant. Example profiles are presented in FIG. 2 depicting a plasma concentration over time for the first pharmaceutically-acceptable taggant 202 and a plasma concentration over time for the second pharmaceutically-acceptable taggant 204. The first pharmaceutically-acceptable taggant in this example may have an initial plasma concentration of 2 mg/L with a half-life of 6 hours. The second pharmaceutically-acceptable taggant in this example may have an initial plasma concentration of 1 mg/L with a half-life of 12 hours. The pharmacokinetic profiles in this example indicate that the subject (body) may clear approximately half of the first pharmaceutically-acceptable taggant in about 6 hours after administering the first taggant (i.e., point 206 may be reached in about 6 hours), and the subject (body) may clear approximately half of the second pharmaceutically-acceptable taggant in about 12 hours after administering the second taggant (i.e., point 208 may be reached in about 12 hours).

The pharmacokinetic profile of the first pharmaceutically-acceptable taggant may be considered to be different from the pharmacokinetic profile of the second pharmaceutically-acceptable taggant when the half-life of the first pharmaceutically-acceptable taggant is different from the half-life of the second pharmaceutically-acceptable taggant. Further, one or more of the first taggant and the second taggant may posses a half-life less than or equal to a half-life for the therapeutic agent. Additionally, one or more of the first taggant and the second taggant may posses a half-life greater than or equal to a half-life for the therapeutic agent. Alternative parameters, such as initial concentrations or metabolic absorption rates for the first pharmaceutically-acceptable taggant and the second pharmaceutically-acceptable taggant may also differentiate the pharmacokinetic profiles of the first and second taggants. For example, if the metabolic absorption rate of the first pharmaceutically-acceptable taggant is different from the metabolic absorption rate of the second pharmaceutically-acceptable taggant, the pharmacokinetic profile of the first pharmaceutically-acceptable taggant is considered to be different from the pharmacokinetic profile of the second pharmaceutically-acceptable taggant, even if the half-lives of the two taggants are equal.

Figure 10:
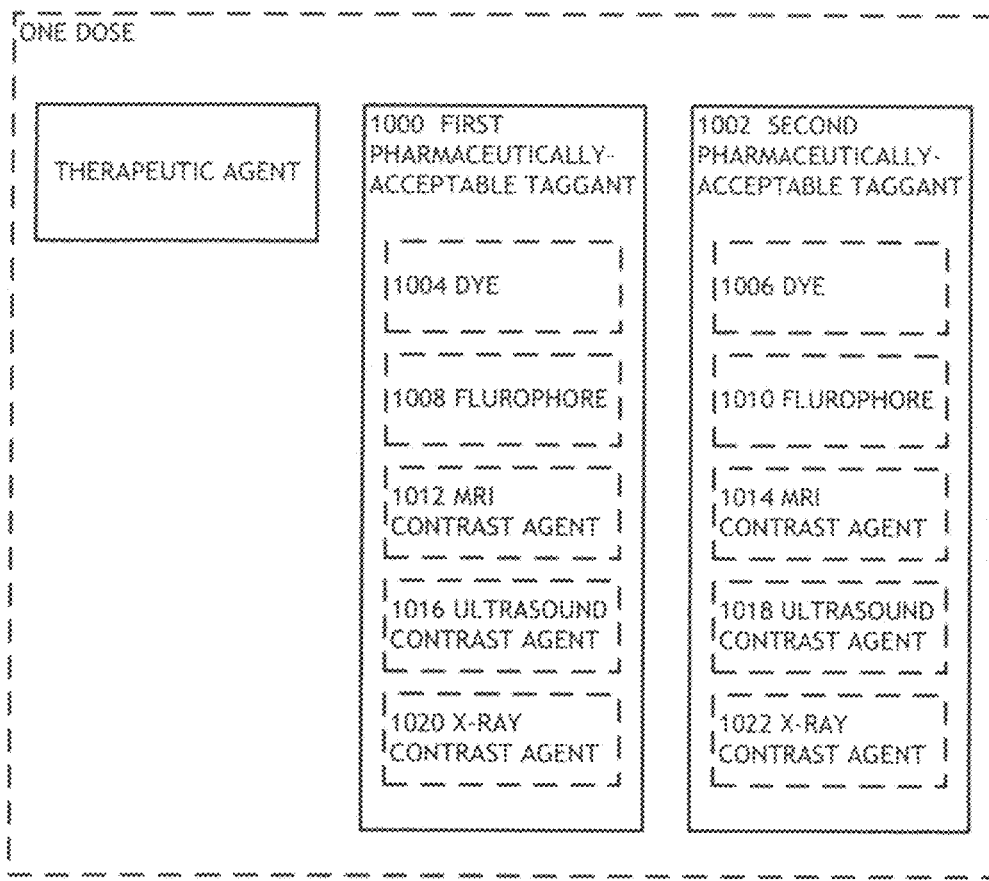
FIG. 10 is schematic of a therapeutic agent, a first taggant, and a second taggant.

Referring now to FIG. 10, one of the first pharmaceutically-acceptable taggant 1000, the second pharmaceutically-acceptable taggant 1002, or both may comprise one or more of a dye 1004 or 1006 (e.g., a pharmaceutically-acceptable acridine dye, a cyanine dye, a fluorone dye, a phenanthridine dye, or a rhodamine dye), a fluorophore 1008 or 1010 (e.g., a suitable fluorophore may include 8-aminonapthalene-l,3,6-trisulphonic acid (ANTS), 1-amino-4-naphthalene sulfonic acid (ANSA), 1-aminonapthalene-6,8-disulphonic acid (ANDA), lucifer yellow, or 2-aminoacridone), an MRI contrast agent 1012 or 1014 (e.g., a suitable MRI contrast agent may include an extracellular, Gadolinium-based agent having a relatively short residence time or an intracellular agent having a longer residence time, which may allow for extended imaging procedures without the need for repeated injections of the agent), an ultrasound contrast agent 1016 or 1018 (e.g., gas-filled microbubbles, or other commercially available cardiac or vascular ultrasound contrast agents), or an x-ray contrast agent 1020 or 1022 (e.g., compounds that may be utilized to improve the visibility of internal bodily structures in an x-ray image; a suitable x-ray contrast agent may include a barium sulfate based agent or an iodine based agent). For example, the first pharmaceutically-acceptable taggant 1000 may comprise a dye 1004 and the second pharmaceutically-acceptable taggant 1002 may comprise an MRI contrast agent 1022. In an example, the first pharmaceutically-acceptable taggant 1000 may comprise an ultrasound contrast agent 1016 while the second pharmaceutically-acceptable taggant 1002 may comprise another ultrasound contrast agent 1018 with a pharmacokinetic profile different from the ultrasound contrast agent of the first pharmaceutically-acceptable taggant 1000 (e.g., the two taggants may have different half-lives).

In one embodiment, a concentration of the first pharmaceutically-acceptable taggant or a concentration of a metabolic byproduct of the first pharmaceutically-acceptable taggant may be detected. Similarly, a concentration of the second pharmaceutically-acceptable taggant or a concentration of a metabolic byproduct of the second pharmaceutically-acceptable taggant may also be detected. Metabolic byproducts may comprise substances produced by a subject's body while metabolizing the taggant.

The concentrations of the first pharmaceutically-acceptable taggant and the second pharmaceutically-acceptable taggant may be detected utilizing various techniques. For example, a noninvasive (i.e., without cutting, incising, injecting, penetrating, or puncturing) ex vivo assay may be utilized for detecting the concentrations. The noninvasive ex vivo assay may be conducted on one or more of an expired breath of the subject with a gas-analytic device or a fluid exuded by the skin of the subject. The noninvasive ex vivo assay may also be conducted on one or more of feces, saliva, sweat, tears, hair, or urine or other body fluid of the subject. In another example, a noninvasive in vivo assay may be utilized for detecting the concentrations of the first and the second taggants. The noninvasive in vivo assay may include one or more of a transdermal measurement or a retinal measurement on the subject. The noninvasive in vivo assay may also include one or more of x-ray fluorescence, an optical fluorescence, an MRI signature, an ultrasound signature, or an x-ray signature. In still another example, a sensor may be associated with the subject for detecting the concentrations of the first pharmaceutically-acceptable taggant or the metabolic byproduct of the first pharmaceutically-acceptable taggant. Similarly, another sensor (may or may not be the same as the sensor above) may be associated with the subject for detecting the concentrations of the second pharmaceutically-acceptable taggant or the metabolic byproduct of the second pharmaceutically-acceptable taggant.

Figure 3:
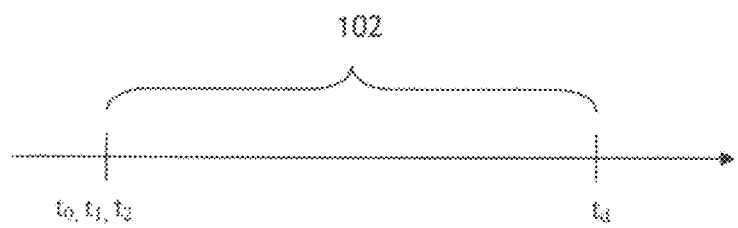
FIG. 3 is a timeline illustrating the administration of a therapeutic agent, a first taggant, and a second taggant; and the detection of the first taggant and the second taggant.

In one embodiment, a time period lapsed 102 between administering the therapeutic agent to the subject and detecting the concentration of the second taggant or metabolic byproduct of the second taggant may be approximated. One example scenario for approximating the time period lapsed is illustrated in FIG. 3. In this example scenario, the therapeutic agent, the first pharmaceutically-acceptable taggant, and the second pharmaceutically-acceptable taggant are all administered to the subject at the same time $t_0$ ($t_0$, $t_1$, and $t_2$ are equal). Subsequently, at time $t_d$, the concentration of the first taggant or the metabolic byproduct of the first taggant, and the concentration of the second taggant or the metabolic byproduct of the second taggant are detected. These measurements, in combination with the pharmacokinetic profiles for the first and second taggants are then utilized to calculate the time of administration, $t_0$.

Figure 4:
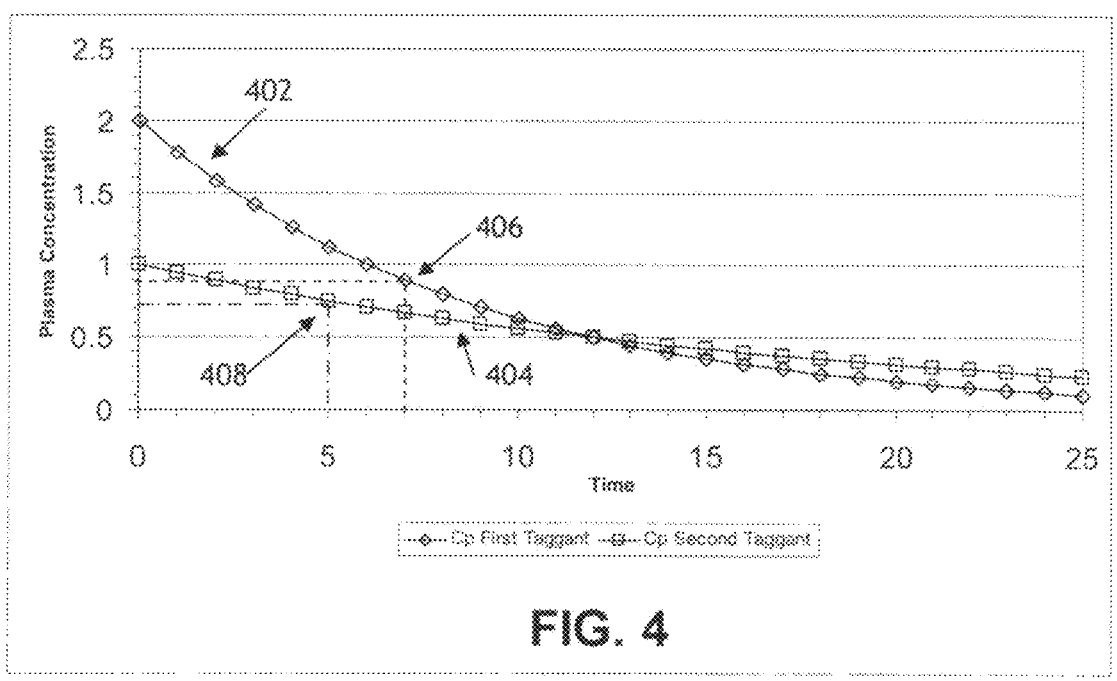
FIG. 4 is a graph illustrating the pharmacokinetic profiles for a first taggant and a second taggant.

The pharmacokinetic profiles of the first and second pharmaceutically-acceptable taggants may be expressed in terms of plasma concentrations over time, as illustrated in FIG. 4. If the detected plasma concentration of the first pharmaceutically-acceptable taggant is, for example, at least approximately 0.9 mg/L, and it is known that the first pharmaceutically-acceptable taggant has an initial plasma concentration of at least approximately 2 mg/L with a half-life of at least approximately 6 hours, then the detected plasma concentration of the first taggant may correspond to point 406 on the plasma concentration profile of the first taggant 402. The corresponding point 406 suggests that at least approximately 7 hours may have elapsed between time $t_1$ (the time that the first pharmaceutically-acceptable taggant was administered) and $t_d$. Since the first pharmaceutically-acceptable taggant was co-administered with the therapeutic agent ($t_0$ and $t_1$ are equal), the time period lapsed between $t_0$ and $t_d$ estimated based on the concentration of the first pharmaceutically-acceptable taggant may be about 7 hours.

Also illustrated in FIG. 4, if the detected plasma concentration of the second pharmaceutically-acceptable taggant is, for example, at least approximately 0.75 mg/L, and it is known that the second pharmaceutically-acceptable taggant has an initial plasma concentration of at least approximately 1 mg/L with a half-life of at least approximately 12 hours, then the detected plasma concentration of the second taggant may correspond to point 408 on the plasma concentration profile of the second taggant 404. The corresponding point 408 suggests that at least approximately 5 hours have elapsed since time $t_2$ (the time that the second pharmaceutically-acceptable taggant was administered) and $t_d$. Since the second pharmaceutically-acceptable taggant was also co-administered with the therapeutic agent in this example ($t_0$ and $t_2$ are equal), the approximated time lapsed between $t_0$ and $t_d$ estimated based on the concentration of the second pharmaceutically-acceptable taggant may be about 5 hours. The time period lapsed 102 (FIG. 3) may be calculated as an average of the time estimation based on the first taggant and the time estimation based on the second taggant. Therefore, the time period lapsed 102 in this particular example may be approximately (7+5)/2=6 hours, which suggests that the therapeutic agent was administered approximately 6 hours prior to conducting the detections at time $t_d$.

It is contemplated that a second concentration of the first taggant or metabolic byproduct of the first taggant may be detected to increase the accuracy of the approximated time period lapsed 102. For example, if the concentration detected earlier (the first concentration) is based on plasma concentration, then the second concentration may be based on an MRI contrast agent or an ultrasound contrast agent. The second concentration may also be detected relative to the first concentration. Additionally, the first concentration and the second concentration may be compared. For example, approximated time period lapsed calculated based on the first concentration detected at a first detection time may be about 5 hours. At a second detection time 1 hour subsequent to the first detection time, an approximated time period lapsed calculated based on the second concentration may be about 6.5 hours (for example, in cases where the subject may absorb a taggant more quickly than profiled data). The approximated time in this example may suggest that the duration between the first and second detection time is about 1.5 hours, while the actual duration is known to be 1 hour. In such cases, comparing the first and second concentrations may help in detecting and reducing approximation errors; for instance, by calculating an offset based on the approximated duration and the actual duration. Other comparing methods may include, but are not limited to, digital signal processing or Fourier analysis. Similarly, a second concentration of the second taggant or metabolic byproduct of the second taggant may also be detected. It is further contemplated that the concentrations of the first and second taggants or the concentrations of metabolic byproducts of the first and second taggants may be detected intermittently.

Figure 5:
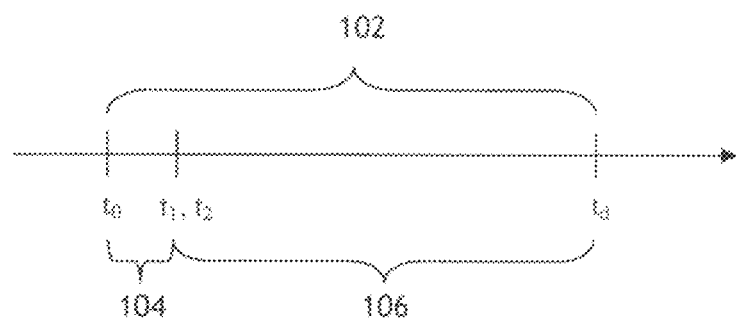
FIG. 5 is a timeline illustrating the administration of a therapeutic agent, a first taggant, and a second taggant; and the detection of the first taggant and the second taggant.

Another example of approximating the time period lapsed 102 is illustrated in FIG. 5. In this example scenario, the therapeutic agent is administered to the subject at time $t_0$. The first pharmaceutically-acceptable taggant and the second pharmaceutically-acceptable taggant may be co-administered to the subject at time $t_1$ ($t_1$ and $t_2$ are equal), subsequent to time $t_0$. A time interval 104 starting when the therapeutic agent is administered to the subject and ending when the first pharmaceutically-acceptable taggant is administered to the subject (time interval between $t_0$ and $t_1$) may be known. For example, the therapeutic agent, the first taggant and the second taggant may enter the subject in the same dosage form (e.g., as a single pill). The subject may start absorbing the therapeutic agent directly, while the first and second taggant may comprise a protective coating (e.g., an enteric coating) to delay the release of the taggants to the subject until 30 minutes after the subject started absorbing the therapeutic agent. In this example, the time interval 104 is equal to 30 minutes. In another example, the therapeutic agent may be administered to the subject via nasal inhalation, while the first and second taggant may be administered to the subject orally. In such cases, the subject may not be able to accomplish both administering processes simultaneously, and the subject may configure/specify the time interval 104 to reflect the time lapsed between the time the therapeutic agent is administered and the time the first pharmaceutically-acceptable taggant is administered.

Subsequently, at time $t_d$, the concentration of the first taggant or the metabolic byproduct of the first taggant may be detected. The detected concentration may be utilized to estimate the time lapsed between administering (time $t_1$) and detecting (time $t_d$) the first pharmaceutically-acceptable taggant (as previously described). Similarly, the concentration of the second taggant or the metabolic byproduct of the second taggant may also be detected at time $t_d$. The detected concentration may be utilized to estimate the time lapsed between administering (time $t_2$) and detecting (time $t_d$) the second pharmaceutically-acceptable taggant (as previously described). The estimated time lapsed calculated based on the first pharmaceutically-acceptable taggant (estimated time lapsed from $t_1$ to $t_d$) and the second pharmaceutically-acceptable taggant (estimated time lapsed from $t_2$ to $t_d$) may be utilized to approximate a second time period lapsed 106.

The second time period lapsed 106 represents a time period lapsed between administering the first taggant and detecting the concentration of the second taggant or the metabolic byproduct of the second taggant. For example, the time lapsed estimated based on the first pharmaceutically-acceptable taggant may be about 7 hours, and the time lapsed estimated based on the second pharmaceutically-acceptable taggant may be about 5 hours. In the example illustrated in FIG. 5, where the first taggant is co-administered with the second taggant ($t_1$ equals $t_2$), the second time period lapsed 106 may be calculated as an average of the estimation based on the first taggant and the estimation based on the second taggant. In this example, the second time period lapsed 106 may be approximately 6 hours. The time period lapsed 102 overall in this example may be calculated as the time interval 104 (30 minutes) plus the second time period lapsed 106 (6 hours), indicating that the therapeutic agent was administered approximately 6.5 hours prior to conducting the detections at time $t_d$.

Figure 6:
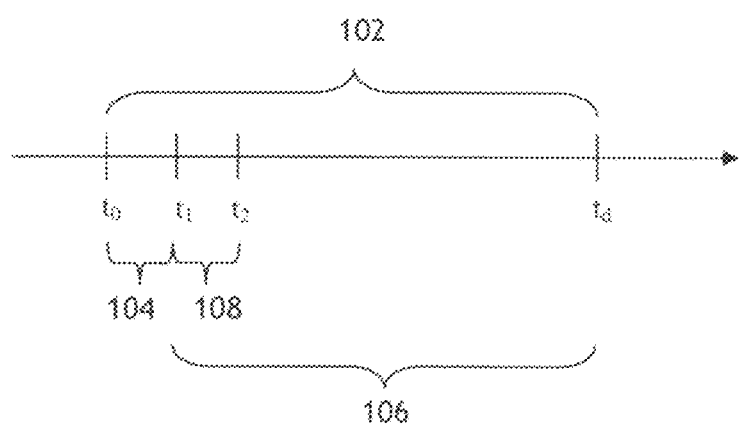
FIG. 6 is a timeline illustrating the administration of a therapeutic agent, a first taggant, and a second taggant; and the detection of the first taggant and the second taggant.

An additional example of approximating the time period lapsed 102 is illustrated in FIG. 6. In this example scenario, the therapeutic agent is administered to the subject at time $t_0$. The first pharmaceutically-acceptable taggant is administered subsequently at time $t_1$, and the second pharmaceutically-acceptable taggant is administered subsequently at time $t_2$. A time interval 104 starting when the therapeutic agent is administered to the subject and ending when the first pharmaceutically-acceptable taggant is administered to the subject may be known (as previously described). A second interval 108 starting when the first taggant is administered to the subject and ending when the second taggant is administered to the subject may be known as well. For example, the first taggant and the second taggant may enter the subject in the same dose (e.g., in a single pill). The subject may start absorbing the first taggant directly, while the second taggant may comprise a protective coating which delays the release until 15 minutes after the subject started absorbing the first taggant. In this example, the second interval 108 is equal to 15 minutes. In another example, the first taggant may be administered to the subject via nasal inhalation, while the second taggant may be administered to the subject orally. In such cases, the subject may not be able to accomplish both administering processes simultaneously, and the subject may configure/specify the second interval 108 to reflect this time difference.

Subsequently, at time $t_d$, the concentration of the first taggant or the metabolic byproduct of the first taggant may be detected. The detected concentration may be utilized to estimate the time lapsed between administering the first pharmaceutically-acceptable taggant (time $t_1$) and detecting the concentration. Similarly, the concentration of the second taggant or the metabolic byproduct of the second taggant may also be detected at time $t_d$. The detected concentration may be utilized to estimate the time lapsed between administering the second pharmaceutically-acceptable taggant (time $t_2$) and detecting of the concentration. The estimated time lapsed calculated based on the first pharmaceutically-acceptable taggant (estimated time lapsed from $t_1$ to $t_d$) and the second pharmaceutically-acceptable taggant (estimated time lapsed from $t_2$ to $t_d$) may be utilized to approximate the second time period lapsed 106.

The second time period lapsed 106 represents a time period lapsed between administering the first taggant and detecting the concentration of the second taggant or the metabolic byproduct of the second taggant. In the example illustrated in FIG. 6, since the second taggant is administered subsequent to the first taggant, the second interval 108 may need to be added to the estimated time period between $t_2$ and $t_d$ to more accurately approximate the second time period lapsed 106. For example, the estimated time period from administering the first taggant to the detecting process (time period between $t_1$ and $t_d$) may be about 7 hours, and the estimated time period from administering the second taggant to the detecting process (time period between $t_2$ and $t_d$) may be about 5 hours. However, if the second taggant is administered 15 minutes after administering the first taggant (e.g., when the second interval 108 is 15 minutes), 15 minutes may be added to the time elapsed between $t_2$ and $t_d$. Therefore, the second time period lapsed estimated based on the second taggant may be 5 hours and 15 minutes. The average of the estimation based on the first taggant and the estimation based on the second taggant may then be calculated to approximate the second time period lapsed 106. Therefore, the second time period lapsed 106 in this particular example may be calculated as (7+5.25)/2=6.125 hours. Further, as FIG. 6 illustrates, the time period lapsed 102 overall in this example may be calculated as the time interval 104 (30 minutes for example) plus the second time period lapsed 106 (6.125 hours in this example), indicating that the therapeutic agent was administered approximately 6.625 hours prior to conducting the detections at time $t_d$.

Figure 7:
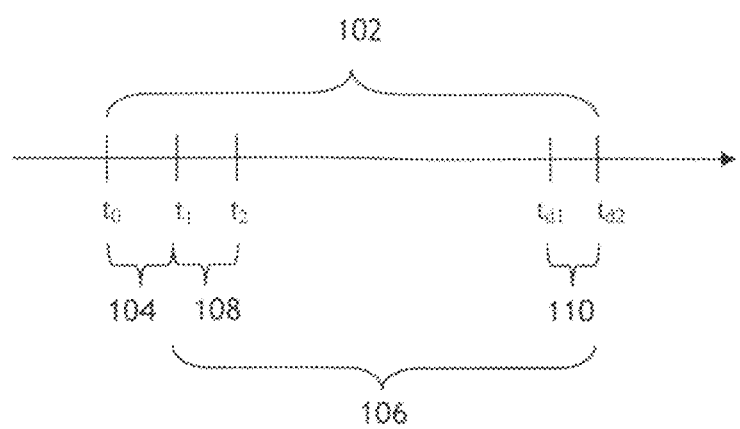
FIG. 7 is a timeline illustrating the administration of a therapeutic agent, a first taggant, and a second taggant; and the detection of the first taggant and the second taggant.

Still another example of approximating the time period lapsed 102 is illustrated in FIG. 7. In this example scenario, the therapeutic agent is administered to the subject at time $t_0$. The first pharmaceutically-acceptable taggant is administered subsequently at time $t_1$, and the second pharmaceutically-acceptable taggant is administered subsequently at time $t_2$. A time interval 104 starting when the therapeutic agent is administered to the subject and ending when the first pharmaceutically-acceptable taggant is administered to the subject may be known (as previously described). A second interval 108 starting when the first taggant is administered to the subject and ending when the second taggant is administered to the subject may be known as well (as previously described).

Subsequently, at time $t_{d1}$, the concentration of the first taggant or the metabolic byproduct of the first taggant may be detected. The detected concentration may be utilized to estimate the time lapsed between administering the first pharmaceutically-acceptable taggant (time $t_1$) and time $t_{d1}$. The concentration of the second taggant or the metabolic byproduct of the second taggant may be detected subsequent to $t_{d1}$. For example, the second taggant or the metabolic byproduct of the second taggant may be detected utilizing a different process conducted at a subsequent time $t_{d2}$ (e.g., 6 minutes after $t_{d1}$). The time period lapsed between $t_{d1}$ and $t_{d2}$ may be a known period 110. The detected concentration of the second taggant or the metabolic byproduct of the second taggant may be utilized to estimate the time lapsed between administering the second pharmaceutically-acceptable taggant (time $t_2$) and time $t_{d2}$. The second interval 108, the known period 110, the estimated time lapsed between $t_1$ and $t_{d1}$, and the estimated time lapsed between $t_2$ and $t_{d2}$ may be utilized to approximate the second time period lapsed 106.

The second time period lapsed 106 represents a time period lapsed between administering the first taggant (time $t_1$) and detecting the concentration of the second taggant or the metabolic byproduct of the second taggant (represented as time $t_{d2}$ in FIG. 7). In the example illustrated in FIG. 7, to better approximate the second time period lapsed 106 based on the first taggant, the known period 110 may be added to the estimated time period from time $t_1$ to $t_{d1}$. For example, if the estimated time period from time $t_1$ to $t_{d1}$ is 7 hours, and the known period 110 is about 6 minutes, then the second time period lapsed approximated based on the first taggant may be 7 hours and 6 minutes.

Also illustrated in FIG. 7, if the second taggant is administered 15 minutes after administering the first taggant (the second interval 108 equals 15 minutes), and the estimated time period between $t_2$ and $t_{d2}$ is about 5 hours, then the second interval 108 may need to be added to the estimated time period between $t_2$ and $t_{d2}$ to more accurately approximate the second time period lapsed. Therefore, in this example, the second time period lapsed 106 estimated based on the second taggant may be 5 hours and 15 minutes. The average of the estimation based on the first taggant and the estimation based on the second taggant may be calculated to approximate the second time period lapsed 106. Therefore, the second time period lapsed 106 in this particular example may be calculated as (7.1+5.25)/2=6.175 hours. Further, as FIG. 7 illustrates, the time period lapsed 102 overall in this example may be calculated as the time interval 104 (30 minutes for this example) plus the second time period lapsed 106 (6.175 hours in this example), indicating that the therapeutic agent was administered approximately 6.675 hours prior to detecting at time $t_{d2}$.

Figure 8:
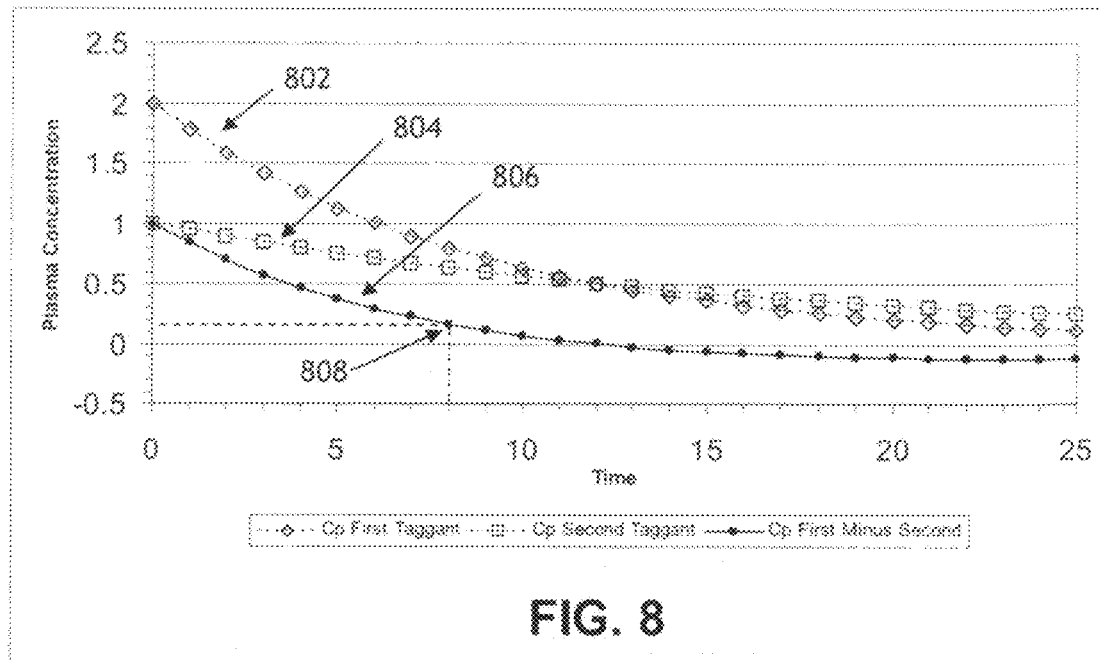
FIG. 8 is a graph illustrating the relative pharmacokinetic profiles for a first taggant and a second taggant.
Figure 9:
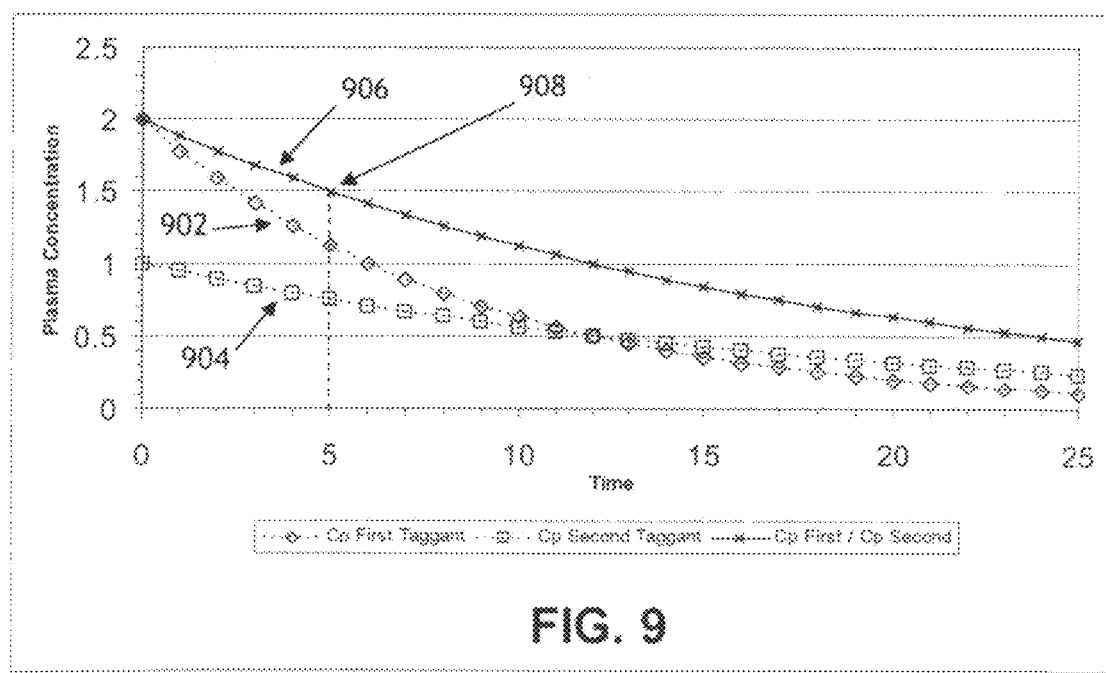
FIG. 9 is a graph illustrating the relative pharmacokinetic profiles for a first taggant and a second taggant.

Referring now to FIGS. 8 and 9, the level of the first taggant may be measured relative to the level of the second taggant. This may be desirable when an amount of the first taggant (or a metabolic byproduct thereof) interacts with an amount of the second taggant (or a metabolic byproduct thereof), with the potential effect that only a relative measurement of either taggant may be available or easily obtainable. For instance, a byproduct of the first taggant may absorb a portion of the second taggant. In this instance, it may be desirable to measure how much more of the first taggant is present over the second taggant (e.g., measuring a concentration of the first taggant minus the second taggant). In another example, measurement of one or both of the first and second taggants may only be possible when the relative level of one to another is within a certain range. For example, the first taggant may produce a luminous effect in the eye of a subject when there is at least approximately twice as much of the first taggant as the second taggant (e.g., the ratio of a concentration of the first taggant to the second taggant is measured). In such instances, it may be beneficial to detect a level of the first taggant or a metabolic byproduct of the first taggant relative to a level of the second taggant or a metabolic byproduct of the second taggant. In one embodiment, the relative levels detected may be compared to a relative pharmacokinetic profile for approximating the time period lapsed between administering the therapeutic agent to the subject and detecting the relative levels.

FIG. 8 presents an example depicting a relative pharmacokinetic profile 806 of the first and the second taggants obtained by subtracting the pharmacokinetic profile of the second taggant 804 from the pharmacokinetic profile of the first taggant 802. For instance, if the detected plasma level based on the first taggant minus the detected plasma level based on the second taggant is about 0.16 mg/L, the difference may correspond to point 808, which suggest that about 8 hours may have elapsed since administering the first taggant. In this manner, the time period lapsed may be approximated by detecting differences between concentrations of the first and second taggants or their metabolic byproducts.

FIG. 9 presents another example depicting a relative pharmacokinetic profile 906 of the first and the second taggants obtained by dividing the pharmacokinetic profile of the first taggant 902 by the pharmacokinetic profile of the second taggant 904. For instance, if the detected level of the first taggant divided by the detected level of the second taggant is about 1.5 (i.e., the detected level of the first taggant is about 50% more than the detected level of the second taggant), then the relative relation may correspond to point 908, which suggests that about 5 hours may have elapsed since administering the first taggant. In this manner, the time period lapsed may be approximated by detecting a ratio of the first taggant divided by the second taggant.

It is understood that if the first pharmaceutically-acceptable taggant is administered to the subject subsequent to the therapeutic agent, a time interval (as previously described) may be added to time period lapsed between administering the first pharmaceutically-acceptable taggant to the subject and detecting the relative levels. For example, based on the relative pharmacokinetic profile, if the relative levels of the first and second taggant suggests that about 5 hours may have elapsed, and it is known that the first taggant is administered 30 minutes after administering the therapeutic agent (time interval is 30 minutes), then the time period lapsed overall may be approximated by adding the time interval to the time period lapsed between administering the first taggant and detecting the relative levels (a second time period lapsed), indicating that the therapeutic agent was administered approximately 5.5 hours prior to detecting the relative levels.

It is contemplated that alternative representations of relative levels, in addition to subtraction and division, may be utilized to express relationships of the first taggant and the second taggant. For example, the relative pharmacokinetic profile of the first and second taggants may be additive or multiplicative. It is also contemplated that additional levels of the first taggant or one or more metabolic byproducts of the first taggant relative to the second taggant or one or more metabolic byproducts of the second taggant may be detected. In one embodiment, a second level of the first taggant or a metabolic byproduct of the first taggant relative to a second level of the second taggant or a metabolic byproduct of the second taggant is detected to increase the accuracy of the time estimation as described above.

The level of the first pharmaceutically-acceptable taggant or metabolic byproduct of the first pharmaceutically-acceptable taggant relative to the level of the second pharmaceutically-acceptable taggant or metabolic byproduct of the second pharmaceutically-acceptable taggant may be detected utilizing various methods. For example, a noninvasive ex vivo assay may be utilized for detecting the relative levels. The noninvasive ex vivo assay may be conducted on one or more of an expired breath of the subject with a gas-analytic device or a fluid exuded by the skin of the subject. The noninvasive ex vivo assay may also be conducted on one or more of sweat, saliva, tears, feces, hair, or urine of the subject. In another example, a noninvasive in vivo assay may be utilized for detecting the relative levels of the first and the second taggants. The noninvasive in vivo assay may include one or more of a transdermal measurement or a retinal measurement on the subject. The noninvasive in vivo assay for detecting at least one of the first pharmaceutically-acceptable taggant or the second pharmaceutically-acceptable taggant may include one or more of x-ray fluorescence, an optical fluorescence, an MRI signature, an ultrasound signature, or an x-ray signature.

It is contemplated that a sensor may be associated with the subject for detecting the level of the first pharmaceutically-acceptable taggant relative to the level of the second pharmaceutically-acceptable taggant, or for detecting the level of a metabolic byproduct of the first pharmaceutically-acceptable taggant relative to the level of a metabolic byproduct of the second pharmaceutically-acceptable taggant. It is also contemplated that the relative levels of the first pharmaceutically-acceptable taggant and the second pharmaceutically-acceptable taggant, or the relative levels of the metabolic byproduct of the first pharmaceutically-acceptable taggant and the metabolic byproduct of the second pharmaceutically-acceptable taggant, may be detected intermittently.

For example, a second relative level of the first taggant and the second taggant, or relative level of metabolic byproduct of the first taggant and metabolic byproduct of the second taggant may be detected. For instance, if the relative level detected earlier (the first relative level) is based on plasma concentration, then the second relative level may be based on an MRI contrast agent or an ultrasound contrast agent. The second relative level may also be compared to the first relative level. For instance, an approximated time period lapsed calculated based on the first relative level detected at a first detection time may be about 5 hours. At a second detection time 1 hour subsequent to the first detection time, an approximated time period lapsed is calculated based on the second relative level and may be about 6.5 hours. The approximated time in this example may suggest that the duration between the first and second detection time is about 1.5 hours, while the actual duration is known to be 1 hour. In such cases, comparing the first and second relative levels may help in detecting and reducing approximation errors, for instance, by calculating an offset based on the approximated duration and the actual duration. Other comparing methods may include, but not limited to, digital signal processing or Fourier analysis.

The time period lapsed approximated by the present disclosure may be utilized to estimate the time when the therapeutic agent was administered to the subject. In one embodiment, the time period lapsed may be utilized for determining adherence of the subject to a therapy model, also known as a treatment regimen. For example, a health practitioner may determine adherence of a patient (subject) to the therapy model based on the approximated time (the actual time when the therapeutic agent was administered may not available). Further, a signal regarding whether the subject is in compliance or non-compliance to the therapy model may be provided. The signal may be provided to, for example, one or more of the subject, a guardian, a legal representative, or a health care provider. In one embodiment, a module for communicating information to a user indicative of the time period lapsed between administering the therapeutic agent to the subject and detecting the concentration of the at least one of the second pharmaceutically-acceptable taggant or the metabolic byproduct of the second pharmaceutically-acceptable taggant may be provided. The module may comprise a text message, an email, a voice message, a voicemail, an alarm (such as an alarm provided by a device worn by the subject), a wireless transmission, as well as a number of different audio, visual, and tactile signals.

The approximated time when the therapeutic agent was administered may also be utilized for indicating when it is appropriate for additional therapeutic agent to be administered pursuant to a therapy model. For example, if a therapy model requires the therapeutic agent to be administered to the subject every 8 hours, the subject may be notified when it is determined that the last time the therapeutic agent was administered was about 8 hours ago. Alternatively, a signal may be provided when a predetermined amount of time has lapsed since the time at which the therapeutic agent was administered to the subject.

It will be appreciated that while the present disclosure describes the detection of a first and second taggant, these descriptions are meant to be explanatory only and not restrictive of the present disclosure. Thus, the present disclosure does not preclude the utilization of more than two taggants. Moreover, it is contemplated that more than two taggant may be utilized for increasing the accuracy of the time period determinations as described herein, as well as any other determination which depend on comparing taggant levels to their pharmacokinetic profiles.

Following are a series of flowcharts depicting implementations. For ease of understanding, the flowcharts are organized such that the initial flowcharts present implementations via an example implementation and thereafter the following flowcharts present alternate implementations and/or expansions of the initial flowchart(s) as either sub-component operations or additional component operations building on one or more earlier-presented flowcharts. Those having skill in the art will appreciate that the style of presentation utilized herein (e.g., beginning with a presentation of a flowchart(s) presenting an example implementation and thereafter providing additions to and/or further details in subsequent flowcharts) generally allows for a rapid and easy understanding of the various process implementations. In addition, those skilled in the art will further appreciate that the style of presentation used herein also tends itself well to modular and/or object-oriented program design paradigms.

Figure 11:
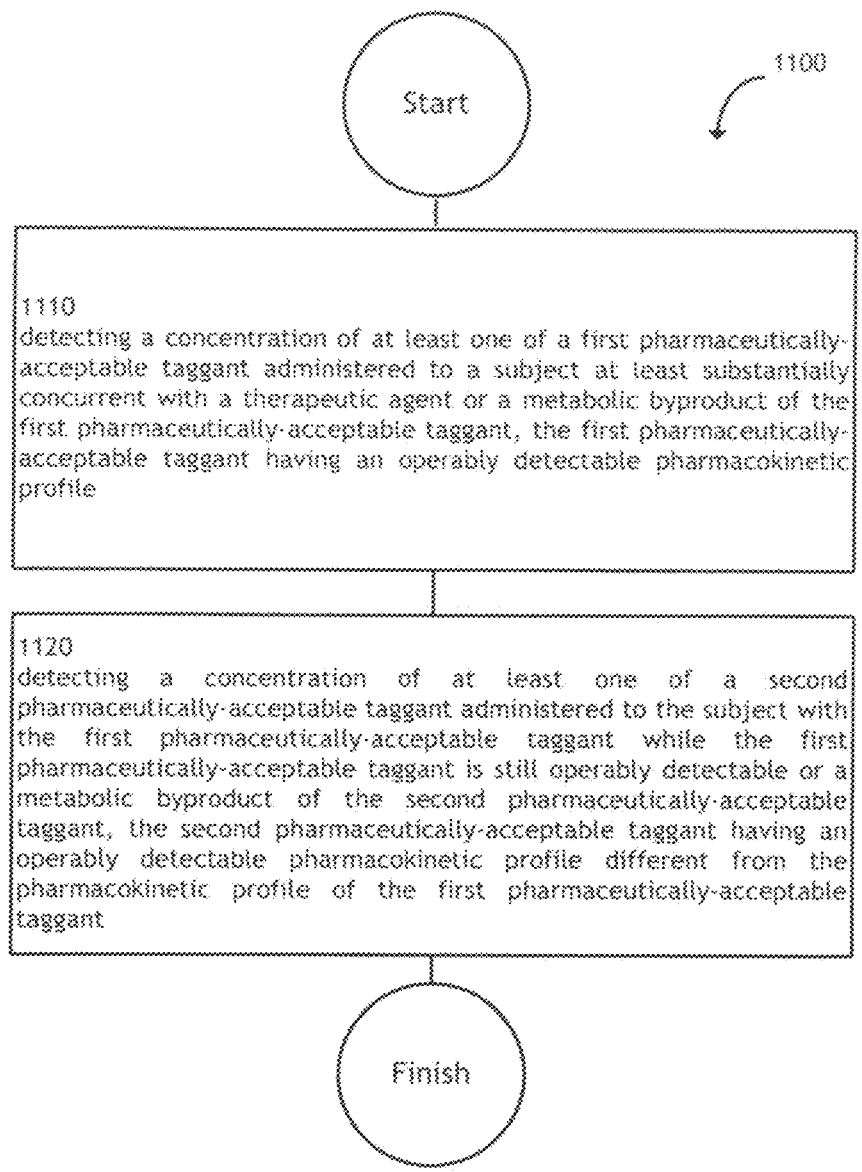
FIG. 11 illustrates an operational flow representing example operations related to detecting concentrations for a first pharmaceutically-acceptable taggant and a second pharmaceutically-acceptable taggant administered to a subject.

FIG. 11 illustrates an operational flow 1100 representing example operations related to detecting concentrations for a first pharmaceutically-acceptable taggant and a second pharmaceutically-acceptable taggant administered to the subject. In FIG. 11 and in following figures that include various examples of operational flows, discussion and explanation may be provided with respect to the above-described examples of FIGS. 1 through 10, and/or with respect to other examples and contexts. However, it should be understood that the operational flows may be executed in a number of other environments and contexts, and/or in modified versions of FIGS. 1 through 10. Also, although the various operational flows are presented in the sequence(s) illustrated, it should be understood that the various operations may be performed in other orders than those which are illustrated, or may be performed concurrently.

After a start operation, the operational flow 1100 moves to an operation 1110. Operation 1110 depicts detecting a concentration of at least one of a first pharmaceutically-acceptable taggant administered to a subject at least substantially concurrent with a therapeutic agent or a metabolic byproduct of the first pharmaceutically-acceptable taggant, the first pharmaceutically-acceptable taggant having an operably detectable pharmacokinetic profile. For example, as shown in FIGS. 1 through 10, a concentration for the first pharmaceutically-acceptable taggant is detected at time $t_{d1}$.

Then, operation 1120 depicts detecting a concentration of at least one of a second pharmaceutically-acceptable taggant administered to the subject with the first pharmaceutically-acceptable taggant while the first pharmaceutically-acceptable taggant is still operably detectable or a metabolic byproduct of the second pharmaceutically-acceptable taggant, the second pharmaceutically-acceptable taggant having an operably detectable pharmacokinetic profile different from the pharmacokinetic profile of the first pharmaceutically-acceptable taggant. For example, as shown in FIGS. 1 through 10, a concentration for the second pharmaceutically-acceptable taggant is detected at time $t_{d2}$.

Figure 12:
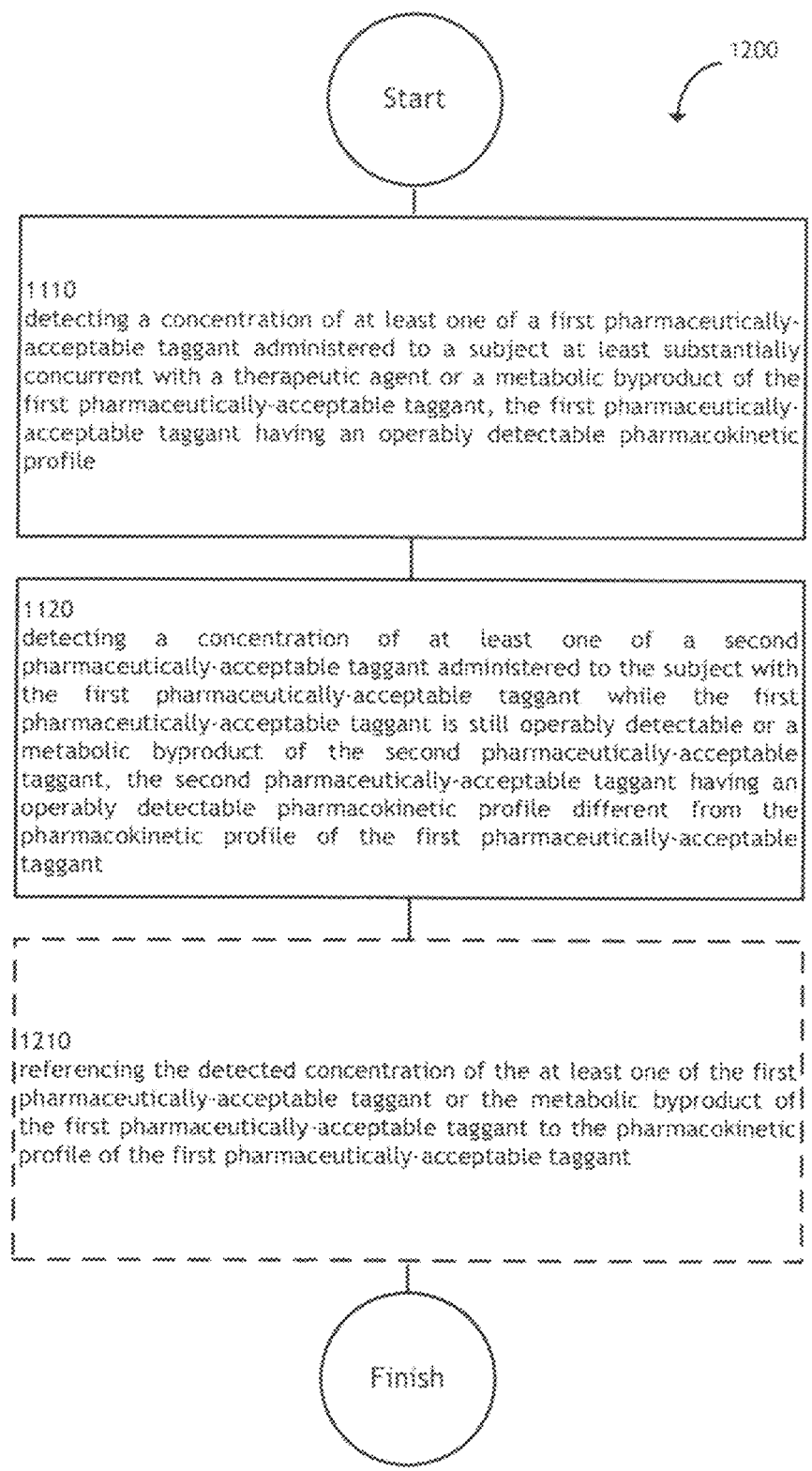
FIG. 12 illustrates an operational flow representing example operations related to referencing a detected concentration for a first pharmaceutically-acceptable taggant to its pharmacokinetic profile.

FIG. 12 illustrates an operational flow 1200 representing example operations related to referencing a detected concentration for a first pharmaceutically-acceptable taggant to its pharmacokinetic profile. FIG. 12 illustrates an example embodiment where the example operational flow 1100 of FIG. 11 may include at least one additional operation. Additional operations may include an operation 1210.

After a start operation, an operation 1110, and an operation 1120, the operational flow 1200 moves to an operation 1210. Operation 1210 illustrates referencing the detected concentration of the at least one of the first pharmaceutically-acceptable taggant or the metabolic byproduct of the first pharmaceutically-acceptable taggant to the pharmacokinetic profile of the first pharmaceutically-acceptable taggant. For example, as shown in FIGS. 1 through 10, the detected concentration for the first taggant may be referenced to a point 406 on a plasma concentration profile comprising a pharmacokinetic profile for the first taggant.

Figure 13:
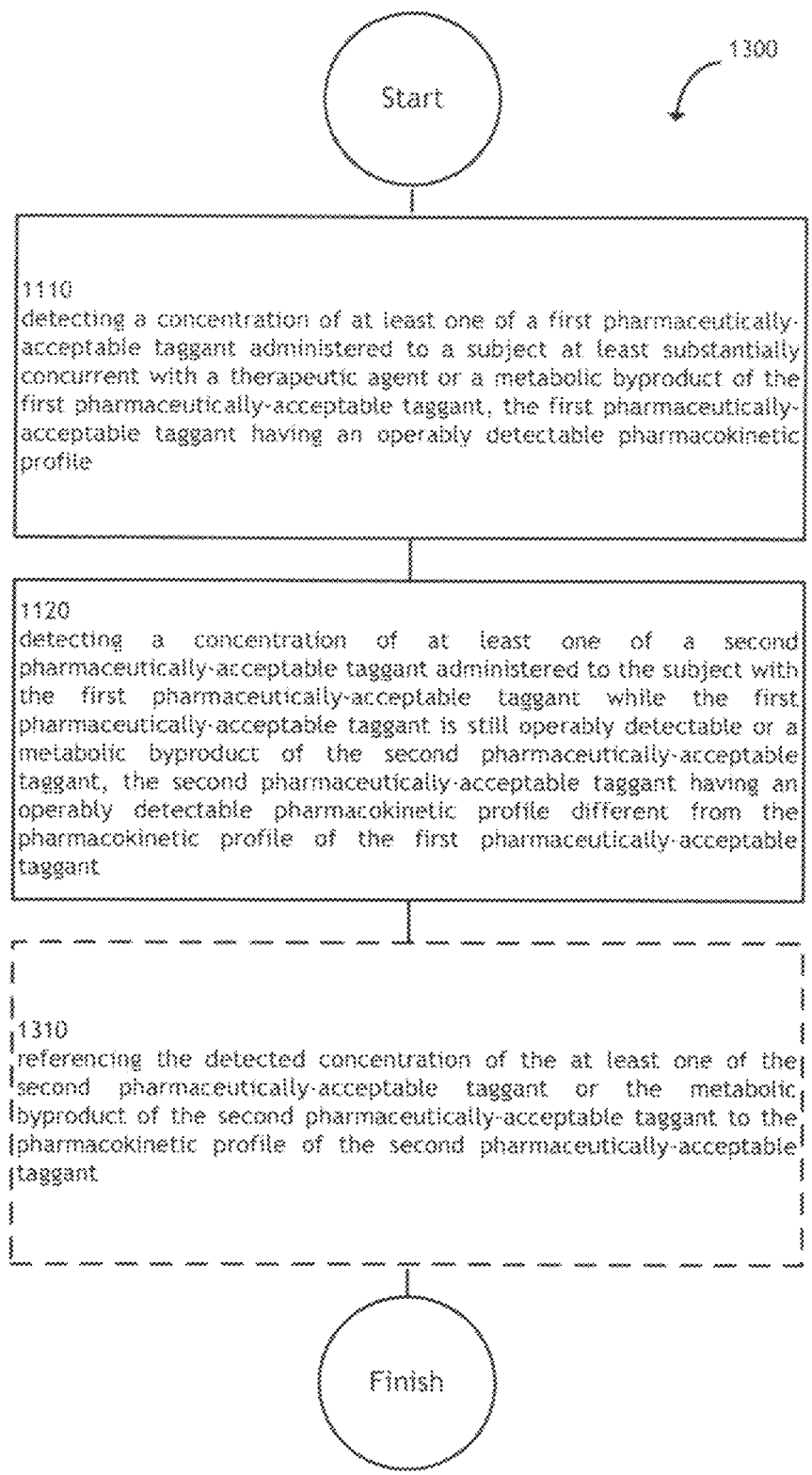
FIG. 13 illustrates an operational flow representing example operations related to referencing a detected concentration for a second pharmaceutically-acceptable taggant to its pharmacokinetic profile.

FIG. 13 illustrates an operational flow 1300 representing example operations related to referencing a detected concentration for a second pharmaceutically-acceptable taggant to its pharmacokinetic profile. FIG. 13 illustrates an example embodiment where the example operational flow 1100 of FIG. 11 may include at least one additional operation. Additional operations may include an operation 1310.

After a start operation, an operation 1110, and an operation 1120, the operational flow 1300 moves to an operation 1310. Operation 1310 illustrates referencing the detected concentration of the at least one of the second pharmaceutically-acceptable taggant or the metabolic byproduct of the second pharmaceutically-acceptable taggant to the pharmacokinetic profile of the second pharmaceutically-acceptable taggant. For example, as shown in FIGS. 1 through 10, the detected concentration for the second taggant may be referenced to a point 408 on a plasma concentration profile comprising a pharmacokinetic profile for the second taggant.

Figure 14:
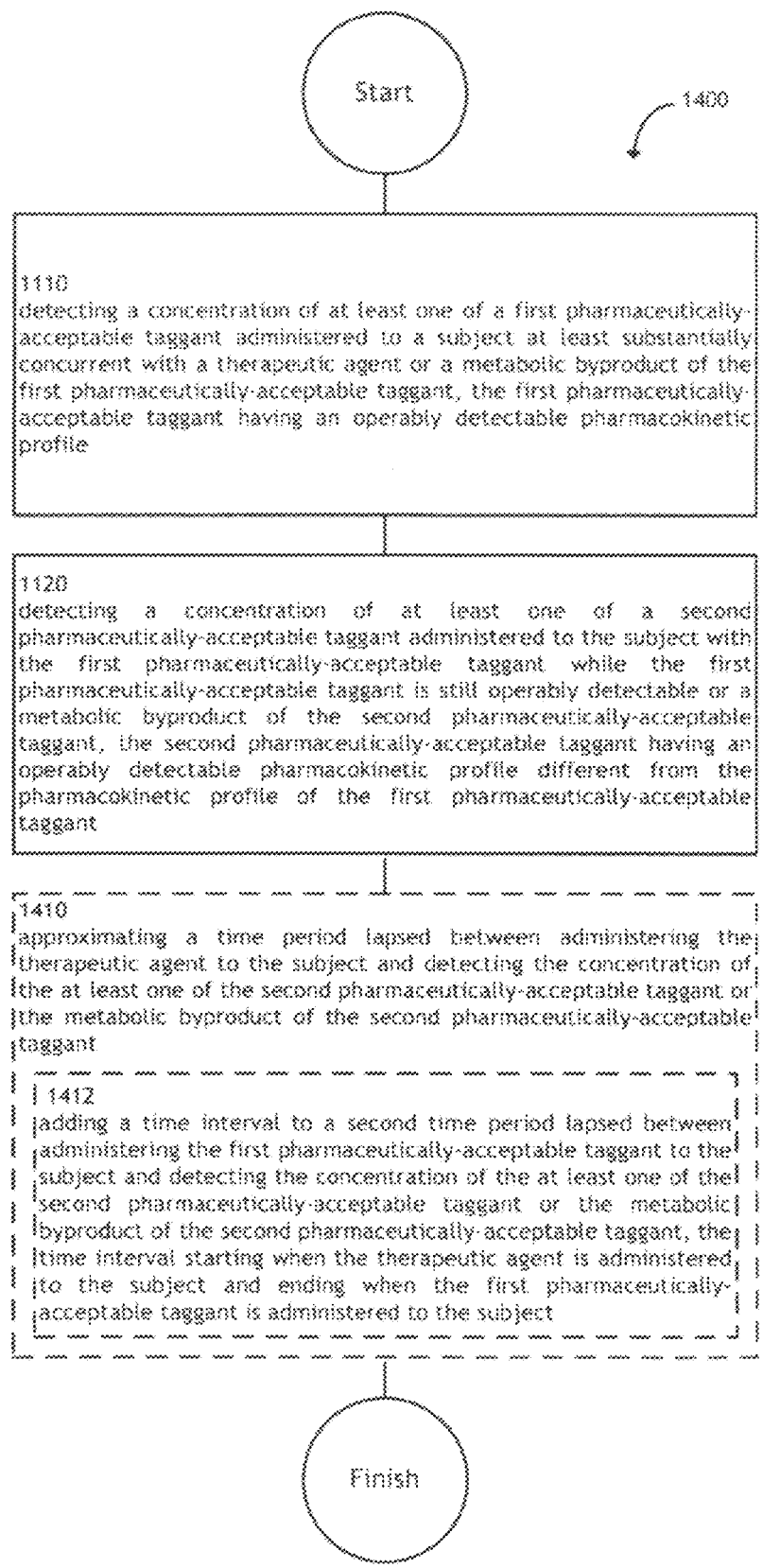
FIG. 14 illustrates an operational flow representing example operations related to determining a time period lapsed between administering a therapeutic agent to a subject and detecting concentrations for a first pharmaceutically-acceptable taggant and a second pharmaceutically-acceptable taggant administered to the subject.

FIG. 14 illustrates an operational flow 1400 representing example operations related to determining a time period lapsed between administering a therapeutic agent to a subject and detecting concentrations for a first pharmaceutically-acceptable taggant and a second pharmaceutically-acceptable taggant administered to the subject. FIG. 14 illustrates an example embodiment where the example operational flow 1100 of FIG. 11 may include at least one additional operation. Additional operations may include an operation 1410, and/or an operation 1412.

After a start operation, an operation 1110, and an operation 1120, the operational flow 1400 moves to an operation 1410. Operation 1410 illustrates approximating a time period lapsed between administering the therapeutic agent to the subject and detecting the concentration of the at least one of the second pharmaceutically-acceptable taggant or the metabolic byproduct of the second pharmaceutically-acceptable taggant. For example, as shown in FIGS. 1 through 10, the time period lapsed 102 may be approximated based on detected concentrations for the first taggant and the second taggant taken at time $t_d$.

The operation 1412 illustrates adding a time interval to a second time period lapsed between administering the first pharmaceutically-acceptable taggant to the subject and detecting the concentration of the at least one of the second pharmaceutically-acceptable taggant or the metabolic byproduct of the second pharmaceutically-acceptable taggant, the time interval starting when the therapeutic agent is administered to the subject and ending when the first pharmaceutically-acceptable taggant is administered to the subject. For example, as shown in FIGS. 1 through 10, a time interval 104 starting when the therapeutic agent is administered to a subject and ending when the first taggant is administered may be added to a time period lapsed 106, starting when the first taggant is administered and ending when the concentration for the second taggant is detected.

Figure 15:
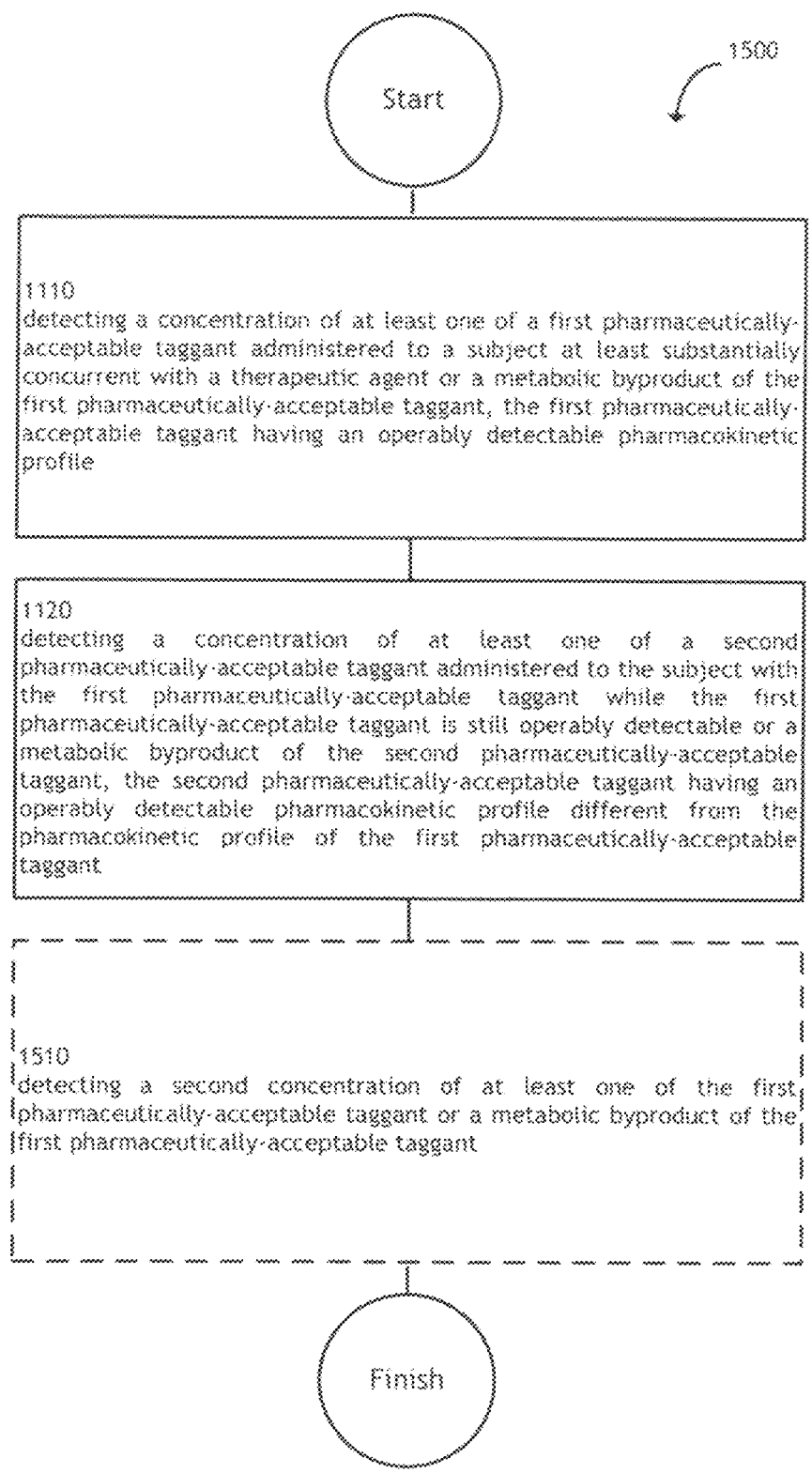
FIG. 15 illustrates an operational flow representing example operations related to detecting a first concentration and a second concentration for a first pharmaceutically-acceptable taggant administered to the subject.

FIG. 15 illustrates an operational flow 1500 representing example operations related to detecting a first concentration and a second concentration for a first pharmaceutically-acceptable taggant administered to the subject. FIG. 15 illustrates an example embodiment where the example operational flow 1100 of FIG. 11 may include at least one additional operation. Additional operations may include an operation 1510.

After a start operation, an operation 1110, and an operation 1120, the operational flow 1500 moves to an operation 1510. Operation 1510 illustrates detecting a second concentration of at least one of the first pharmaceutically-acceptable taggant or a metabolic byproduct of the first pharmaceutically-acceptable taggant. For example, as shown in FIGS. 1 through 10, a second concentration of the first taggant may be detected based on an MRI contrast agent subsequent to detecting a first concentration utilizing a plasma concentration.

Figure 16:
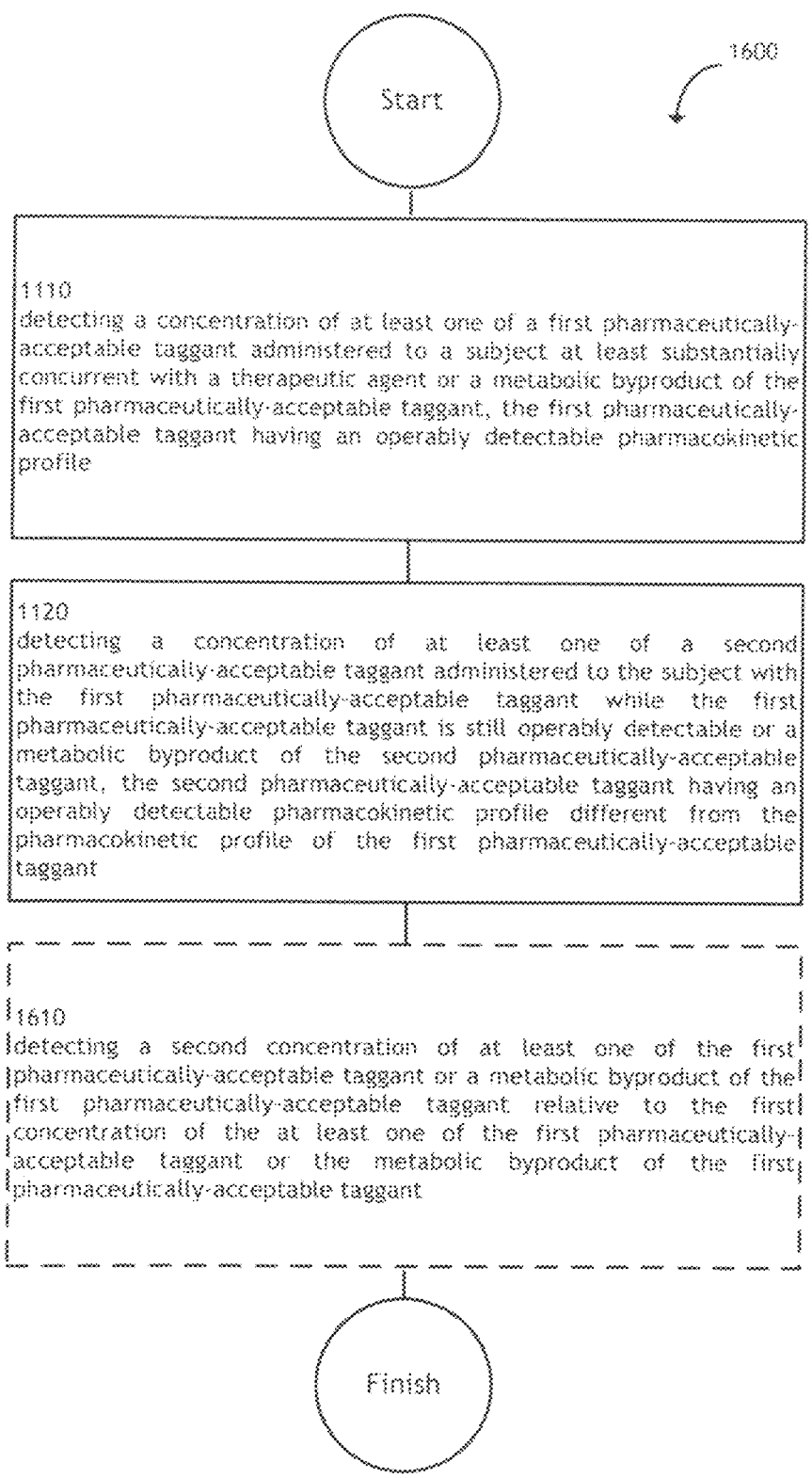
FIG. 16 illustrates an operational flow representing example operations related to determining a time period lapsed between administering a therapeutic agent to a subject and detecting concentrations for a first pharmaceutically-acceptable taggant and a second pharmaceutically-acceptable taggant administered to the subject.

FIG. 16 illustrates an operational flow 1600 representing example operations related to determining a time period lapsed between administering a therapeutic agent to a subject and detecting concentrations for a first pharmaceutically-acceptable taggant and a second pharmaceutically-acceptable taggant administered to the subject. FIG. 16 illustrates an example embodiment where the example operational flow 1100 of FIG. 11 may include at least one additional operation. Additional operations may include an operation 1610.

After a start operation, an operation 1110, and an operation 1120, the operational flow 1600 moves to an operation 1610. Operation 1610 illustrates detecting a second concentration of at least one of the first pharmaceutically-acceptable taggant or a metabolic byproduct of the first pharmaceutically-acceptable taggant relative to the first concentration of the at least one of the first pharmaceutically-acceptable taggant or the metabolic byproduct of the first pharmaceutically-acceptable taggant. For example, as shown in FIGS. 1 through 10, the concentration of the first taggant may be detected a second time, relative to the concentration of the first taggant detected a first time, in a ratio comprising approximately two to one.

Figure 17:
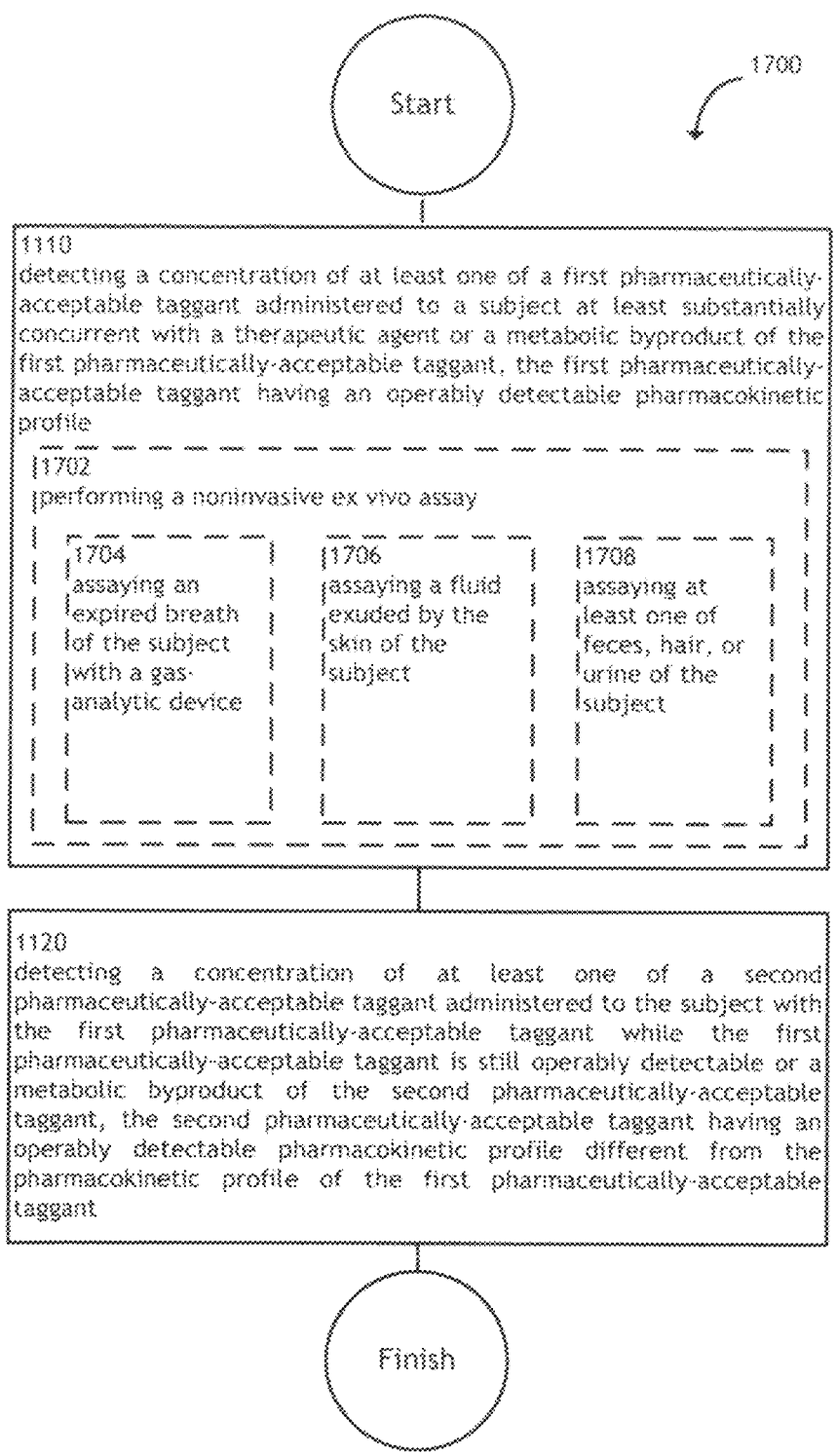
FIG. 17 illustrates an alternative embodiment of the operational flow of FIG. 11.

FIG. 17 illustrates alternative embodiments of the example operational flow 1100 of FIG. 11. FIG. 17 illustrates example embodiments where the operation 1110 may include at least one additional operation. Additional operations may include an operation 1702, an operation 1704, an operation 1706, and/or an operation 1708.

The operation 1702 illustrates performing a noninvasive ex vivo assay. For example, an assay may be performed on the breath of the subject. Further, the operation 1704 illustrates assaying an expired breath of the subject with a gas-analytic device. Further, the operation 1706 illustrates assaying a fluid exuded by the skin of the subject. Further, the operation 1708 illustrates assaying at least one of feces, hair, or urine of the subject.

Figure 18:
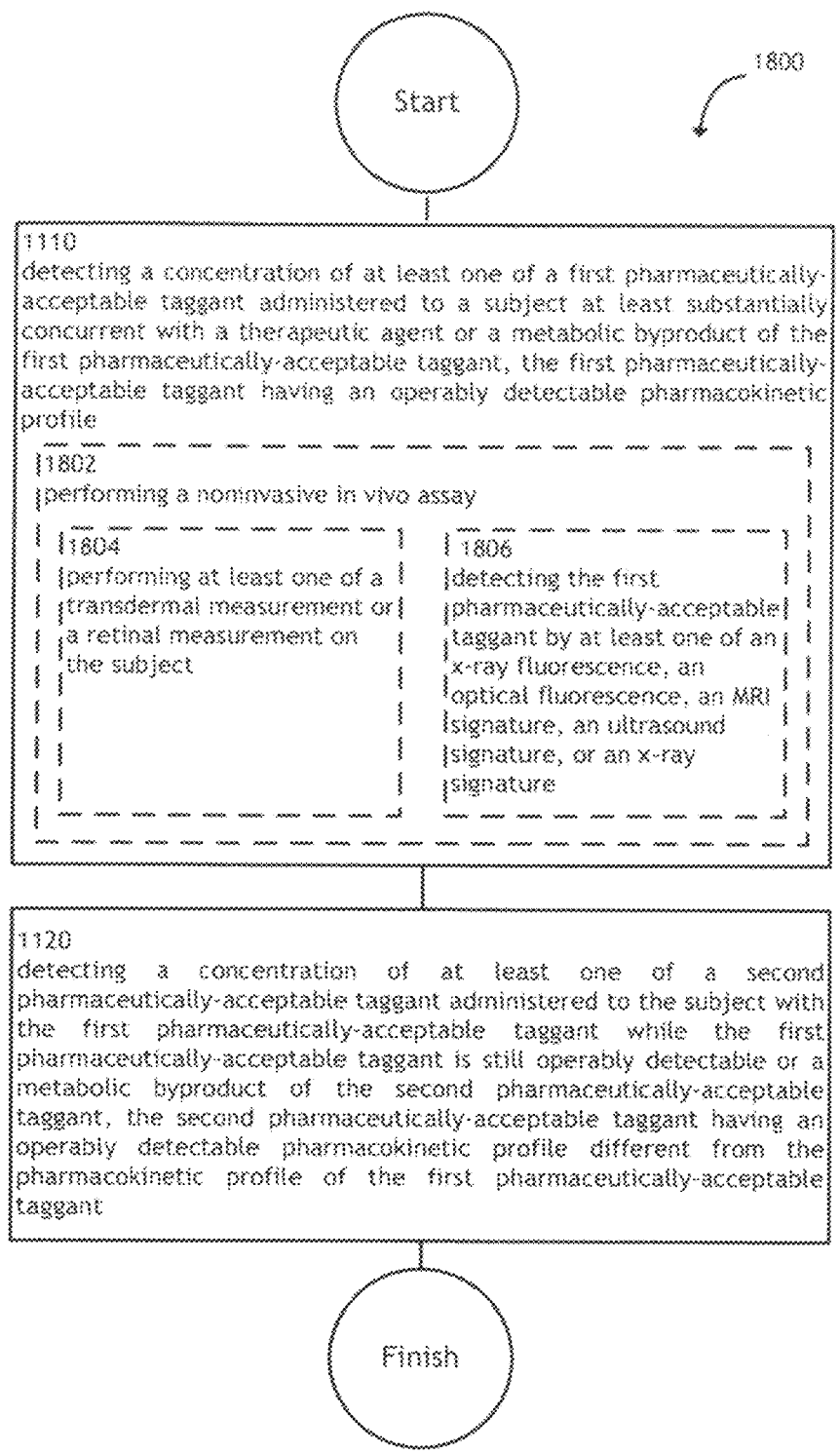
FIG. 18 illustrates an alternative embodiment of the operational flow of FIG. 11.

FIG. 18 illustrates alternative embodiments of the example operational flow 1100 of FIG. 11. FIG. 18 illustrates example embodiments where the operation 1110 may include at least one additional operation. Additional operations may include an operation 1802, an operation 1804, and/or an operation 1806.

The operation 1802 illustrates performing a noninvasive in vivo assay. For example, an assay may be performed transdermally. Further, the operation 1804 illustrates performing at least one of a transdermal measurement or a retinal measurement on the subject. Further, the operation 1806 illustrates detecting the first pharmaceutically-acceptable taggant by at least one of an x-ray fluorescence, an optical fluorescence, an MRI signature, an ultrasound signature, or an x-ray signature.

Figure 19:
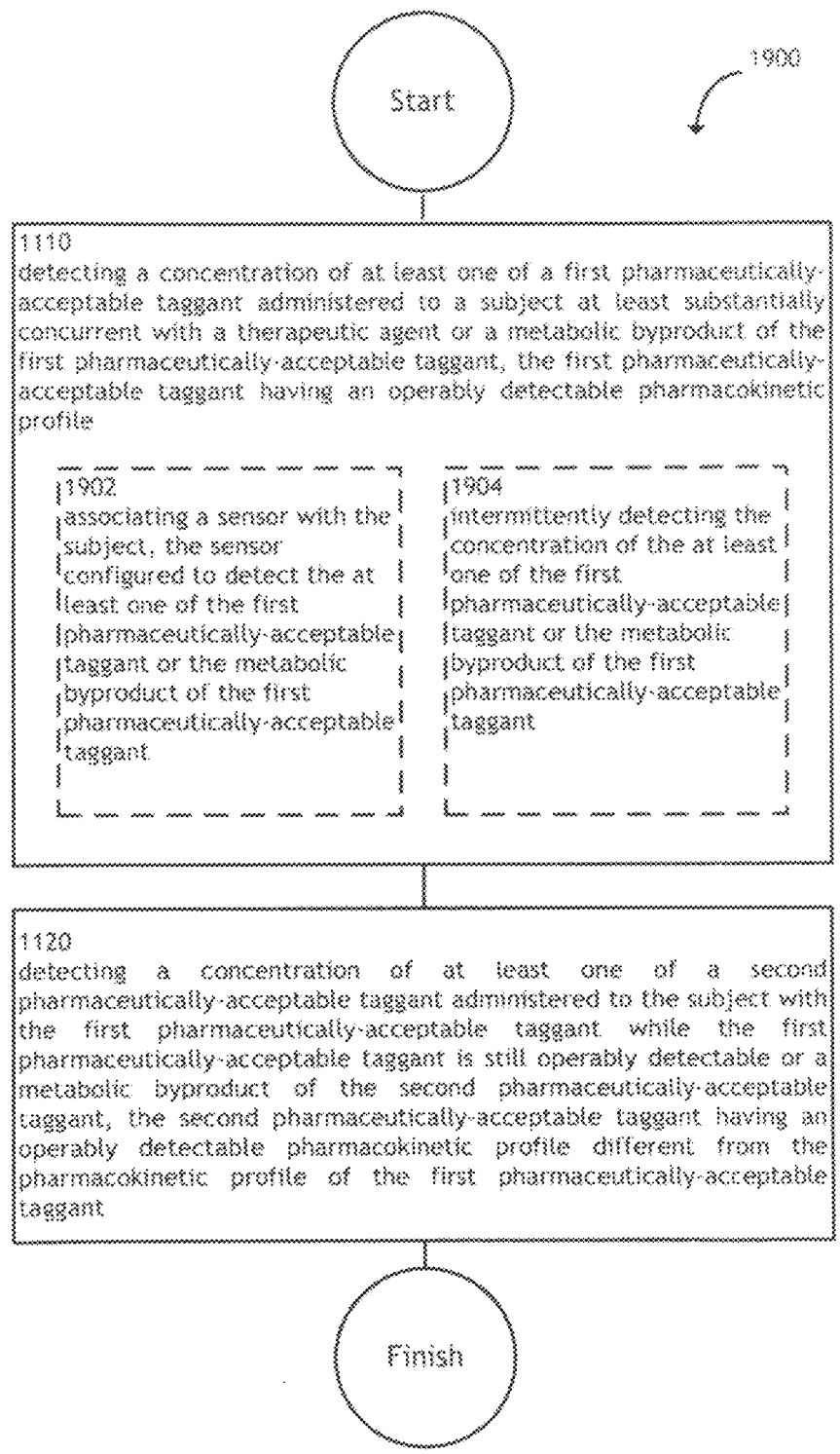
FIG. 19 illustrates an alternative embodiment of the operational flow of FIG. 11.

FIG. 19 illustrates alternative embodiments of the example operational flow 1100 of FIG. 11. FIG. 19 illustrates example embodiments where the operation 1110 may include at least one additional operation. Additional operations may include an operation 1902, and/or an operation 1904.

The operation 1902 illustrates associating a sensor with the subject, the sensor configured to detect the at least one of the first pharmaceutically-acceptable taggant or the metabolic byproduct of the first pharmaceutically-acceptable taggant. For example, a sensor may be strapped to the wrist of a subject for periodical transdermal monitoring of the concentrations of the first and second taggants.

The operation 1904 illustrates intermittently detecting the concentration of the at least one of the first pharmaceutically-acceptable taggant or the metabolic byproduct of the first pharmaceutically-acceptable taggant. For example, the concentration of the first taggant may be detected at least approximately every hour.

Figure 20:
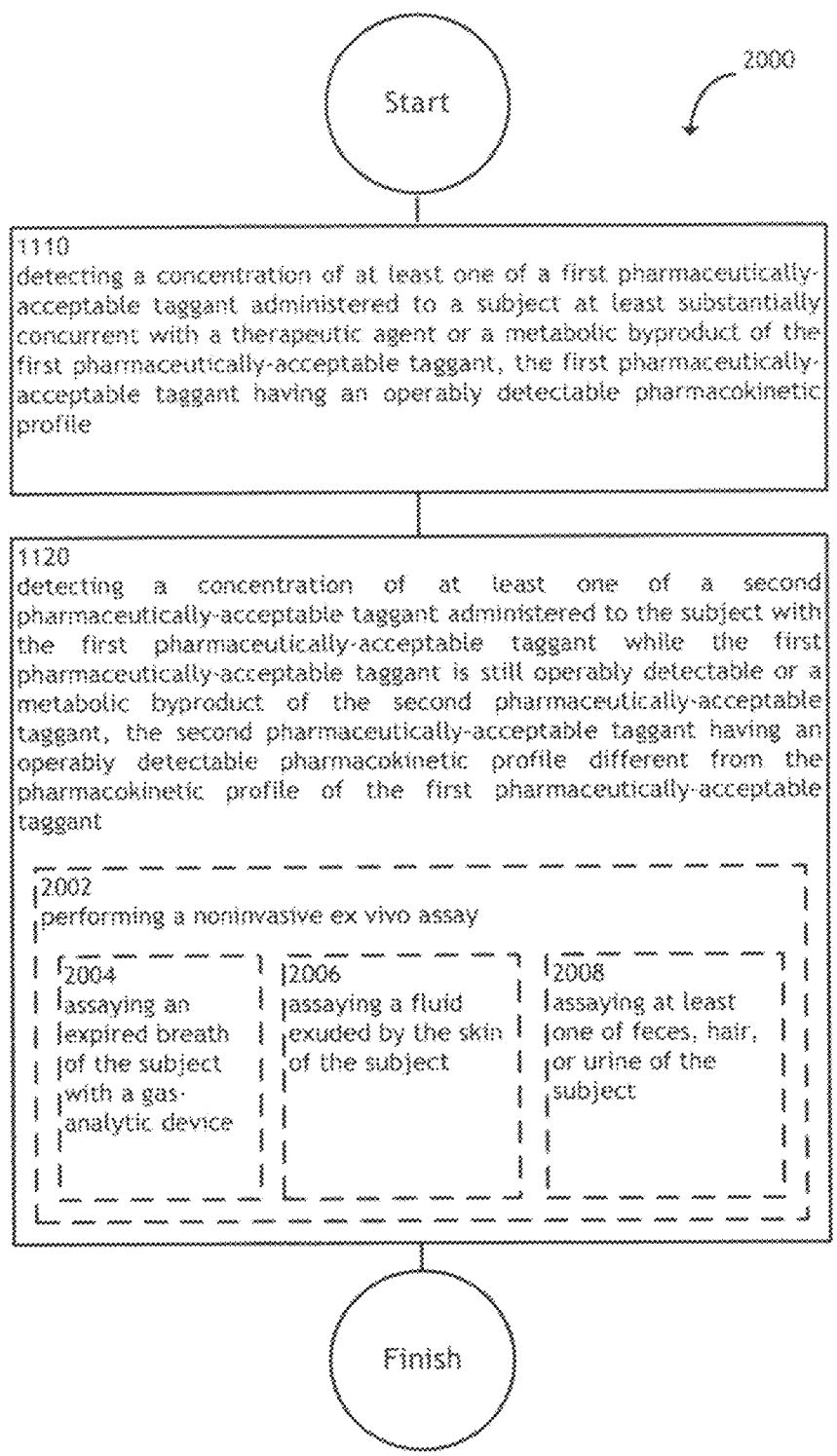
FIG. 20 illustrates an alternative embodiment of the operational flow of FIG. 11.

FIG. 20 illustrates alternative embodiments of the example operational flow 1100 of FIG. 11. FIG. 20 illustrates example embodiments where the operation 1120 may include at least one additional operation. Additional operations may include an operation 2002, an operation 2004, an operation 2006, and/or an operation 2008.

The operation 2002 illustrates performing a noninvasive ex vivo assay. Further, the operation 2004 illustrates assaying an expired breath of the subject with a gas-analytic device. Further, the operation 2006 illustrates assaying a fluid exuded by the skin of the subject. Further, the operation 2008 illustrates assaying at least one of feces, hair, or urine of the subject.

Figure 21:
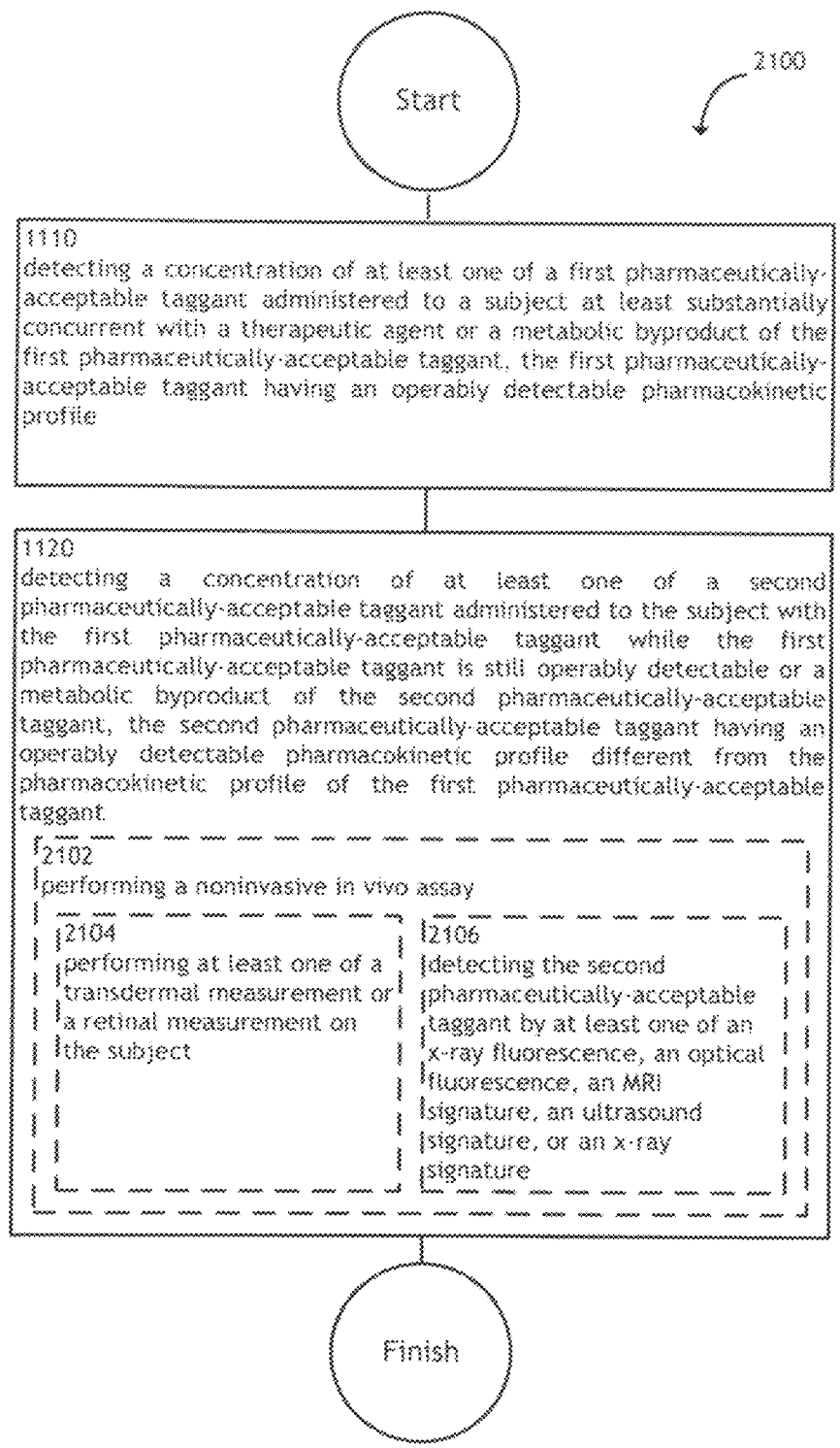
FIG. 21 illustrates an alternative embodiment of the operational flow of FIG. 11.

FIG. 21 illustrates alternative embodiments of the example operational flow 1100 of FIG. 11. FIG. 21 illustrates example embodiments where the operation 1120 may include at least one additional operation. Additional operations may include an operation 2102, an operation 2104, and/or an operation 2106.

The operation 2102 illustrates performing a noninvasive in vivo assay. Further, the operation 2104 illustrates performing at least one of a transdermal measurement or a retinal measurement on the subject. Further, the operation 2106 illustrates detecting the second pharmaceutically-acceptable taggant by at least one of an x-ray fluorescence, an optical fluorescence, an MRI signature, an ultrasound signature, or an x-ray signature.

Figure 22:
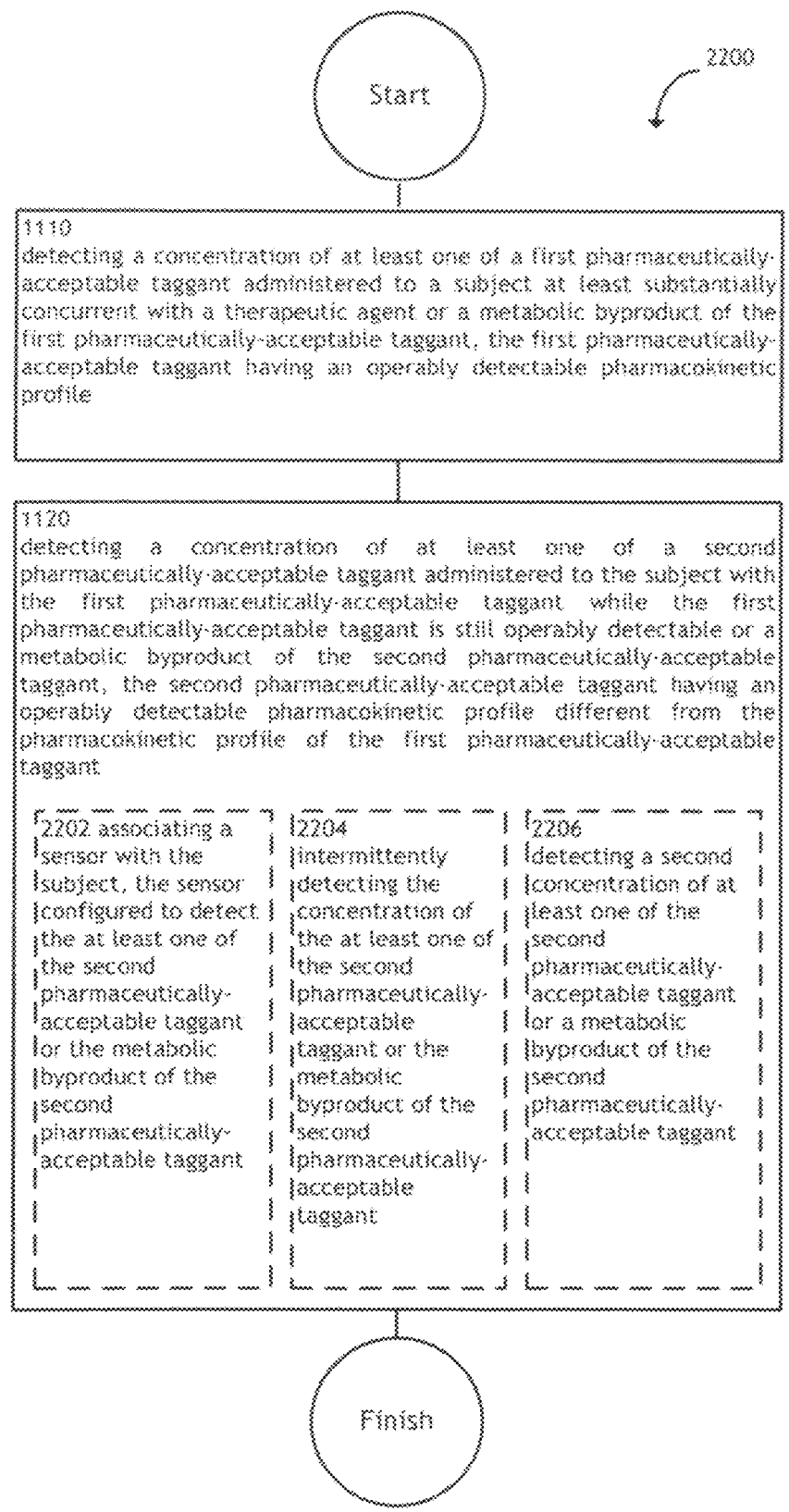
FIG. 22 illustrates an alternative embodiment of the operational flow of FIG. 11.

FIG. 22 illustrates alternative embodiments of the example operational flow 1100 of FIG. 11. FIG. 22 illustrates example embodiments where the operation 1120 may include at least one additional operation. Additional operations may include an operation 2202, an operation 2204, and/or an operation 2206.

The operation 2202 illustrates associating a sensor with the subject, the sensor configured to detect the at least one of the second pharmaceutically-acceptable taggant or the metabolic byproduct of the second pharmaceutically-acceptable taggant.

The operation 2204 illustrates intermittently detecting the concentration of the at least one of the second pharmaceutically-acceptable taggant or the metabolic byproduct of the second pharmaceutically-acceptable taggant.

The operation 2206 illustrates detecting a second concentration of at least one of the second pharmaceutically-acceptable taggant or a metabolic byproduct of the second pharmaceutically-acceptable taggant.

Figure 23:
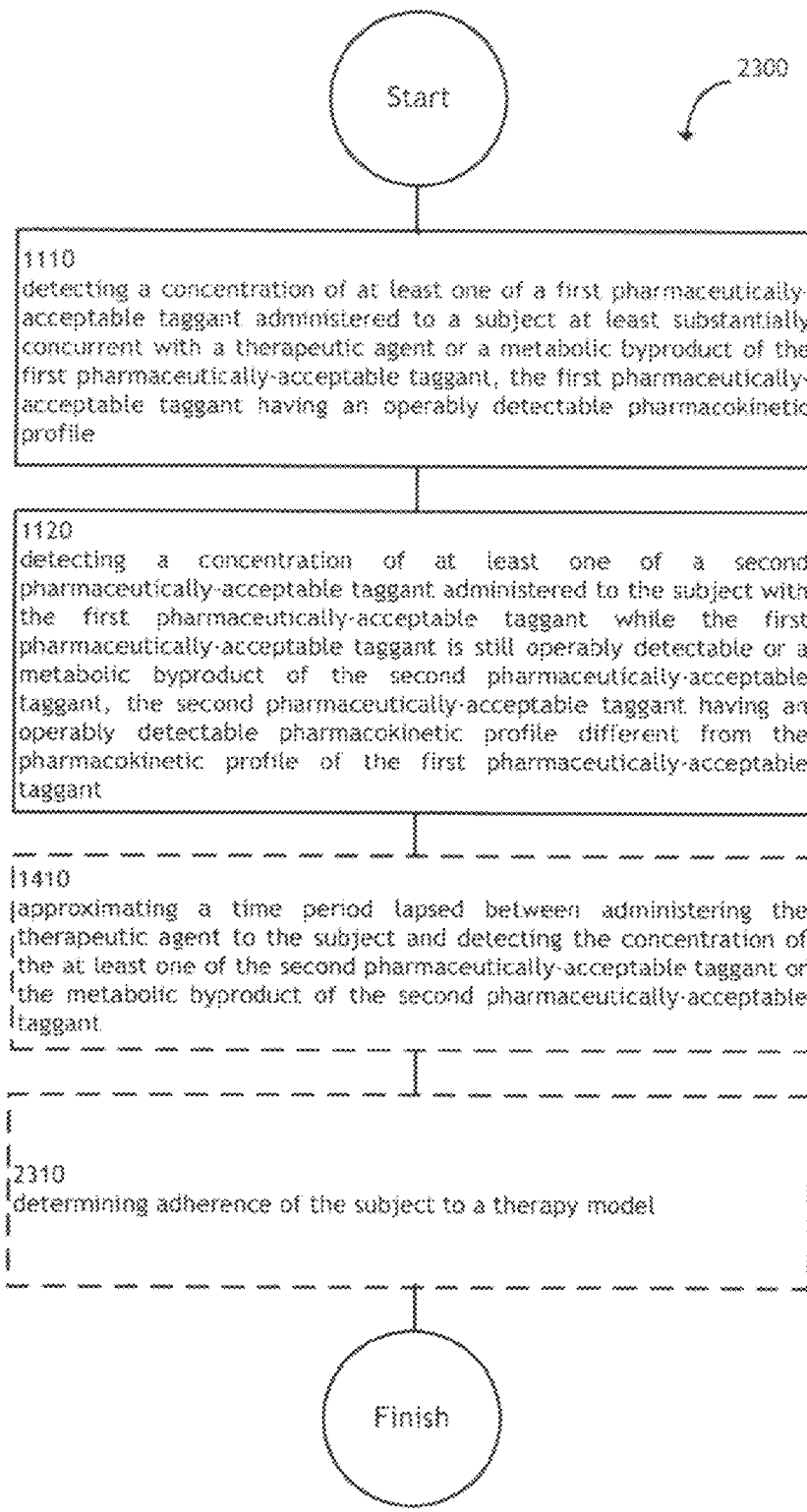
FIG. 23 illustrates an alternative embodiment of the operational flow of FIG. 14.

FIG. 23 illustrates alternative embodiments of the example operational flow 1400 of FIG. 14. FIG. 23 illustrates example embodiments where the operation 1410 may include at least one additional operation. Additional operations may include an operation 2310.

After a start operation, an operation 1110, an operation 1120, and an operation 1410, the operational flow 1400 moves to an operation 2310. Operation 2310 illustrates determining adherence of the subject to a therapy model. For example, as shown in FIGS. 1 through 10, if the therapy model requires a subject to take the therapeutic agent every eight hours, the subject may be notified when it is determined that more than eight hours have passed since the last dosage.

Figure 24:
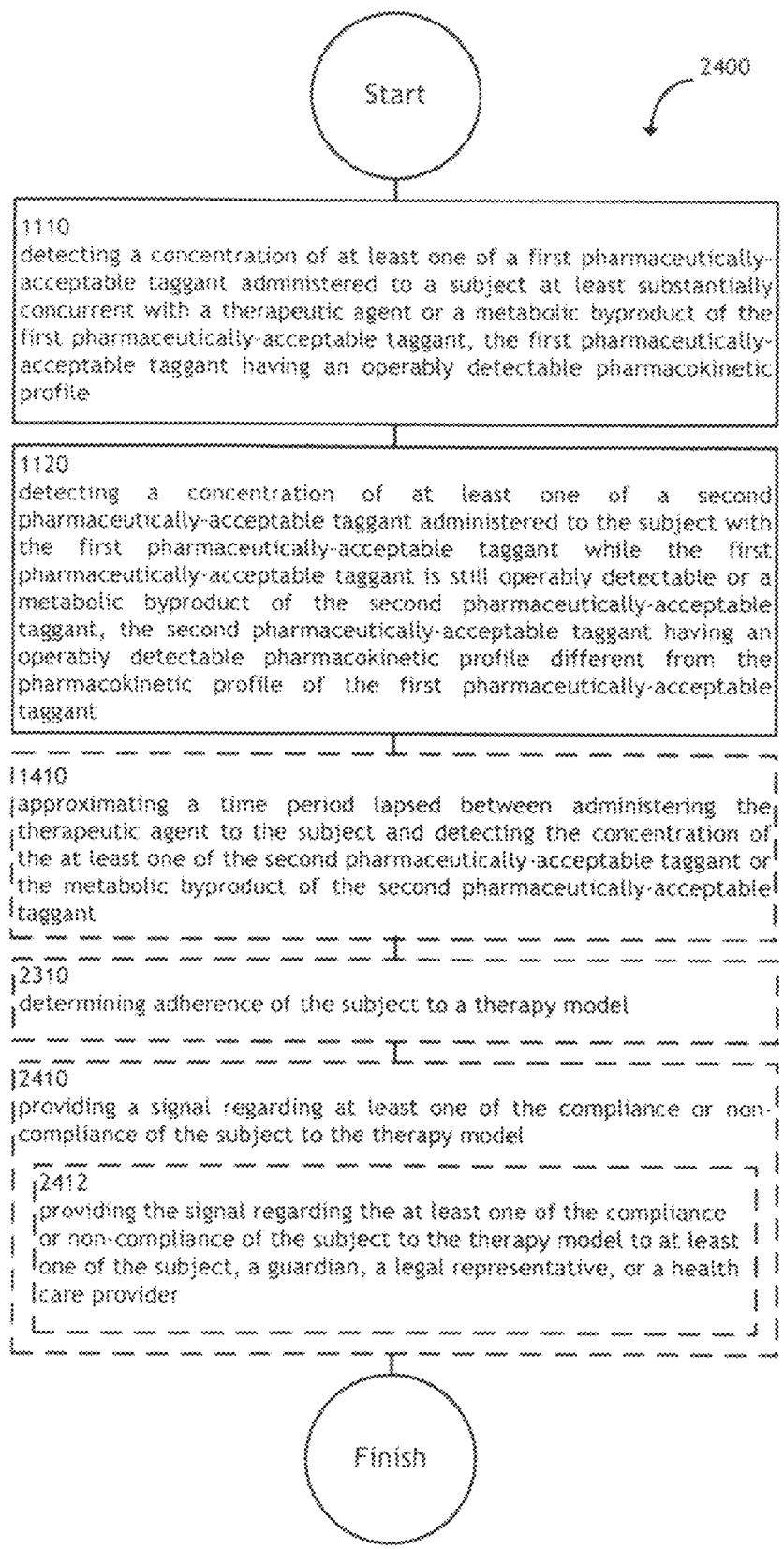
FIG. 24 illustrates an alternative embodiment of the operational flow of FIG. 14.

FIG. 24 illustrates alternative embodiments of the example operational flow 1400 of FIG. 14. FIG. 24 illustrates example embodiments where the operation 1410 may include at least one additional operation. Additional operations may include an operation 2310, an operation 2410, and/or an operation 2412.

After a start operation, an operation 1110, an operation 1120, an operation 1410, and an operation 2310, the operational flow 1400 moves to an operation 2410. Operation 2410 illustrates providing a signal regarding at least one of the compliance or non-compliance of the subject to the therapy model. For example, as shown in FIGS. 1 through 10, the subject may be fitted with a wearable alarm for alerting the subject or a health care provider when the subject is non-compliant with the therapy model (e.g., when more than eight hours have elapsed since the last dosage, as previously described).

The operation 2412 illustrates providing the signal regarding the at least one of the compliance or non-compliance of the subject to the therapy model to at least one of the subject, a guardian, a legal representative, or a health care provider.

Figure 25:
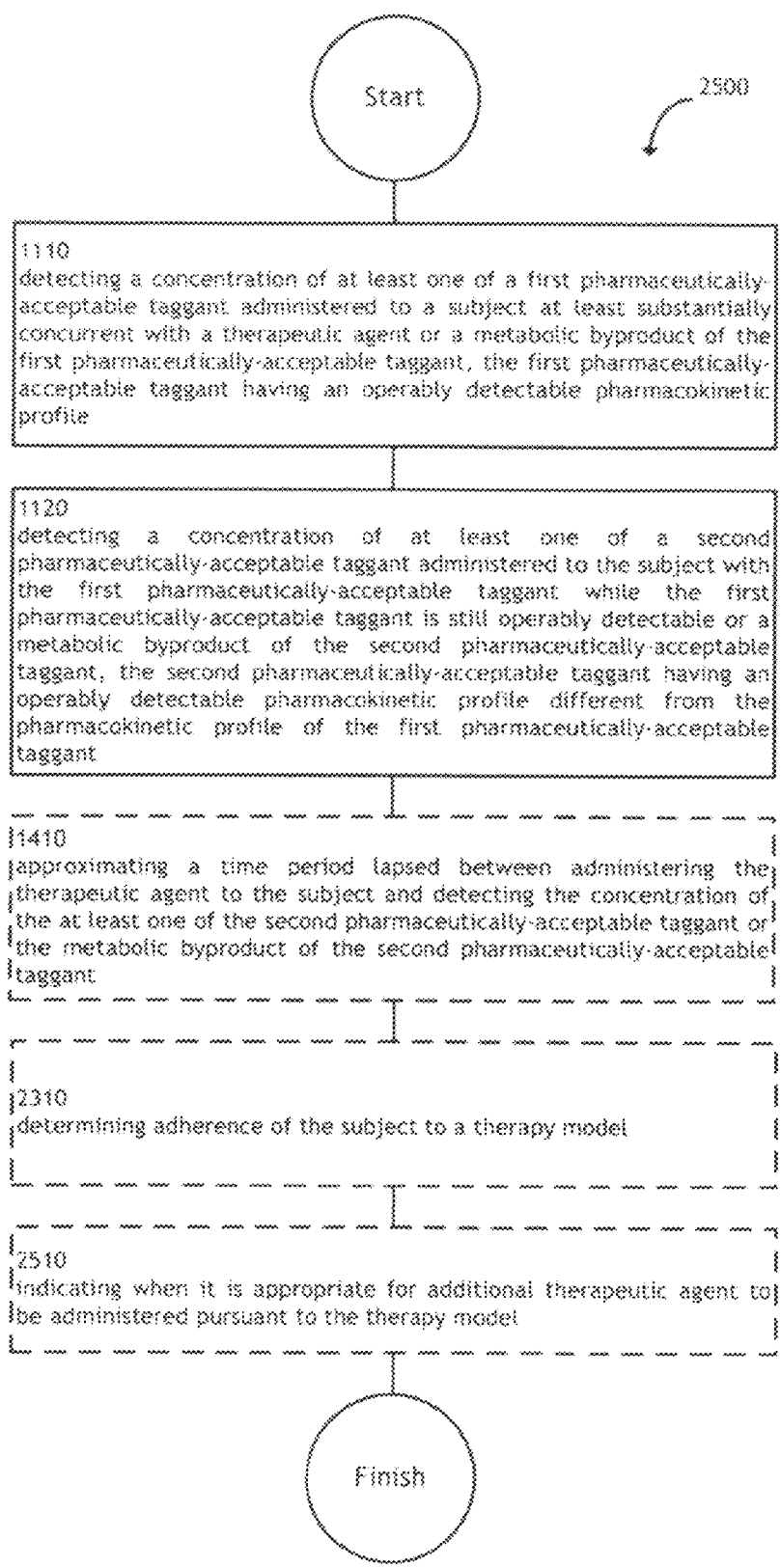
FIG. 25 illustrates an alternative embodiment of the operational flow of FIG. 14.

FIG. 25 illustrates alternative embodiments of the example operational flow 1400 of FIG. 14. FIG. 25 illustrates example embodiments where the operation 1410 may include at least one additional operation. Additional operations may include an operation 2310, and/or an operation 2510.

After a start operation, an operation 1110, an operation 1120, an operation 1410, and an operation 2310, the operational flow 1400 moves to an operation 2510. Operation 2510 illustrates indicating when it is appropriate for additional therapeutic agent to be administered pursuant to the therapy model. For example, as shown in FIGS. 1 through 10, the subject may be fitted with an alarm configured to sound when it has been determined that it is time for the subject's next dosage of the therapeutic agent.

Figure 26:
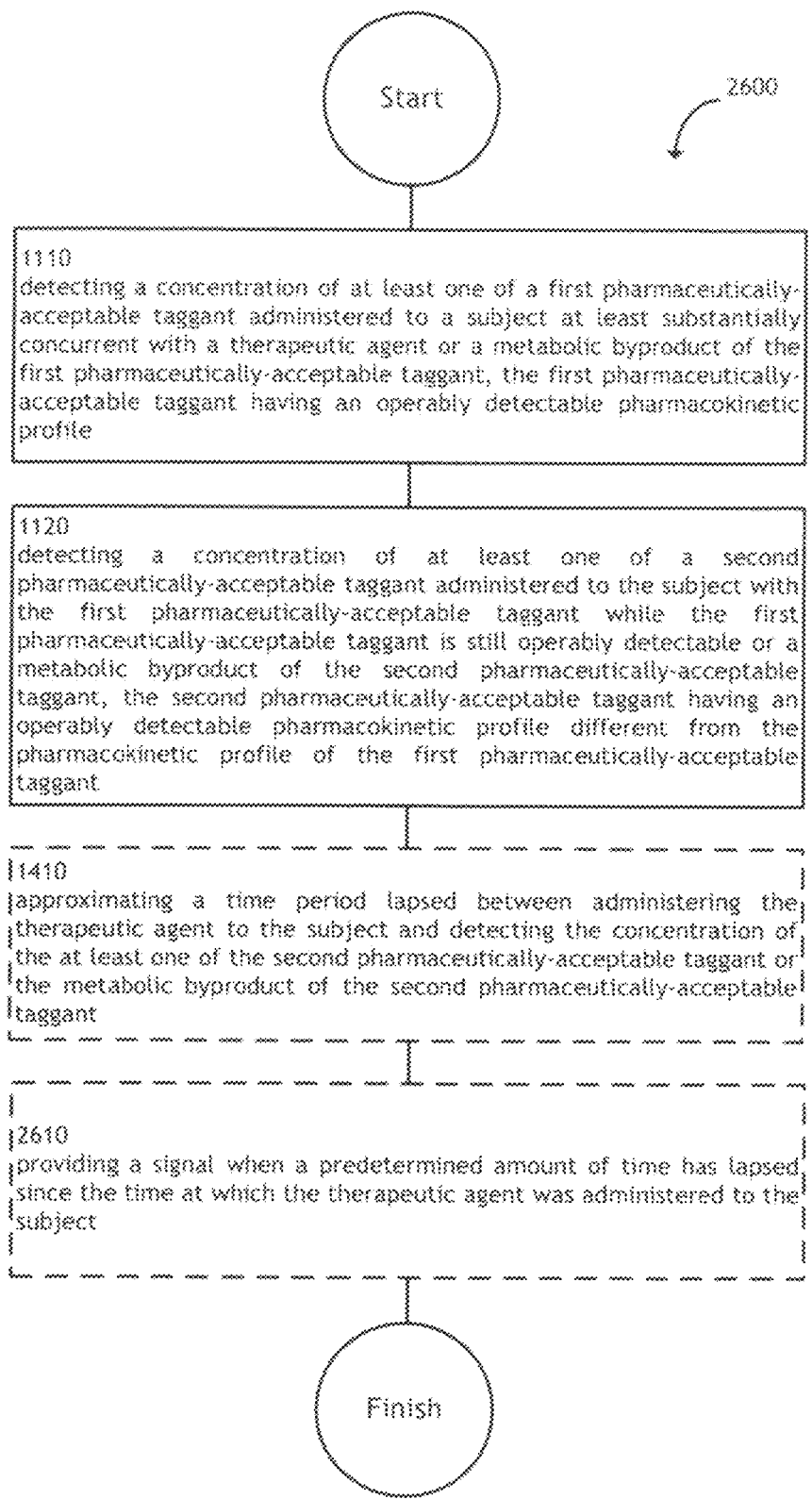
FIG. 26 illustrates an alternative embodiment of the operational flow of FIG. 14.

FIG. 26 illustrates alternative embodiments of the example operational flow 1400 of FIG. 14. FIG. 26 illustrates example embodiments where the operation 1410 may include at least one additional operation. Additional operations may include an operation 2610.

After a start operation, an operation 1110, an operation 1120, and an operation 1410, the operational flow 1400 moves to an operation 2610. Operation 2610 illustrates providing a signal when a predetermined amount of time has lapsed since the time at which the therapeutic agent was administered to the subject. For example, as shown in FIGS. 1 through 10, the subject may be fitted with an alarm configured to sound when eight hours has elapsed since a previous dosage.

Figure 27:
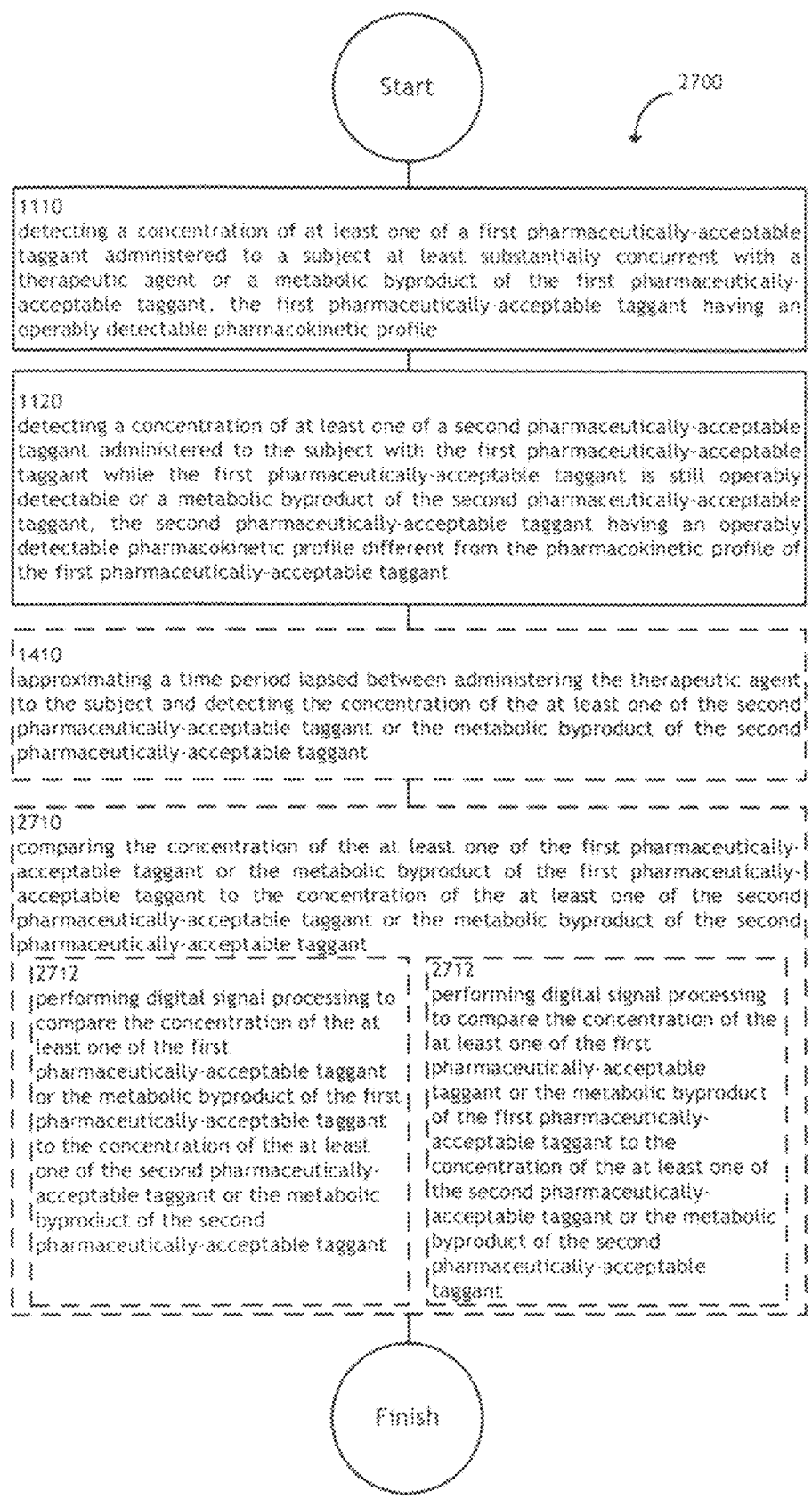
FIG. 27 illustrates an alternative embodiment of the operational flow of FIG. 14.

FIG. 27 illustrates alternative embodiments of the example operational flow 1400 of FIG. 14. FIG. 27 illustrates example embodiments where the operation 1410 may include at least one additional operation. Additional operations may include an operation 2710, an operation 2712, and/or an operation 2714.

After a start operation, an operation 1110, an operation 1120, and an operation 1410, the operational flow 2700 moves to an operation 2710. Operation 2710 illustrates comparing the concentration of the at least one of the first pharmaceutically-acceptable taggant or the metabolic byproduct of the first pharmaceutically-acceptable taggant to the concentration of the at least one of the second pharmaceutically-acceptable taggant or the metabolic byproduct of the second pharmaceutically-acceptable taggant.

The operation 2712 illustrates performing digital signal processing to compare the concentration of the at least one of the first pharmaceutically-acceptable taggant or the metabolic byproduct of the first pharmaceutically-acceptable taggant to the concentration of the at least one of the second pharmaceutically-acceptable taggant or the metabolic byproduct of the second pharmaceutically-acceptable taggant.

The operation 2714 illustrates performing a Fourier analysis to compare the concentration of the at least one of the first pharmaceutically-acceptable taggant or the metabolic byproduct of the first pharmaceutically-acceptable taggant to the concentration of the at least one of the second pharmaceutically-acceptable taggant or the metabolic byproduct of the second pharmaceutically-acceptable taggant.

Figure 28:
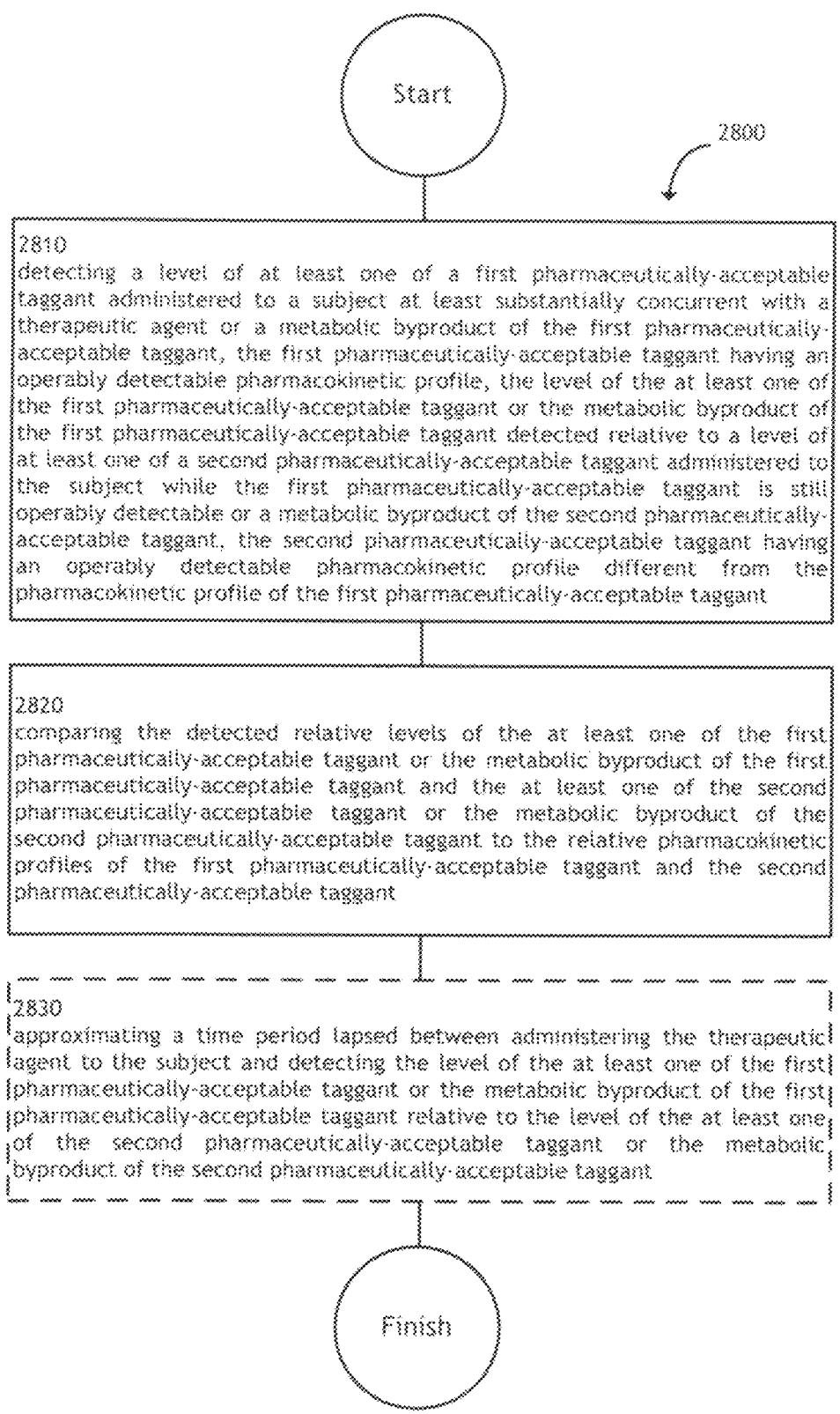
FIG. 28 illustrates an operational flow representing example operations related to approximating a time period lapsed between administering a therapeutic agent to a subject and detecting the level of a first pharmaceutically-acceptable taggant relative to the level of a second pharmaceutically-acceptable taggant administered to the subject.

FIG. 28 illustrates an operational flow 2800 representing example operations related to approximating a time period lapsed between administering a therapeutic agent to a subject and detecting the level of a first pharmaceutically-acceptable taggant relative to the level of a second pharmaceutically-acceptable taggant administered to the subject. In FIG. 28 and in following figures that include various examples of operational flows, discussion and explanation may be provided with respect to the above-described examples of FIGS. 1 through 10, and/or with respect to other examples and contexts. However, it should be understood that the operational flows may be executed in a number of other environments and contexts, and/or in modified versions of FIGS. 1 through 10. Also, although the various operational flows are presented in the sequence(s) illustrated, it should be understood that the various operations may be performed in other orders than those which are illustrated, or may be performed concurrently.

After a start operation, the operational flow 2800 moves to an operation 2810. Operation 2810 depicts detecting a level of at least one of a first pharmaceutically-acceptable taggant administered to a subject at least substantially concurrent with a therapeutic agent or a metabolic byproduct of the first pharmaceutically-acceptable taggant, the first pharmaceutically-acceptable taggant having an operably detectable pharmacokinetic profile, the level of the at least one of the first pharmaceutically-acceptable taggant or the metabolic byproduct of the first pharmaceutically-acceptable taggant detected relative to a level of at least one of a second pharmaceutically-acceptable taggant administered to the subject while the first pharmaceutically-acceptable taggant is still operably detectable or a metabolic byproduct of the second pharmaceutically-acceptable taggant, the second pharmaceutically-acceptable taggant having an operably detectable pharmacokinetic profile different from the pharmacokinetic profile of the first pharmaceutically-acceptable taggant.

Then, operation 2820 depicts comparing the detected relative levels of the at least one of the first pharmaceutically-acceptable taggant or the metabolic byproduct of the first pharmaceutically-acceptable taggant and the at least one of the second pharmaceutically-acceptable taggant or the metabolic byproduct of the second pharmaceutically-acceptable taggant to the relative pharmacokinetic profiles of the first pharmaceutically-acceptable taggant and the second pharmaceutically-acceptable taggant. For example, as shown in FIGS. 1 through 10, the difference between the level of the first taggant and the level of the second taggant may be referenced to a point 808 on a plasma concentration profile comprising the difference between a pharmacokinetic profile for the first taggant and a pharmacokinetic profile for the second taggant.

Then, operation 2830 depicts approximating a time period lapsed between administering the therapeutic agent to the subject and detecting the level of the at least one of the first pharmaceutically-acceptable taggant or the metabolic byproduct of the first pharmaceutically-acceptable taggant relative to the level of the at least one of the second pharmaceutically-acceptable taggant or the metabolic byproduct of the second pharmaceutically-acceptable taggant.

Figure 29:
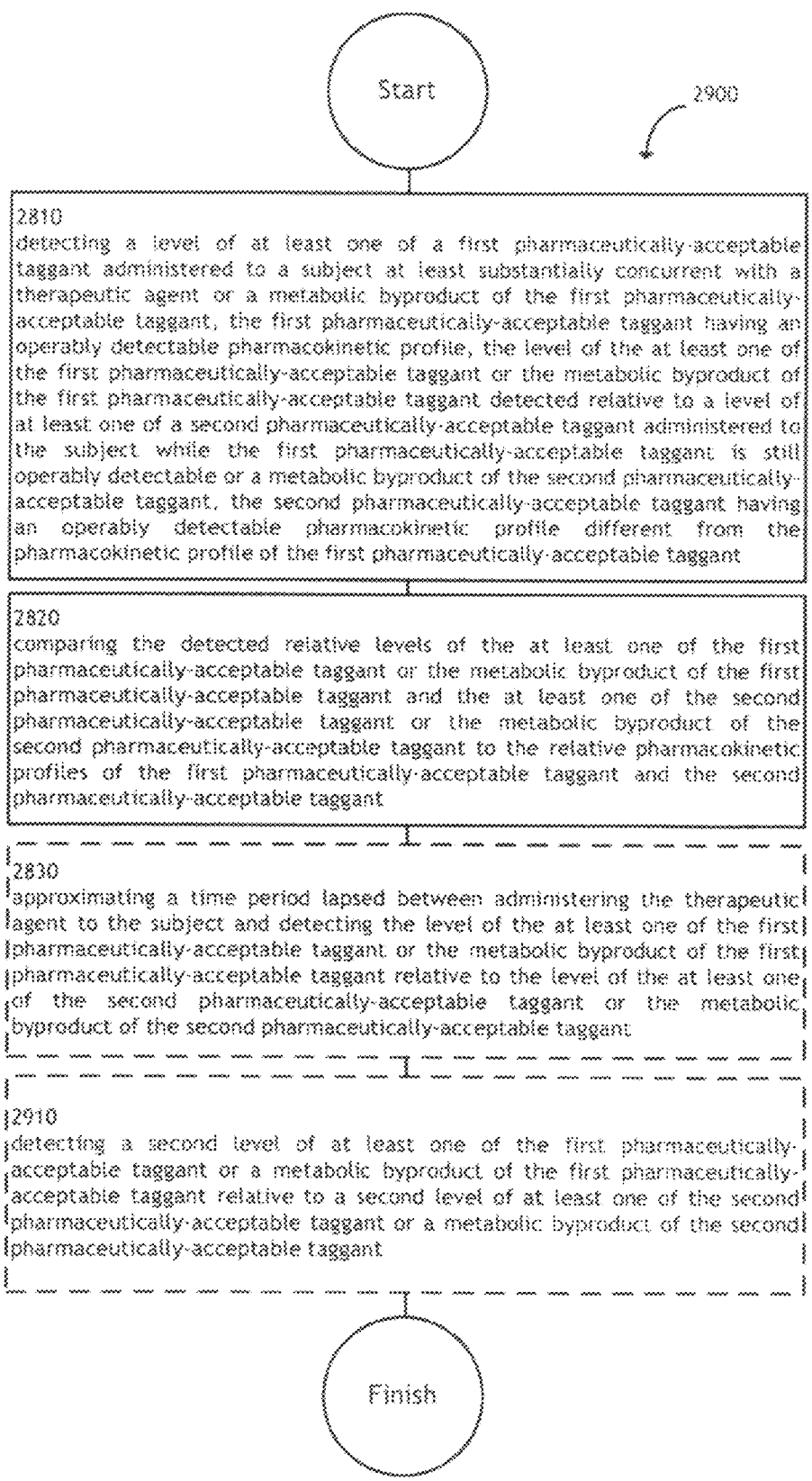
FIG. 29 illustrates an operational flow representing example operations related to determining a time period lapsed between administering a therapeutic agent to a subject and detecting relative levels for a first pharmaceutically-acceptable taggant and a second pharmaceutically-acceptable taggant administered to the subject.

FIG. 29 illustrates an operational flow 2900 representing example operations related to determining a time period lapsed between administering a therapeutic agent to a subject and detecting relative levels for a first pharmaceutically-acceptable taggant and a second pharmaceutically-acceptable taggant administered to the subject. FIG. 29 illustrates an example embodiment where the example operational flow 2800 of FIG. 28 may include at least one additional operation. Additional operations may include an operation 2910.

After a start operation, an operation 2810, an operation 2820, and an operation 2830, the operational flow 2900 moves to an operation 2910. Operation 2910 illustrates detecting a second level of at least one of the first pharmaceutically-acceptable taggant or a metabolic byproduct of the first pharmaceutically-acceptable taggant relative to a second level of at least one of the second pharmaceutically-acceptable taggant or a metabolic byproduct of the second pharmaceutically-acceptable taggant. For example, as shown in FIGS. 1 through 10, a second level of the first taggant relative to the second taggant may be detected based on an MRI contrast agent subsequent to detecting a first level for the first taggant relative to a the second taggant utilizing a plasma concentration.

Figure 30:
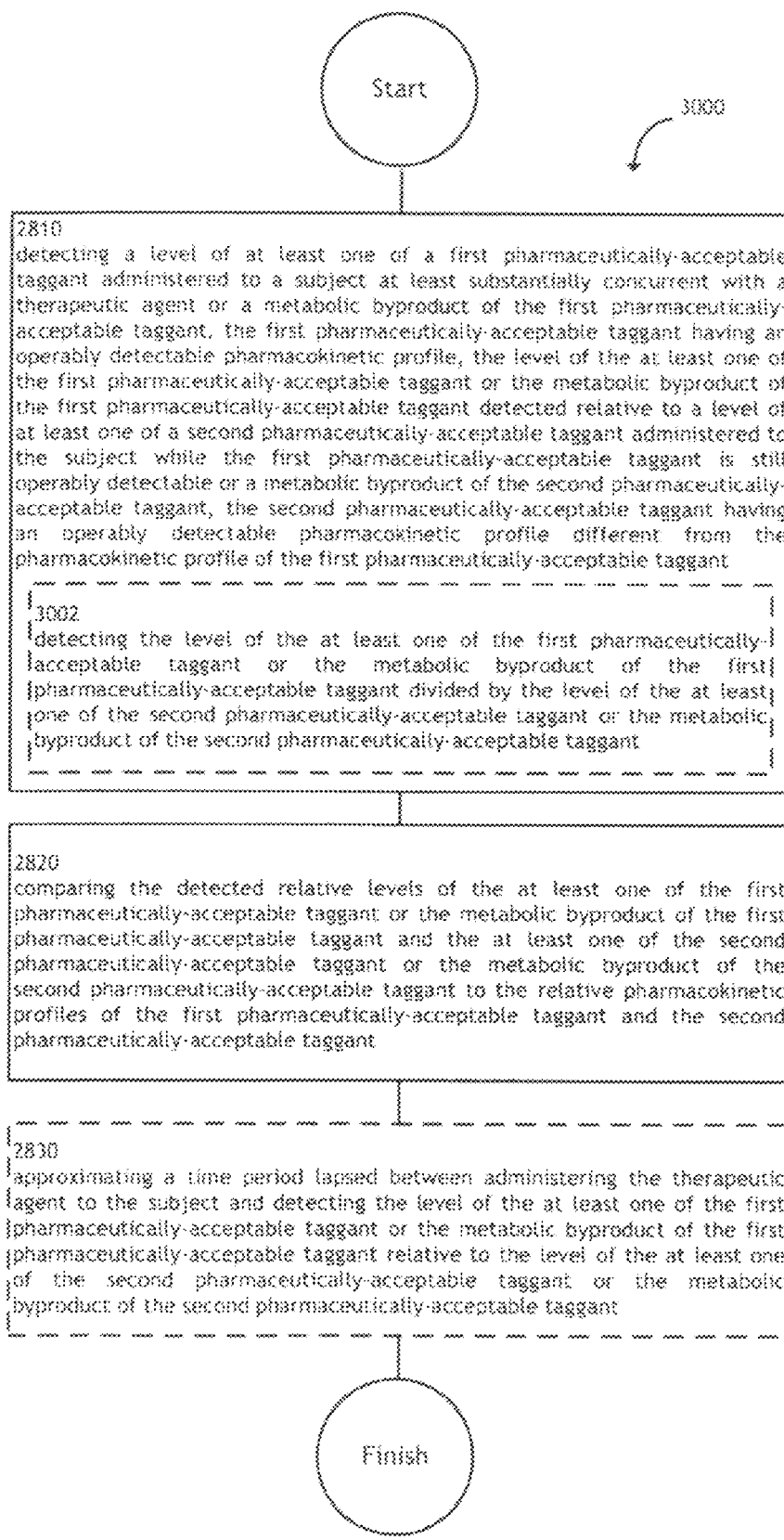
FIG. 30 illustrates an alternative embodiment of the operational flow of FIG. 28.

FIG. 30 illustrates alternative embodiments of the example operational flow 2800 of FIG. 28. FIG. 30 illustrates example embodiments where the operation 2810 may include at least one additional operation. Additional operations may include an operation 3002.

The operation 3002 illustrates detecting the level of the at least one of the first pharmaceutically-acceptable taggant or the metabolic byproduct of the first pharmaceutically-acceptable taggant divided by the level of the at least one of the second pharmaceutically-acceptable taggant or the metabolic byproduct of the second pharmaceutically-acceptable taggant. For example, as shown in FIGS. 1 through 10, the level of the first taggant may be detected relative to the level of the second taggant such that the first taggant level divided by the second taggant level is about 1.5.

Figure 31:
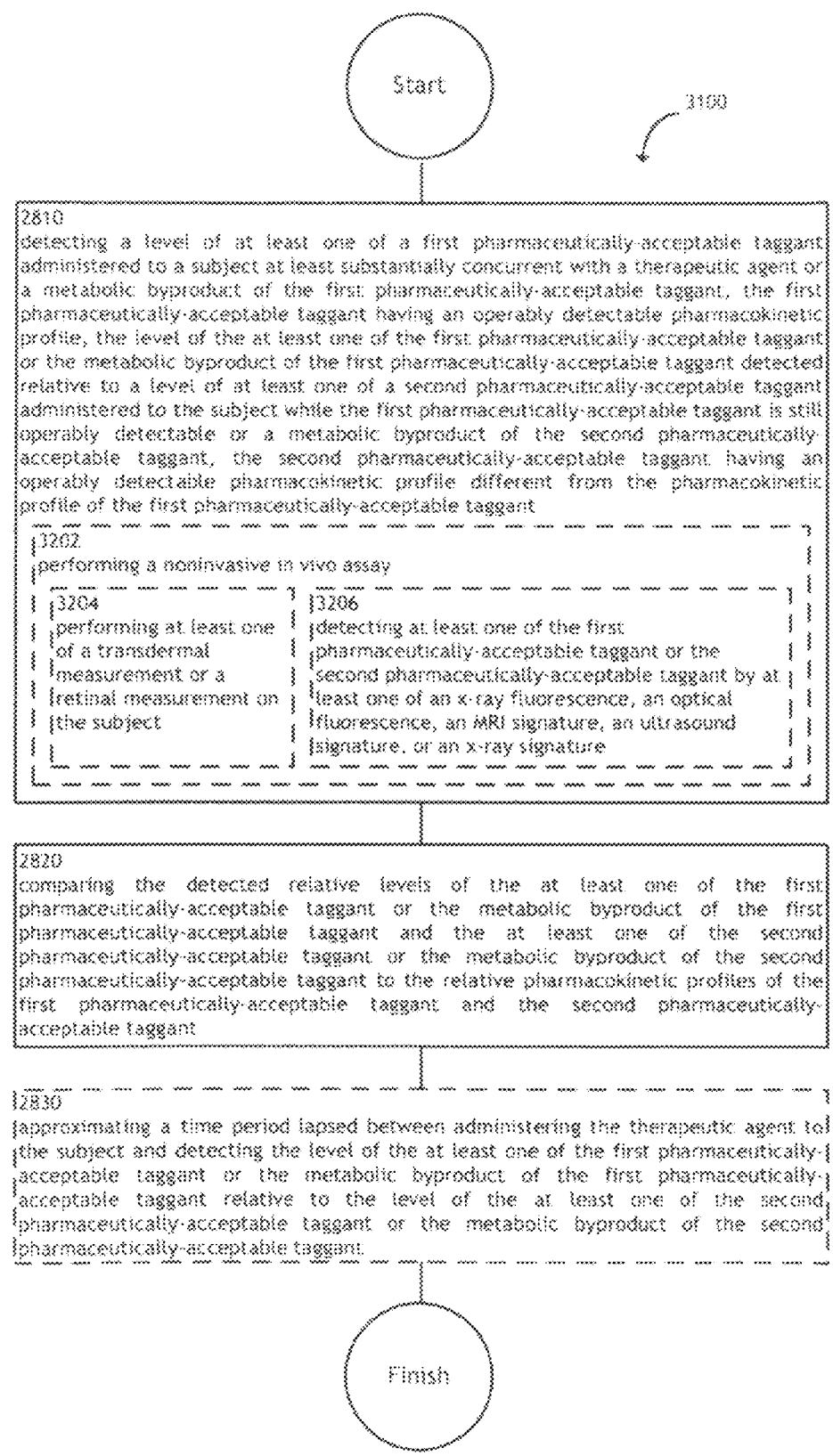
FIG. 31 illustrates an alternative embodiment of the operational flow of FIG. 28.

FIG. 31 illustrates alternative embodiments of the example operational flow 2800 of FIG. 28. FIG. 31 illustrates example embodiments where the operation 2810 may include at least one additional operation. Additional operations may include an operation 3102, an operation 3104, an operation 3106, and/or an operation 3108.

The operation 3102 illustrates performing a noninvasive ex vivo assay. Further, the operation 3104 illustrates assaying an expired breath of the subject with a gas-analytic device. Further, the operation 3106 illustrates assaying a fluid exuded by the skin of the subject. Further, the operation 3108 illustrates assaying at least one of feces, hair, or urine of the subject.

Figure 32:
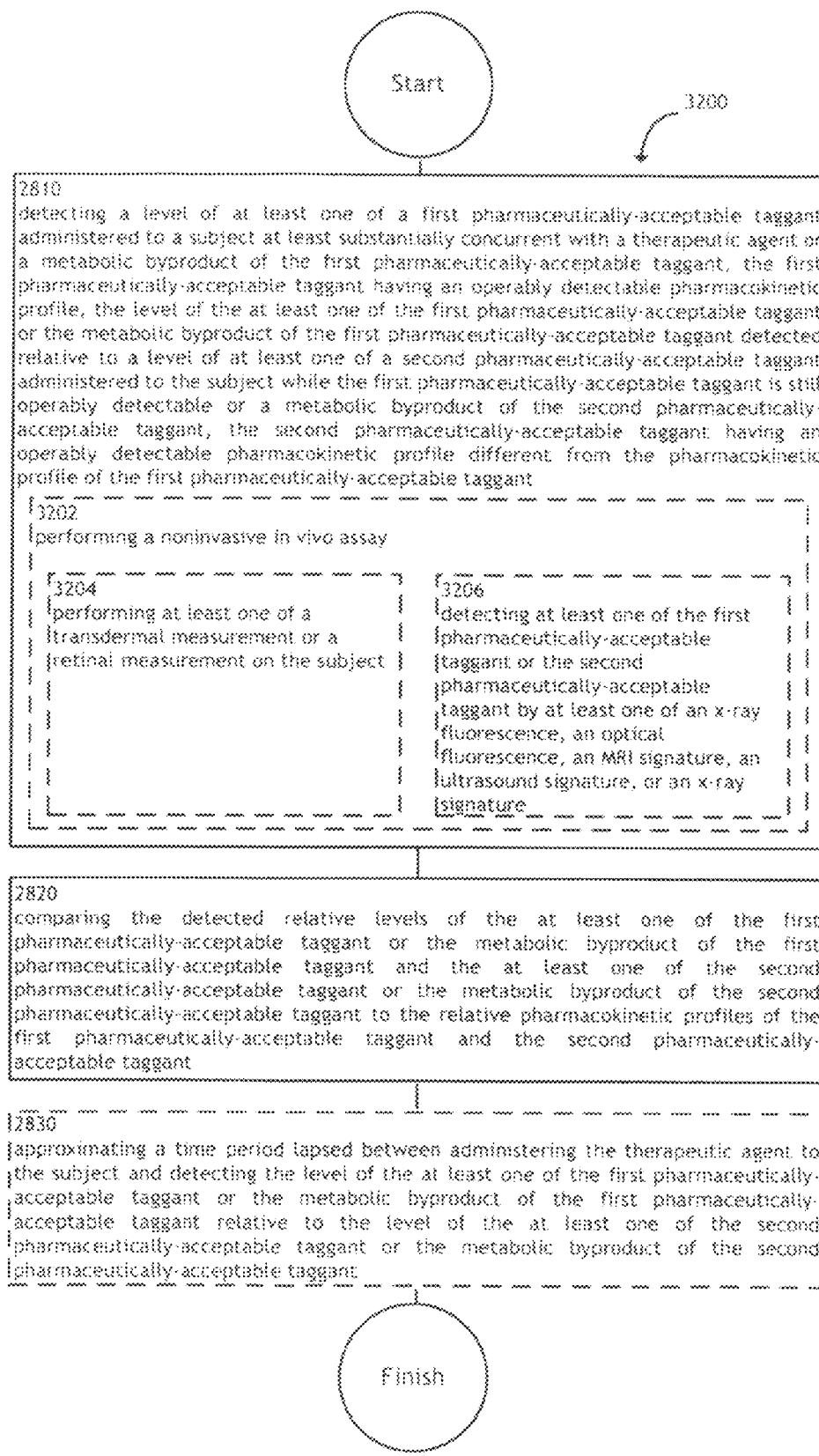
FIG. 32 illustrates an alternative embodiment of the operational flow of FIG. 28.

FIG. 32 illustrates alternative embodiments of the example operational flow 2800 of FIG. 28. FIG. 32 illustrates example embodiments where the operation 2810 may include at least one additional operation. Additional operations may include an operation 3202, an operation 3204, and/or an operation 3206.

The operation 3202 illustrates performing a noninvasive in vivo assay. Further, the operation 3204 illustrates performing at least one of a transdermal measurement or a retinal measurement on the subject. Further, the operation 3206 illustrates detecting at least one of the first pharmaceutically-acceptable taggant or the second pharmaceutically-acceptable taggant by at least one of an x-ray fluorescence, an optical fluorescence, an MRI signature, an ultrasound signature, or an x-ray signature.

Figure 33:
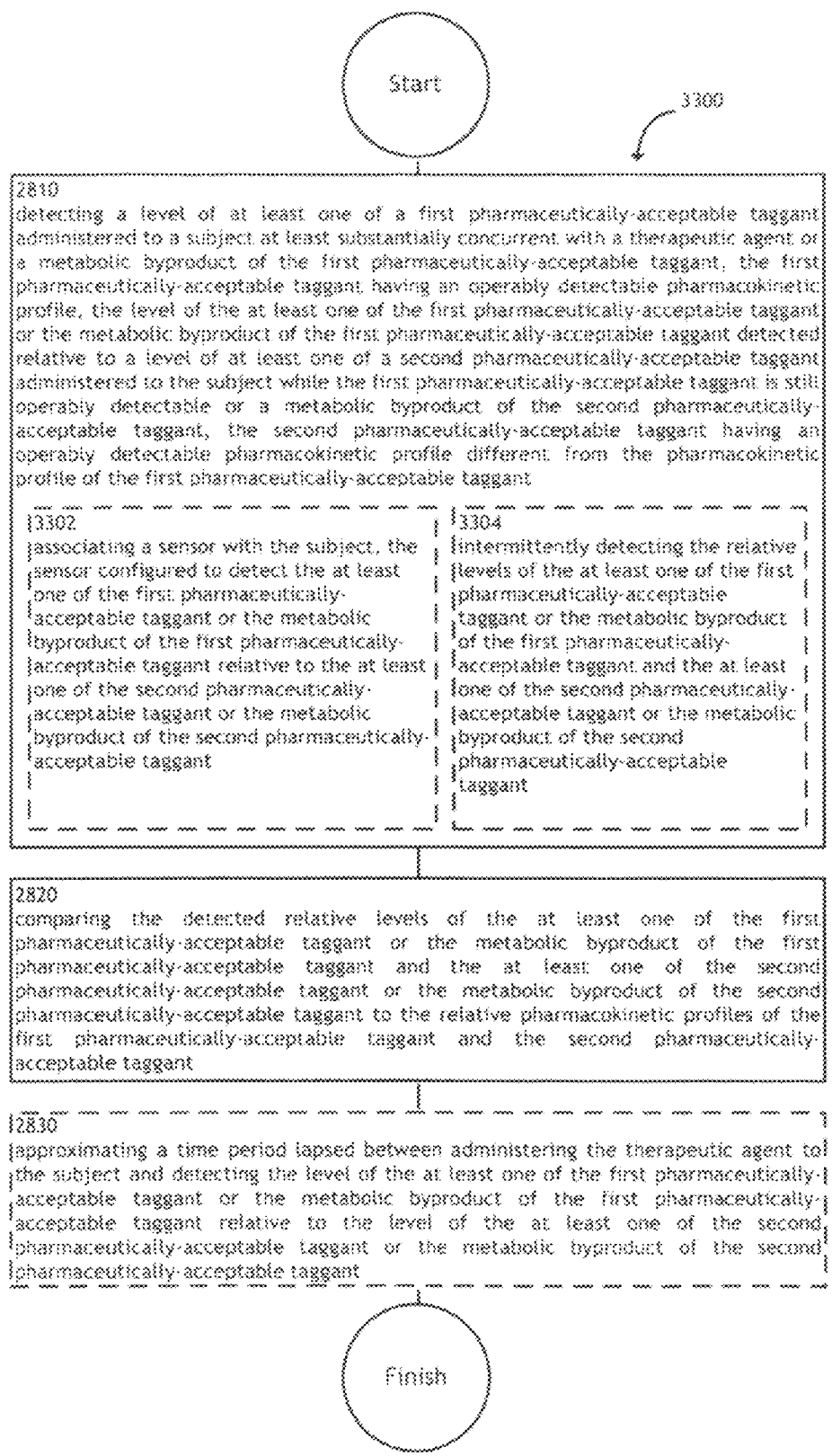
FIG. 33 illustrates an alternative embodiment of the operational flow of FIG. 28.

FIG. 33 illustrates alternative embodiments of the example operational flow 2800 of FIG. 28. FIG. 33 illustrates example embodiments where the operation 2810 may include at least one additional operation. Additional operations may include an operation 3302, and/or an operation 3304.

The operation 3302 illustrates associating a sensor with the subject, the sensor configured to detect the at least one of the first pharmaceutically-acceptable taggant or the metabolic byproduct of the first pharmaceutically-acceptable taggant relative to the at least one of the second pharmaceutically-acceptable taggant or the metabolic byproduct of the second pharmaceutically-acceptable taggant.

The operation 3304 illustrates intermittently detecting the relative levels of the at least one of the first pharmaceutically-acceptable taggant or the metabolic byproduct of the first pharmaceutically-acceptable taggant and the at least one of the second pharmaceutically-acceptable taggant or the metabolic byproduct of the second pharmaceutically-acceptable taggant.

Figure 34:
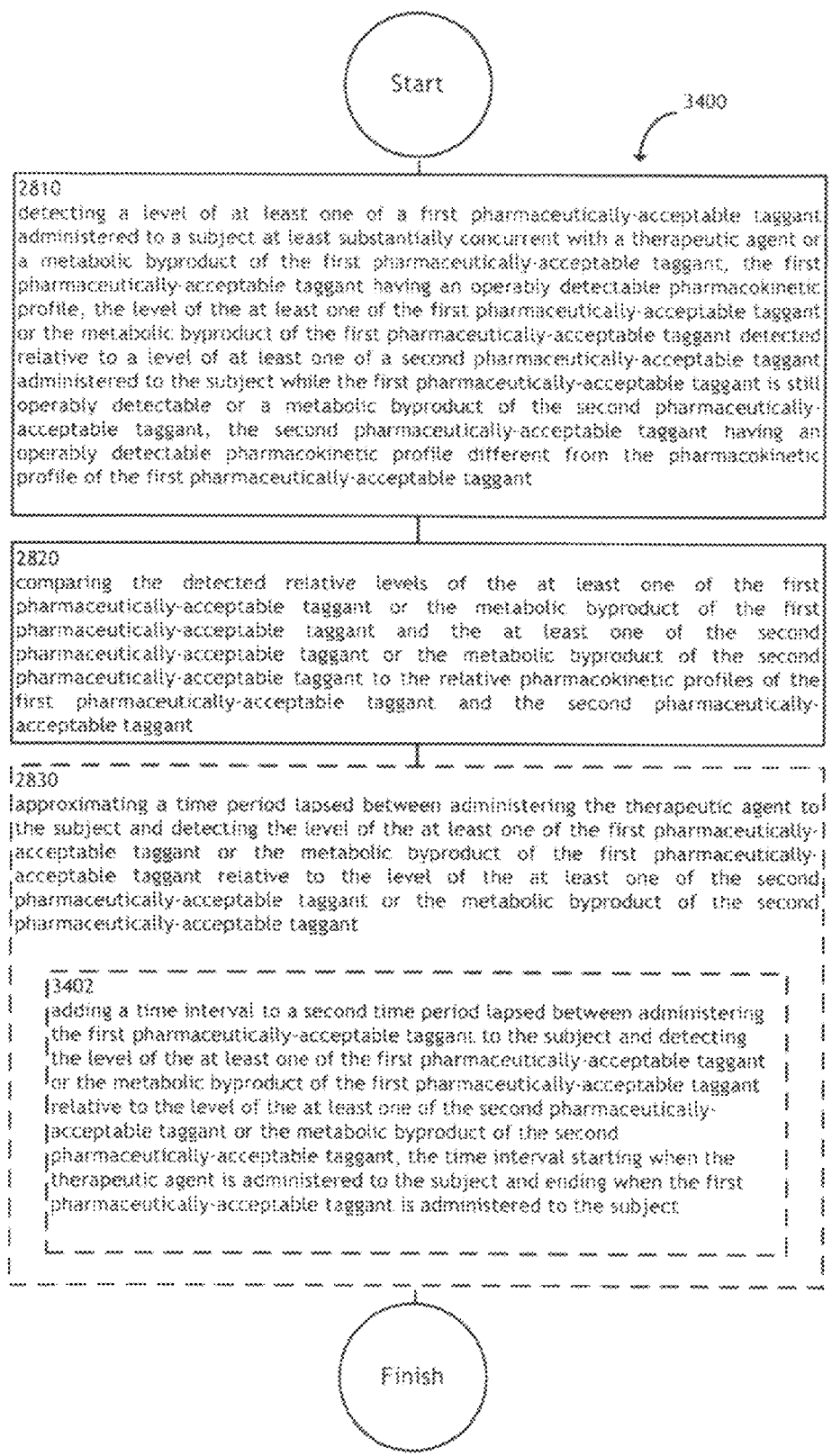
FIG. 34 illustrates an alternative embodiment of the operational flow of FIG. 28.

FIG. 34 illustrates alternative embodiments of the example operational flow 2800 of FIG. 28. FIG. 34 illustrates example embodiments where the operation 2830 may include at least one additional operation. Additional operations may include an operation 3402.

The operation 3402 illustrates adding a time interval to a second time period lapsed between administering the first pharmaceutically-acceptable taggant to the subject and detecting the level of the at least one of the first pharmaceutically-acceptable taggant or the metabolic byproduct of the first pharmaceutically-acceptable taggant relative to the level of the at least one of the second pharmaceutically-acceptable taggant or the metabolic byproduct of the second pharmaceutically-acceptable taggant, the time interval starting when the therapeutic agent is administered to the subject and ending when the first pharmaceutically-acceptable taggant is administered to the subject. For example, as shown in FIGS. 1 through 10, a time interval 104 starting when the therapeutic agent is administered to a subject and ending when the first taggant is administered may be added to a time period lapsed 106, starting when the first taggant is administered and ending when the level of the first taggant is detected relative to the level of the second taggant.

Figure 35:
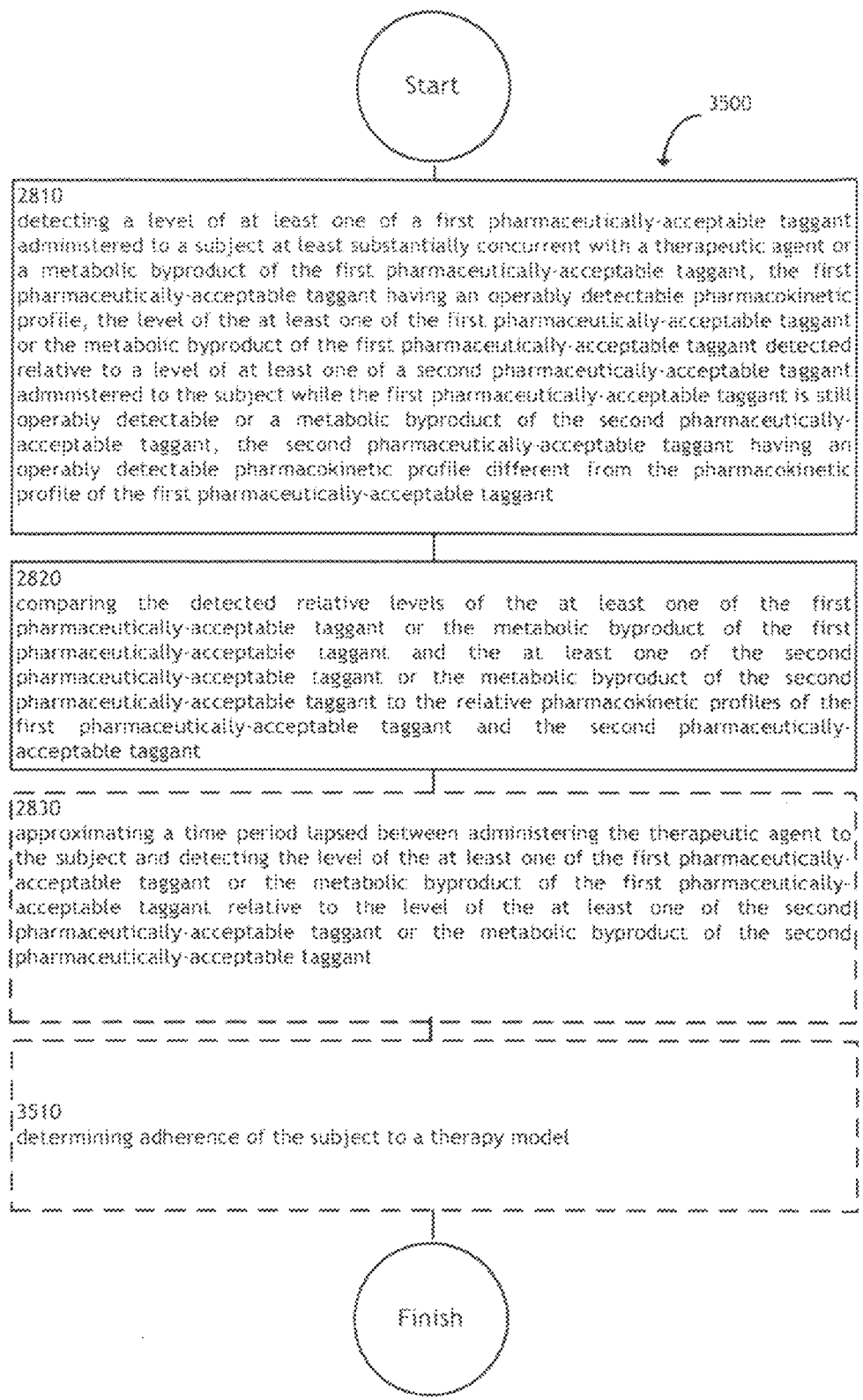
FIG. 35 illustrates an operational flow representing example operations related to approximating a time period lapsed between administering a therapeutic agent to a subject and detecting the level of a first pharmaceutically-acceptable taggant relative to the level of a second pharmaceutically-acceptable taggant administered to the subject.

FIG. 35 illustrates an operational flow 3500 representing example operations related to approximating a time period lapsed between administering a therapeutic agent to a subject and detecting the level of a first pharmaceutically-acceptable taggant relative to the level of a second pharmaceutically-acceptable taggant administered to the subject. FIG. 35 illustrates an example embodiment where the example operational flow 2800 of FIG. 28 may include at least one additional operation. Additional operations may include an operation 3510.

After a start operation, an operation 2810, an operation 2820, and an operation 2830, the operational flow 3500 moves to an operation 3510. Operation 3510 illustrates determining adherence of the subject to a therapy model. For example, as shown in FIGS. 1 through 10, if the therapy model requires a subject to take the therapeutic agent every eight hours, the subject may be notified when it is determined that more than eight hours have passed since the last dosage.

Figure 36:
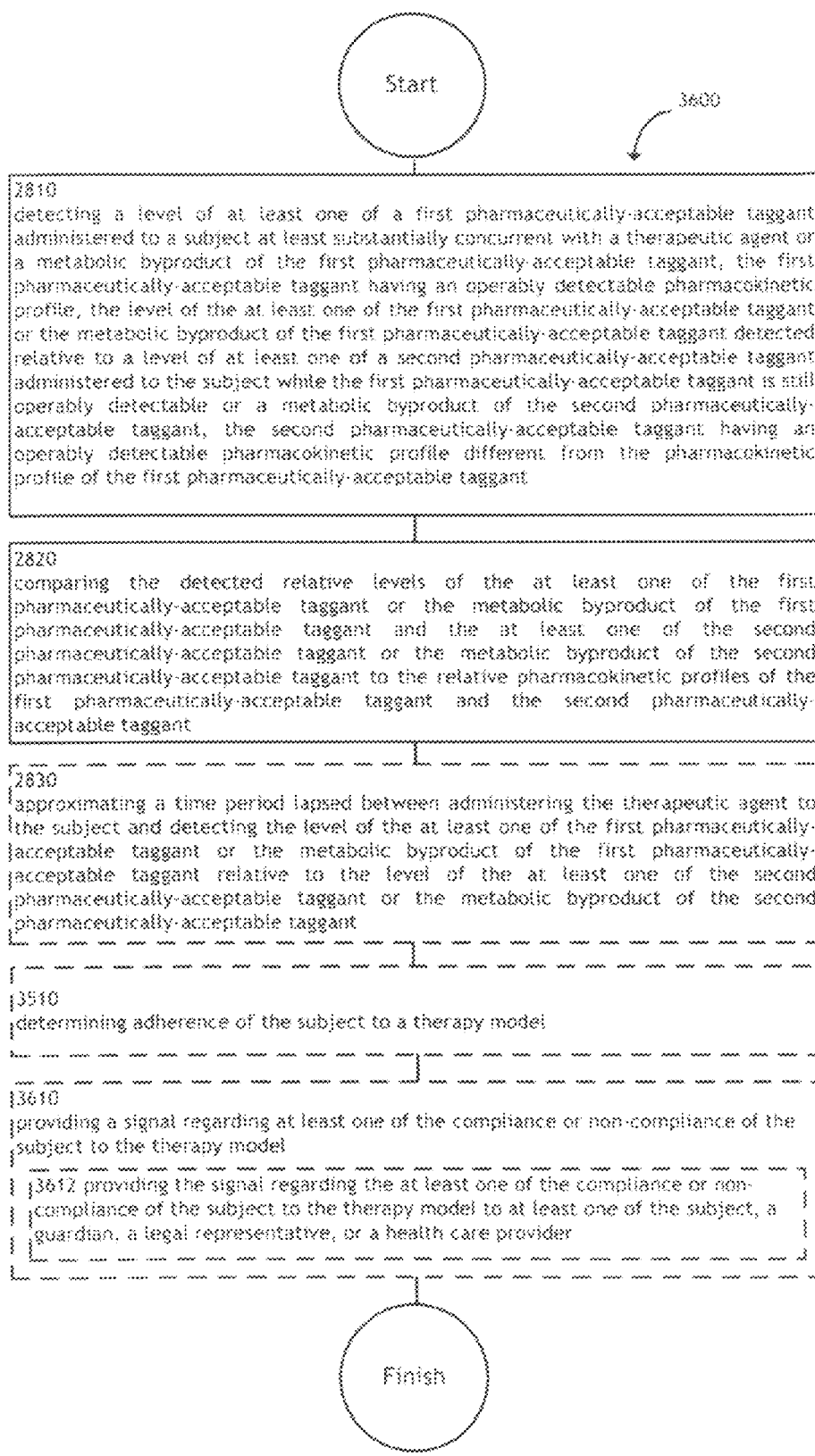
FIG. 36 illustrates an alternative embodiment of the operational flow of FIG. 35.

FIG. 36 illustrates alternative embodiments of the example operational flow 3500 of FIG. 35. FIG. 36 illustrates example embodiments where the operation 3510 may include at least one additional operation. Additional operations may include an operation 3610, and/or an operation 3612.

After a start operation, an operation 2810, an operation 2820, an operation 2830, and an operation 3510, the operational flow 3600 moves to an operation 3610. Operation 3610 illustrates providing a signal regarding at least one of the compliance or non-compliance of the subject to the therapy model.

The operation 3612 illustrates providing the signal regarding the at least one of the compliance or non-compliance of the subject to the therapy model to at least one of the subject, a guardian, a legal representative, or a health care provider. For example, as shown in FIGS. 1 through 10, the signal may be provided to a subject's primary care physician.

Figure 37:
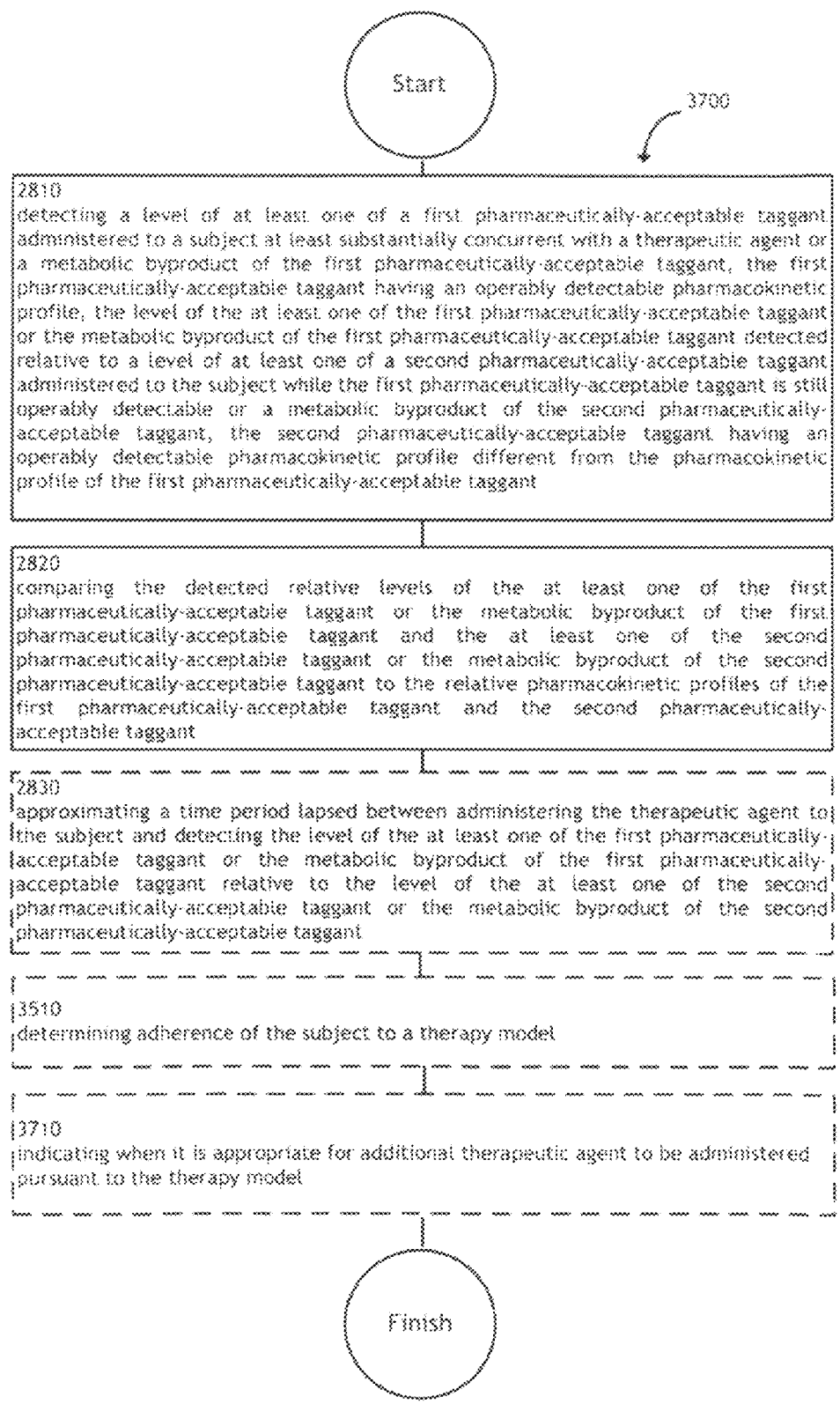
FIG. 37 illustrates an alternative embodiment of the operational flow of FIG. 35.

FIG. 37 illustrates alternative embodiments of the example operational flow 3500 of FIG. 35. FIG. 37 illustrates example embodiments where the operation 3510 may include at least one additional operation. Additional operations may include an operation 3710.

After a start operation, an operation 2810, an operation 2820, an operation 2830, and an operation 3510, the operational flow 3700 moves to an operation 3710. Operation 3710 illustrates indicating when it is appropriate for additional therapeutic agent to be administered pursuant to the therapy model.

Figure 38:
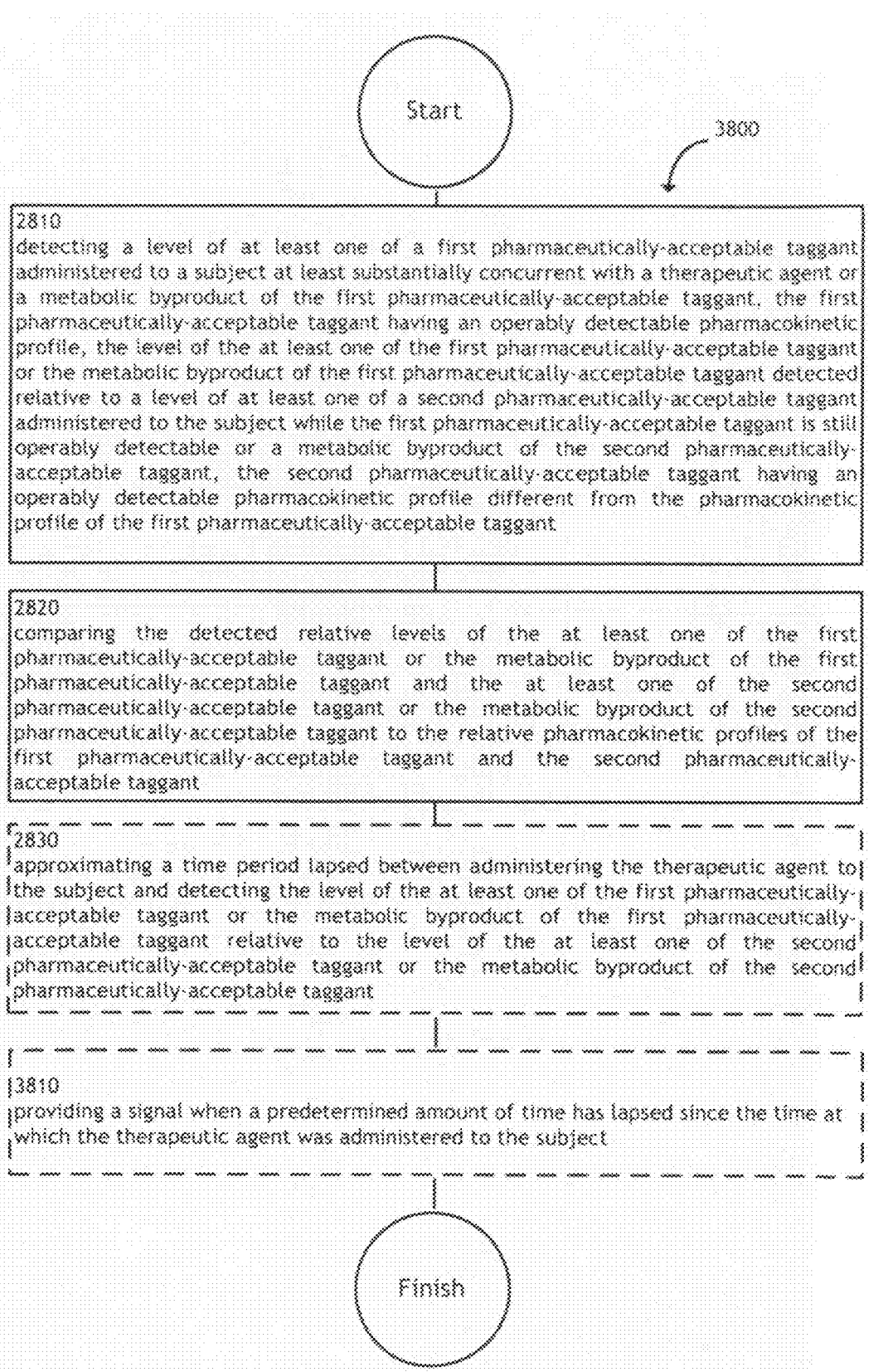
FIG. 38 illustrates an operational flow representing example operations related to determining a time period lapsed between administering a therapeutic agent to a subject and detecting relative levels for a first pharmaceutically-acceptable taggant and a second pharmaceutically-acceptable taggant administered to the subject.

FIG. 38 illustrates an operational flow 3800 representing example operations related to determining a time period lapsed between administering a therapeutic agent to a subject and detecting relative levels for a first pharmaceutically-acceptable taggant and a second pharmaceutically-acceptable taggant administered to the subject. FIG. 38 illustrates an example embodiment where the example operational flow 2800 of FIG. 28 may include at least one additional operation. Additional operations may include an operation 3810.

After a start operation, an operation 2810, an operation 2820, and an operation 2830, the operational flow 3800 moves to an operation 3810. Operation 3810 illustrates providing a signal when a predetermined amount of time has lapsed since the time at which the therapeutic agent was administered to the subject.

Figure 39:
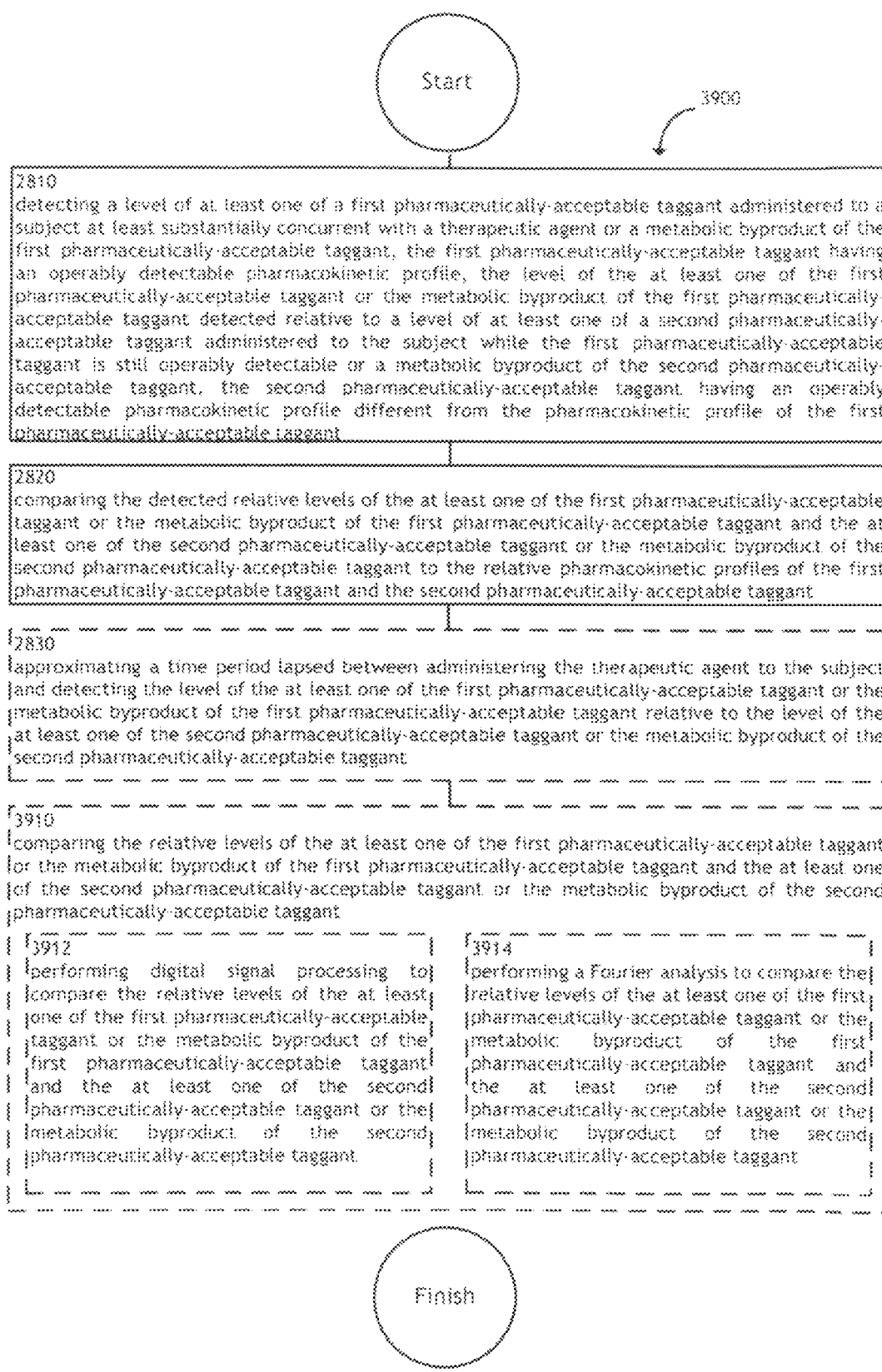
FIG. 39 illustrates an operational flow representing example operations related to determining a time period lapsed between administering a therapeutic agent to a subject and detecting relative levels for a first pharmaceutically-acceptable taggant and a second pharmaceutically-acceptable taggant administered to the subject.

FIG. 39 illustrates an operational flow 3900 representing example operations related to determining a time period lapsed between administering a therapeutic agent to a subject and detecting relative levels for a first pharmaceutically-acceptable taggant and a second pharmaceutically-acceptable taggant administered to the subject. FIG. 39 illustrates an example embodiment where the example operational flow 2800 of FIG. 28 may include at least one additional operation. Additional operations may include an operation 3910, an operation 3912, and/or an operation 3914.

After a start operation, an operation 2810, an operation 2820, and an operation 2830, the operational flow 3900 moves to an operation 3910. Operation 3910 illustrates comparing the relative levels of the at least one of the first pharmaceutically-acceptable taggant or the metabolic byproduct of the first pharmaceutically-acceptable taggant and the at least one of the second pharmaceutically-acceptable taggant or the metabolic byproduct of the second pharmaceutically-acceptable taggant.

The operation 3912 illustrates performing digital signal processing to compare the relative levels of the at least one of the first pharmaceutically-acceptable taggant or the metabolic byproduct of the first pharmaceutically-acceptable taggant and the at least one of the second pharmaceutically-acceptable taggant or the metabolic byproduct of the second pharmaceutically-acceptable taggant.

The operation 3914 illustrates performing a Fourier analysis to compare the relative levels of the at least one of the first pharmaceutically-acceptable taggant or the metabolic byproduct of the first pharmaceutically-acceptable taggant and the at least one of the second pharmaceutically-acceptable taggant or the metabolic byproduct of the second pharmaceutically-acceptable taggant.

Those having skill in the art will recognize that the state of the art has progressed to the point where there is little distinction left between hardware, software, and/or firmware implementations of aspects of systems; the use of hardware, software, and/or firmware is generally (but not always, in that in certain contexts the choice between hardware and software can become significant) a design choice representing cost vs. efficiency tradeoffs. Those having skill in the art will appreciate that there are various vehicles by which processes and/or systems and/or other technologies described herein can be effected (e.g., hardware, software, and/or firmware), and that the preferred vehicle will vary with the context in which the processes and/or systems and/or other technologies are deployed. For example, if an implementer determines that speed and accuracy are paramount, the implementer may opt for a mainly hardware and/or firmware vehicle; alternatively, if flexibility is paramount, the implementer may opt for a mainly software implementation; or, yet again alternatively, the implementer may opt for some combination of hardware, software, and/or firmware. Hence, there are several possible vehicles by which the processes and/or devices and/or other technologies described herein may be effected, none of which is inherently superior to the other in that any vehicle to be utilized is a choice dependent upon the context in which the vehicle will be deployed and the specific concerns (e.g., speed, flexibility, or predictability) of the implementer, any of which may vary. Those skilled in the art will recognize that optical aspects of implementations will typically employ optically-oriented hardware, software, and or firmware.

In some implementations described herein, logic and similar implementations may include software or other control structures suitable to operation. Electronic circuitry, for example, may manifest one or more paths of electrical current constructed and arranged to implement various logic functions as described herein. In some implementations, one or more media are configured to bear a device-detectable implementation if such media hold or transmit a special-purpose device instruction set operable to perform as described herein. In some variants, for example, this may manifest as an update or other modification of existing software or firmware, or of gate arrays or other programmable hardware, such as by performing a reception of or a transmission of one or more instructions in relation to one or more operations described herein. Alternatively or additionally, in some variants, an implementation may include special-purpose hardware, software, firmware components, and/or general-purpose components executing or otherwise invoking special-purpose components. Specifications or other implementations may be transmitted by one or more instances of tangible transmission media as described herein, optionally by packet transmission or otherwise by passing through distributed media at various times.

Alternatively or additionally, implementations may include executing a special-purpose instruction sequence or otherwise invoking circuitry for enabling, triggering, coordinating, requesting, or otherwise causing one or more occurrences of any functional operations described above. In some variants, operational or other logical descriptions herein may be expressed directly as source code and compiled or otherwise invoked as an executable instruction sequence. In some contexts, for example, C++ or other code sequences can be compiled directly or otherwise implemented in high-level descriptor languages (e.g., a logic-synthesizable language, a hardware description language, a hardware design simulation, and/or other such similar mode(s) of expression). Alternatively or additionally, some or all of the logical expression may be manifested as a Verilog-type hardware description or other circuitry model before physical implementation in hardware, especially for basic operations or timing-critical applications. Those skilled in the art will recognize how to obtain, configure, and optimize suitable transmission or computational elements, material supplies, actuators, or other common structures in light of these teachings.

The foregoing detailed description has set forth various embodiments of the devices and/or processes via the use of block diagrams, flowcharts, and/or examples. Insofar as such block diagrams, flowcharts, and/or examples contain one or more functions and/or operations, it will be understood by those within the art that each function and/or operation within such block diagrams, flowcharts, or examples can be implemented, individually and/or collectively, by a wide range of hardware, software, firmware, or virtually any combination thereof. In one embodiment, several portions of the subject matter described herein may be implemented via Application Specific Integrated Circuits (ASICs), Field Programmable Gate Arrays (FPGAs), digital signal processors (DSPs), or other integrated formats. However, those skilled in the art will recognize that some aspects of the embodiments disclosed herein, in whole or in part, can be equivalently implemented in integrated circuits, as one or more computer programs running on one or more computers (e.g., as one or more programs running on one or more computer systems), as one or more programs running on one or more processors (e.g., as one or more programs running on one or more microprocessors), as firmware, or as virtually any combination thereof, and that designing the circuitry and/or writing the code for the software and or firmware would be well within the skill of one of skill in the art in light of this disclosure. In addition, those skilled in the art will appreciate that the mechanisms of the subject matter described herein are capable of being distributed as a program product in a variety of forms, and that an illustrative embodiment of the subject matter described herein applies regardless of the particular type of signal bearing medium used to actually carry out the distribution. Examples of a signal bearing medium include, but are not limited to, the following: a recordable type medium such as a floppy disk, a hard disk drive, a Compact Disc (CD), a Digital Video Disk (DVD), a digital tape, a computer memory, etc.; and a transmission type medium such as a digital and/or an analog communication medium (e.g., a fiber optic cable, a waveguide, a wired communications link, a wireless communication link (e.g., transmitter, receiver, transmission logic, reception logic, etc.), etc.).

In a general sense, the various aspects described herein can be implemented, individually and/or collectively, by a wide range of hardware, software, firmware, and/or any combination thereof can be viewed as being composed of various types of "electrical circuitry." Consequently, as used herein "electrical circuitry" includes, but is not limited to, electrical circuitry having at least one discrete electrical circuit, electrical circuitry having at least one integrated circuit, electrical circuitry having at least one application specific integrated circuit, electrical circuitry forming a general purpose computing device configured by a computer program (e.g., a general purpose computer configured by a computer program which at least partially carries out processes and/or devices described herein, or a microprocessor configured by a computer program which at least partially carries out processes and/or devices described herein), electrical circuitry forming a memory device (e.g., forms of memory (e.g., random access, flash, read only, etc.)), and/or electrical circuitry forming a communications device (e.g., a modem, communications switch, optical-electrical equipment, etc.). The subject matter described herein may be implemented in an analog or digital fashion or some combination thereof.

At least a portion of the devices and/or processes described herein can be integrated into a data processing system. A data processing system generally includes one or more of a system unit housing, a video display device, memory such as volatile or non-volatile memory, processors such as microprocessors or digital signal processors, computational entities such as operating systems, drivers, graphical user interfaces, and applications programs, one or more interaction devices (e.g., a touch pad, a touch screen, an antenna, etc.), and/or control systems including feedback loops and control motors (e.g., feedback for sensing position and/or velocity; control motors for moving and/or adjusting components and/or quantities). A data processing system may be implemented utilizing suitable commercially available components, such as those typically found in data computing/communication and/or network computing/communication systems.

The herein described subject matter sometimes illustrates different components contained within, or connected with, different other components. It is to be understood that such depicted architectures are merely exemplary, and that in fact many other architectures may be implemented which achieve the same functionality. In a conceptual sense, any arrangement of components to achieve the same functionality is effectively "associated" such that the desired functionality is achieved. Hence, any two components herein combined to achieve a particular functionality can be seen as "associated with" each other such that the desired functionality is achieved, irrespective of architectures or intermedial components. Likewise, any two components so associated can also be viewed as being "operably connected", or "operably coupled", to each other to achieve the desired functionality, and any two components capable of being so associated can also be viewed as being "operably couplable", to each other to achieve the desired functionality. Specific examples of operably couplable include but are not limited to physically mateable and/or physically interacting components, and/or wirelessly interactable, and/or wirelessly interacting components, and/or logically interacting, and/or logically interactable components.

In some instances, one or more components may be referred to herein as "configured to," "configurable to," "operable/operative to," "adapted/adaptable," "able to," "conformable/conformed to," etc. Those skilled in the art will recognize that "configured to" can generally encompass active-state components and/or inactive-state components and/or standby-state components, unless context requires otherwise.

While particular aspects of the present subject matter described herein have been shown and described, it wilt be apparent that, based upon the teachings herein, changes and modifications may be made without departing from the subject matter described herein and its broader aspects and, therefore, the appended claims are to encompass within their scope all such changes and modifications as are within the true spirit and scope of the subject matter described herein. In general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). If a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to claims containing only one such recitation, even when the same claim includes the introductory phrases "one or more" or "at least one" and indefinite articles such as "a" or "an" (e.g., "a" and/or "an" should typically be interpreted to mean "at least one" or "one or more"); the same holds true for the use of definite articles used to introduce claim recitations. In addition, even if a specific number of an introduced claim recitation is explicitly recited, it is contemplated that such recitation should typically be interpreted to mean at least the recited number (e.g., the bare recitation of "two recitations," without other modifiers, typically means at least two recitations, or two or more recitations). Furthermore, in those instances where a convention analogous to "at least one of A, B, and C, etc." is used, in general such a construction is intended (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.). Typically a disjunctive word and/or phrase presenting two or more alternative terms, whether in the description, claims, or drawings, should be understood to contemplate the possibilities of including one of the terms, either of the terms, or both terms. For example, the phrase "A or B" will be typically understood to include the possibilities of "A" or "B" or "A and B."

With respect to the appended claims, the recited operations therein may generally be performed in any order. Also, although various operational flows are presented in a sequence(s), it should be understood that the various operations may be performed in other orders than those which are illustrated, or may be performed concurrently. Examples of such alternate orderings may include overlapping, interleaved, interrupted, reordered, incremental, preparatory, supplemental, simultaneous, reverse, or other variant orderings, unless context dictates otherwise. Furthermore, terms like "responsive to," "related to," or other past-tense adjectives are generally not intended to exclude such variants, unless context dictates otherwise.

What is claimed is:

1. A system, comprising:
   means for detecting a concentration of at least one of a first pharmaceutically-acceptable taggant administered to a subject at least substantially concurrent with a therapeutic agent or a metabolic byproduct of the first pharmaceutically-acceptable taggant, the first pharmaceutically-acceptable taggant having a pharmacokinetic profile;
   means for detecting a concentration of at least one of a second pharmaceutically-acceptable taggant administered to the subject with the first pharmaceutically-acceptable taggant or a metabolic byproduct of the second pharmaceutically-acceptable taggant, the second pharmaceutically-acceptable taggant having a pharmacokinetic profile different from the pharmacokinetic profile of the first pharmaceutically-acceptable taggant;
   means for referencing the concentration of the at least one of the first pharmaceutically-acceptable taggant or the metabolic byproduct of the first pharmaceutically-acceptable taggant to the pharmacokinetic profile of the first pharmaceutically-acceptable taggant;
   means for referencing the concentration of the at least one of the second pharmaceutically-acceptable taggant or the metabolic byproduct of the second pharmaceutically-acceptable taggant to the pharmacokinetic profile of the second pharmaceutically-acceptable taggant; and
   means for approximating a time period lapsed between administering the therapeutic agent to the subject and detecting the concentration of the at least one of the second pharmaceutically-acceptable taggant or the metabolic byproduct of the second pharmaceutically-acceptable taggant.

2. The system of claim 1, wherein the second pharmaceutically-acceptable taggant is administered to the subject concurrent with the first pharmaceutically-acceptable taggant.

3. The system of claim 1, wherein the second pharmaceutically-acceptable taggant is administered to the subject subsequent to the first pharmaceutically-acceptable taggant.

4. The system of claim 1, further comprising:
   means for detecting a second concentration of at least one of the first pharmaceutically-acceptable taggant or a metabolic byproduct of the first pharmaceutically-acceptable taggant.

5. The system of claim 1, further comprising:
   means for detecting a second concentration of at least one of the first pharmaceutically-acceptable taggant or a metabolic byproduct of the first pharmaceutically-acceptable taggant relative to the first concentration of the at least one of the first pharmaceutically-acceptable taggant or the metabolic byproduct of the first pharmaceutically-acceptable taggant.

6. The system of claim 1, wherein at least one of the first pharmaceutically-acceptable taggant or the second pharmaceutically-acceptable taggant is at least substantially co-administered to the subject with the therapeutic agent.

7. The system of claim 1, wherein the therapeutic agent comprises:
   a therapeutic agent for at least one of modulating, curing, diagnosing, mitigating, preventing, or treating at least one of a disease or a condition.

8. The system of claim 1, wherein the therapeutic agent comprises:
   a therapeutic agent for enhancing at least one of a physical well-being or a mental well-being.

9. The system of claim 1, further comprising:
   means for administering the therapeutic agent via at least one of a duodenal route of administration, enterally, epicutaneously, epidurally, gastrically, an inhalational route of administration, intraarterially, an intracardiac route of administration, intradermally, intramuscularly, intranasally, intraocularly, intraosseous infusion, intraperitoneally, intrathecally, an intrauterine route of administration, intravaginally, intravenously, intravesically, intravitreally, nasally, nasogastric intubation, orally, rectally, subcutaneously, sublingually, transdermally, or transmucosally.

10. The system of claim 9, wherein the means for administering the therapeutic agent via at least one of a duodenal route of administration, enterally, epicutaneously, epidurally, gastrically, an inhalational route of administration, intraarterially, an intracardiac route of administration, intradermally, intramuscularly, intranasally, intraocularly, intraosseous infusion, intraperitoneally, intrathecally, an intrauterine route of administration, intravaginally, intravenously, intravesically, intravitreally, nasally, nasogastric intubation, orally, rectally, subcutaneously, sublingually, transdermally, or transmucosally comprises:
means for administering the therapeutic agent via an injection.

11. The system of claim 1, wherein at least one of the first pharmaceutically-acceptable taggant or the second pharmaceutically-acceptable taggant comprises:
at least one of a dye, a fluorophore, an MRI contrast agent, an ultrasound contrast agent, or an x-ray contrast agent.

12. The system of claim 1, wherein the first pharmaceutically-acceptable taggant possesses a half-life different from a half-life for the second pharmaceutically-acceptable taggant.

13. The system of claim 1, wherein at least one of the first pharmaceutically-acceptable taggant or the second pharmaceutically-acceptable taggant possesses a half-life less than or equal to a half-life for the therapeutic agent.

14. The system of claim 1, wherein at least one of the first pharmaceutically-acceptable taggant or the second pharmaceutically-acceptable taggant possesses a half-life greater than or equal to a half-life for the therapeutic agent.

15. The system of claim 1, wherein the first pharmaceutically-acceptable taggant possesses a metabolic absorption rate different from a metabolic absorption rate for the second pharmaceutically-acceptable taggant.

16. The system of claim 1, wherein the means for detecting a concentration of at least one of a first pharmaceutically-acceptable taggant administered to a subject at least substantially concurrent with a therapeutic agent or a metabolic byproduct of the first pharmaceutically-acceptable taggant comprises:
means for performing a noninvasive ex vivo assay.

17. The system of claim 16, wherein the means for performing a noninvasive ex vivo assay comprises:
means for assaying an expired breath of the subject with a gas-analytic device.

18. The system of claim 16, wherein the means for performing a noninvasive ex vivo assay comprises:
means for assaying a fluid exuded by the skin of the subject.

19. The system of claim 16, wherein the means for performing a noninvasive ex vivo assay comprises:
means for assaying at least one of feces, hair, or urine of the subject.

20. The system of claim 1, wherein the means for detecting a concentration of at least one of a second pharmaceutically-acceptable taggant administered to the subject with the first pharmaceutically-acceptable taggant or a metabolic byproduct of the second pharmaceutically-acceptable taggant comprises:
means for performing a noninvasive ex vivo assay.

21. The system of claim 20, wherein the means for performing a noninvasive ex vivo assay comprises:
means for assaying an expired breath of the subject with a gas-analytic device.

22. The system of claim 20, wherein the means for performing a noninvasive ex vivo assay comprises:
means for assaying a fluid exuded by the skin of the subject.

23. The system of claim 20, wherein the means for performing a noninvasive ex vivo assay comprises:
means for assaying at least one of feces, hair, or urine of the subject.

24. The system of claim 1, wherein the means for detecting a concentration of at least one of a first pharmaceutically-acceptable taggant administered to a subject at least substantially concurrent with a therapeutic agent or a metabolic byproduct of the first pharmaceutically-acceptable taggant comprises:
means for performing a noninvasive in vivo assay.

25. The system of claim 24, wherein the means for performing a noninvasive in vivo assay comprises:
means for performing at least one of a transdermal measurement or a retinal measurement on the subject.

26. The system of claim 24, wherein the means for performing a noninvasive in vivo assay comprises:
means for detecting the first pharmaceutically-acceptable taggant by at least one of an x-ray fluorescence, an optical fluorescence, an MRI signature, an ultrasound signature, or an x-ray signature.

27. The system of claim 1, wherein the means for detecting a concentration of at least one of a second pharmaceutically-acceptable taggant administered to the subject with the first pharmaceutically-acceptable taggant or a metabolic byproduct of the second pharmaceutically-acceptable taggant comprises:
means for performing a noninvasive in vivo assay.

28. The system of claim 27, wherein the means for performing a noninvasive in vivo assay comprises:
means for performing at least one of a transdermal measurement or a retinal measurement on the subject.

29. The system of claim 27, wherein the means for performing a noninvasive in vivo assay comprises:
means for detecting the second pharmaceutically-acceptable taggant by at least one of an x-ray fluorescence, an optical fluorescence, an MRI signature, an ultrasound signature, or an x-ray signature.

30. The system of claim 1, wherein the means for detecting a concentration of at least one of a first pharmaceutically-acceptable taggant administered to a subject at least substantially concurrent with a therapeutic agent or a metabolic byproduct of the first pharmaceutically-acceptable taggant further comprises:
means for associating a sensor with the subject, the sensor configured to detect the at least one of the first pharmaceutically-acceptable taggant or the metabolic byproduct of the first pharmaceutically-acceptable taggant.

31. The system of claim 1, wherein the means for detecting a concentration of at least one of a second pharmaceutically-acceptable taggant administered to the subject with the first pharmaceutically-acceptable taggant or a metabolic byproduct of the second pharmaceutically-acceptable taggant further comprises:
means for associating a sensor with the subject, the sensor configured to detect the at least one of the second pharmaceutically-acceptable taggant or the metabolic byproduct of the second pharmaceutically-acceptable taggant.

32. The system of claim 1, wherein the means for detecting a concentration of at least one of a first pharmaceutically-acceptable taggant administered to a subject at least substantially concurrent with a therapeutic agent or a metabolic byproduct of the first pharmaceutically-acceptable taggant comprises:

means for intermittently detecting the concentration of the at least one of the first pharmaceutically-acceptable taggant or the metabolic byproduct of the first pharmaceutically-acceptable taggant.

33. The system of claim 1, wherein the means for detecting a concentration of at least one of a second pharmaceutically-acceptable taggant administered to the subject with the first pharmaceutically-acceptable taggant or a metabolic byproduct of the second pharmaceutically-acceptable taggant comprises:

means for intermittently detecting the concentration of the at least one of the second pharmaceutically-acceptable taggant or the metabolic byproduct of the second pharmaceutically-acceptable taggant.

34. The system of claim 1, wherein the means for detecting a concentration of at least one of a second pharmaceutically-acceptable taggant administered to the subject with the first pharmaceutically-acceptable taggant or a metabolic byproduct of the second pharmaceutically-acceptable taggant further comprises:

means for detecting a second concentration of at least one of the second pharmaceutically-acceptable taggant or a metabolic byproduct of the second pharmaceutically-acceptable taggant.

35. The system of claim 1, wherein the means for approximating a time period lapsed between administering the therapeutic agent to the subject and detecting the concentration of the at least one of the second pharmaceutically-acceptable taggant or the metabolic byproduct of the second pharmaceutically-acceptable taggant comprises:

means for adding a time interval to a second time period lapsed between administering the first pharmaceutically-acceptable taggant to the subject and detecting the concentration of the at least one of the second pharmaceutically-acceptable taggant or the metabolic byproduct of the second pharmaceutically-acceptable taggant, the time interval starting when the therapeutic agent is administered to the subject and ending when the first pharmaceutically-acceptable taggant is administered to the subject.

36. The system of claim 1, further comprising:
means for determining adherence of the subject to a therapy model.

37. The system of claim 36, further comprising:
means for providing a signal regarding at least one of the compliance or non-compliance of the subject to the therapy model.

38. The system of claim 37, wherein the means for providing a signal regarding at least one of the compliance or non-compliance of the subject to the therapy model comprises:

means for providing the signal regarding the at least one of the compliance or non-compliance of the subject to the therapy model to at least one of the subject, a guardian, a legal representative, or a health care provider.

39. The system of claim 36, further comprising:
means for indicating when it is appropriate for additional therapeutic agent to be administered pursuant to the therapy model.

40. The system of claim 1, further comprising:
means for providing a signal when a predetermined amount of time has lapsed since the time at which the therapeutic agent was administered to the subject.

41. The system of claim 1, further comprising:
means for comparing the concentration of the at least one of the first pharmaceutically-acceptable taggant or the metabolic byproduct of the first pharmaceutically-acceptable taggant to the concentration of the at least one of the second pharmaceutically-acceptable taggant or the metabolic byproduct of the second pharmaceutically-acceptable taggant.

42. The system of claim 41, wherein the means for comparing the concentration of the at least one of the first pharmaceutically-acceptable taggant or the metabolic byproduct of the first pharmaceutically-acceptable taggant to the concentration of the at least one of the second pharmaceutically-acceptable taggant or the metabolic byproduct of the second pharmaceutically-acceptable taggant comprises:

means for performing digital signal processing to compare the concentration of the at least one of the first pharmaceutically-acceptable taggant or the metabolic byproduct of the first pharmaceutically-acceptable taggant to the concentration of the at least one of the second pharmaceutically-acceptable taggant or the metabolic byproduct of the second pharmaceutically-acceptable taggant.

43. The system of claim 41, wherein the means for comparing the concentration of the at least one of the first pharmaceutically-acceptable taggant or the metabolic byproduct of the first pharmaceutically-acceptable taggant to the concentration of the at least one of the second pharmaceutically-acceptable taggant or the metabolic byproduct of the second pharmaceutically-acceptable taggant comprises:

means for performing a Fourier analysis to compare the concentration of the at least one of the first pharmaceutically-acceptable taggant or the metabolic byproduct of the first pharmaceutically-acceptable taggant to the concentration of the at least one of the second pharmaceutically-acceptable taggant or the metabolic byproduct of the second pharmaceutically-acceptable taggant.

* * * * *